US012590156B2

(12) United States Patent
Kim et al.

(10) Patent No.: US 12,590,156 B2
(45) Date of Patent: Mar. 31, 2026

(54) FUSION ANTIBODY FOR PRESENTING ANTIGEN-DERIVED T CELL ANTIGEN EPITOPE OR PEPTIDE CONTAINING SAME ON CELL SURFACE, AND COMPOSITION COMPRISING SAME

(71) Applicant: AJOU UNIVERSITY INDUSTRY-ACADEMIC COOPERATION FOUNDATION, Suwon-si (KR)

(72) Inventors: Yong Sung Kim, Suwon-si (KR); Jeong-Ah Kim, Gwangju-si (KR); Keunok Jung, Suwon-si (KR); Seyoung Lee, Seoul (KR); Min-Jeong Son, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 715 days.

(21) Appl. No.: 17/796,788

(22) PCT Filed: Feb. 5, 2021

(86) PCT No.: PCT/KR2021/001571
§ 371 (c)(1),
(2) Date: Aug. 1, 2022

(87) PCT Pub. No.: WO2021/158073
PCT Pub. Date: Aug. 12, 2021

(65) Prior Publication Data
US 2023/0076637 A1     Mar. 9, 2023

(30) Foreign Application Priority Data
Feb. 6, 2020    (KR) ........................ 10-2020-0014468

(51) Int. Cl.
| A61P 31/00 | (2006.01) |
| A61K 40/11 | (2025.01) |
| A61K 40/42 | (2025.01) |
| A61K 40/46 | (2025.01) |
| C07K 14/705 | (2006.01) |
| C07K 16/085 | (2026.01) |
| C07K 16/28 | (2006.01) |
| C12N 15/63 | (2006.01) |
| A61K 39/00 | (2006.01) |

(52) U.S. Cl.
CPC ........ *C07K 14/70517* (2013.01); *A61K 40/11* (2025.01); *A61K 40/42* (2025.01); *A61K 40/46* (2025.01); *A61P 31/00* (2018.01); *C07K 16/089* (2023.08); *C07K 16/2833* (2013.01); *C07K 16/2839* (2013.01); *C12N 15/63* (2013.01); *A61K 2039/505* (2013.01); *A61K 2239/31* (2023.05); *A61K 2239/38* (2023.05); *A61K 2239/49* (2023.05); *C07K 2317/522*

(2013.01); *C07K 2317/524* (2013.01); *C07K 2317/526* (2013.01); *C07K 2317/53* (2013.01); *C07K 2319/00* (2013.01)

(58) Field of Classification Search
CPC ....................................................... A61P 31/00
USPC ....................................................... 424/134.1
See application file for complete search history.

(56) References Cited

U.S. PATENT DOCUMENTS

| 2002/0156251 A1* | 10/2002 | Prieur ................. C07K 14/005 |
| | | 536/23.1 |
| 2014/0161826 A1 | 6/2014 | Pessi |
| 2018/0078655 A1 | 3/2018 | Dziadek et al. |

FOREIGN PATENT DOCUMENTS

| CN | 107922493 A | 4/2018 |
| JP | 2015-512246 A | 4/2015 |
| KR | 10-1602870 B1 | 3/2016 |
| KR | 10-2019-0132338 A | 11/2019 |
| WO | 2012/123755 A1 | 9/2012 |
| WO | 2015/199618 A1 | 12/2015 |
| WO | 2016/126611 A1 | 8/2016 |
| WO | 2016/131856 A1 | 8/2016 |
| WO | 2016/182957 A1 | 11/2016 |
| WO | 2019/132579 A2 | 7/2019 |

OTHER PUBLICATIONS

Kaliamurthi et al (Biologics: Targets and Therapy, 2018, 107-125).*
Wen et al (Analytical Chemistry, 2013, 85: 4805-4812).*
Austin et al (Molecular Biology of the Cell, 2004, 15: 5268-5282).*
Shen et al (Immunology, 2006, 117: 78-88).*
Communication dated Mar. 25, 2024 issued by the European Patent Office in application No. 21750828.2.
Keunok Jung, et al., "Antibody-mediated delivery of a viral MHC-I epitope into the cytosol of target tumor cells repurposes virus-specific CD8+ T cells for cancer immunotherapy", Molecular Cancer, vol. 21, No. 102, 2022, pp. 1-20.

(Continued)

*Primary Examiner* — Sean E Aeder

(74) *Attorney, Agent, or Firm* — Sughrue Mion, PLLC

(57) ABSTRACT

The present invention relates to: a composition for delivering a viral antigen-derived CD8+ T cell antigen epitope or a peptide comprising same to the cytoplasm of a target cell to thereby present the epitope or peptide to major histocompatibility complex class I (MAC-1), which is an antigen-presenting molecule on the cell surface; a composition comprising same; and a use thereof.

22 Claims, 36 Drawing Sheets
Specification includes a Sequence Listing.

(56)          References Cited

OTHER PUBLICATIONS

Sagun Parakh, et al., "Antibody-mediated delivery of therapeutics for cancer therapy", Expert Opinion on Drug Delivery, vol. 13, No. 3, 2016, pp. 401-419 (20 pages).

Herrmann, Andreas et al., "An effective cell-penetrating antibody delivery platform", JCI insight, 2019, pp. 1-19, vol. 4, issue 14, e127474.

Geraldine A. O'Hara et al., "Memory T cell inflation: understanding cause and effect", Trends Immunol., Feb. 2012, pp. 84-90, vol. 33, No. 2.

Pamera C. Rosato et al., "Virus-specific memory T cells populate tumors and can be repurposed for tumor immunotherapy", Nature Communications vol. 2019, pp. 1-9, 10:567.

Stephanie A. S. Staras et al., "Seroprevalence of Cytomegalovirus Infection in the United States, 1988-1994", Clin Infect Dis, Nov. 2006, pp. 1143-1151, 43(9).

Junyun Lai et al., "TCR-like antibodies mediate complement and antibody dependent cellular cytotoxicity against Epstein-Barr virus-transformed B lymphoblastoid cells expressing different HLA-A*02 microvariants", Scientific Reports, Aug. 30, 2017, pp. 1-11, 7:9923.

Smita K. Nair et al., "Recognition and Killing of Autologous, Primary Glioblastoma Tumor Cells by Human Cytomegalovirus pp65-Specific Cytotoxic T Cells", Clin Cancer Res., May 15, 2014, pp. 2684-2694, 20(10).

Wenjie Yin et al., "Therapeutic HPV Cancer Vaccine Targeted to CD40 Elicits Effective CD8+ T-cell Immunity", Cancer Immunol Res., Oct. 2016, pp. 823-834, 4(10).

Chuong D. Pham et al., "An Anti-Nucleic Acid Antibody Delivers Antigen to the Cross-Presentation Pathway in Dendritic Cells and Potentiates Therapeutic Antitumor Effects", J Immunol., 2012, pp. 5755-5763, 189(12).

Julian P. Sefrin et al., "Sensitization of Tumors for Attack by Virus-Specific CD8+ T-Cells Through Antibody-Mediated Delivery of Immunogenic T-Cell Epitopes", Front. Immunol., Aug. 2019, pp. 1-14, vol. 10, Article 1962.

Martina Schmittnaegel et al., "Committing Cytomegalovirus-Specific CD8 T Cells to Eliminate Tumor Cells by Bifunctional Major Histocompatibility Class I Antibody Fusion Molecules", Cancer Immunol Res., Jul. 2015, pp. 764-776, 3(7).

International Search Report of PCT/KR2021/001571 dated May 12, 2021 [PCT/ISA/210].

Japanese Office Action dated Oct. 17, 2023 in Japanese Application No. 2022-547813.

Grau et al., "Mechanistic insights into the efficacy of cell penetrating peptide-based cancer vaccines", Cellular and Molecular Life Sciences, 2018 (10 pages total).

Kim et al. "Engineering of a tumor cell-specific, cytosol-penetrating antibody with high endosomal escape efficacy", Biochemical And Biophysical Research Communications, 2018, vol. 503, pp. 2510-2516 (8 p. total).

Wang et al., "Mechanisms of the MHC class I-associated presentation of exogenous CTL epitope fused with cell penetrating peptides", Immunological Journal, vol. 22, No. 3, May 2005, with English translation.

Yin et al., "Production and identification of the monoclonal antibodies specific for MHC class I cpomplexes bound with HPV16E7CTL epitopic peptide", Chinese J. Exp. Clin. Virol., Sep. 2006, vol. 20, No. 3, with English translation.

* cited by examiner

[Fig. 1]
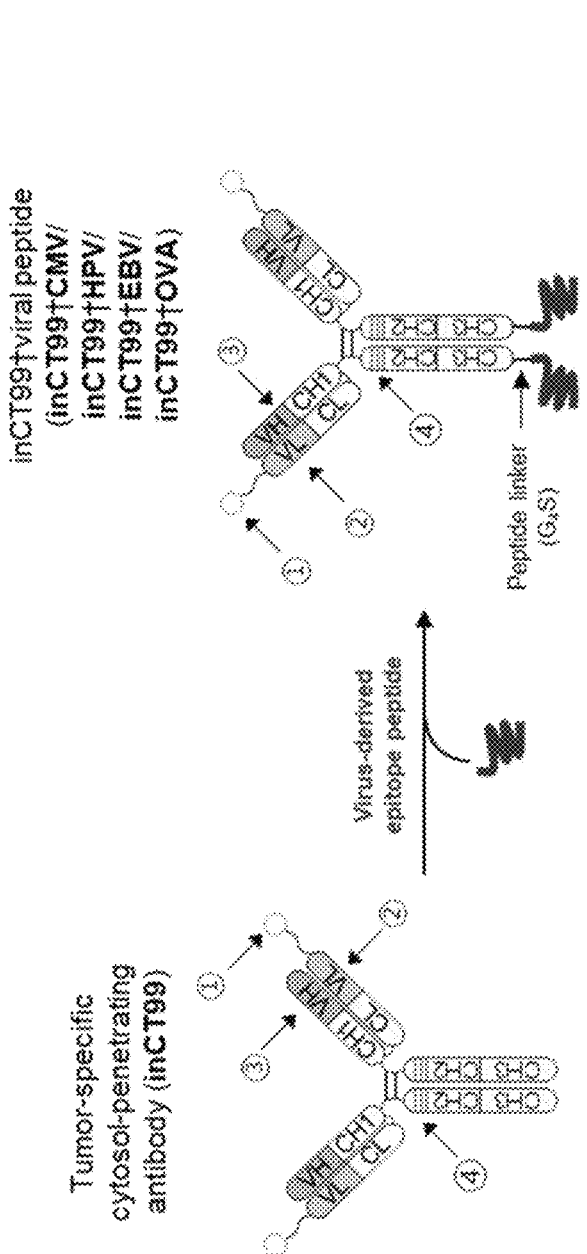
① Integrin αvβ5/αvβ3-targeting cyclic peptide (in4) for the receptor-mediated endocytosis
② VL with endosomal escape activity by introduction of $^{92}$WYW$^{94}$ in VL-CDR3
③ VH with endosomal escape activity by introduction of $^{98}$WYW$^{99}$ in VH-CDR3
④ Fc with LALAPG mutation to improve pharmacokinetics by avoiding the interactions with Fc receptors

[Fig. 2a]
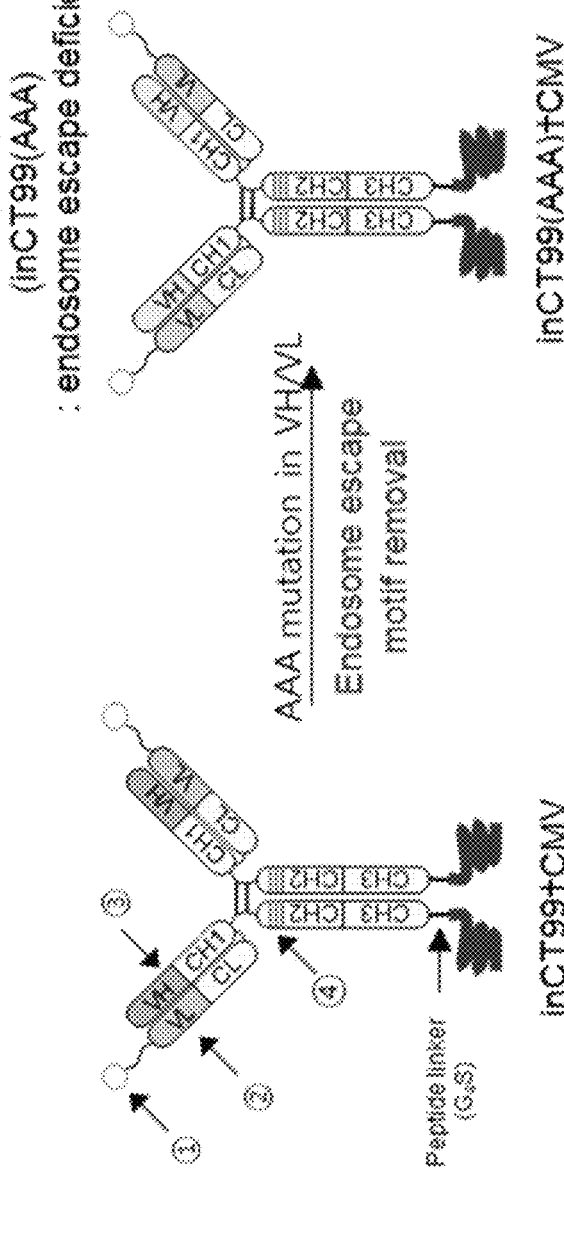

【Fig. 2b】
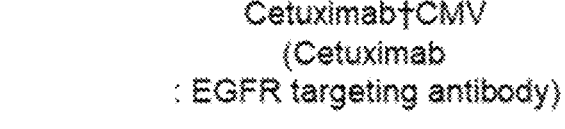
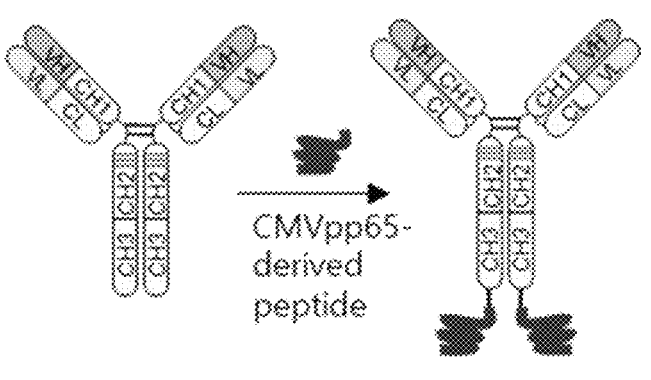
【Fig. 2c】
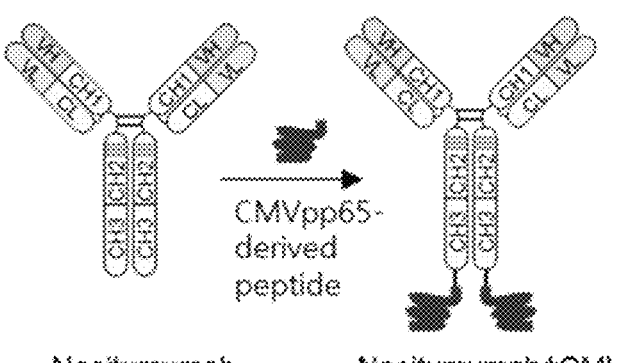

【Fig. 3a】
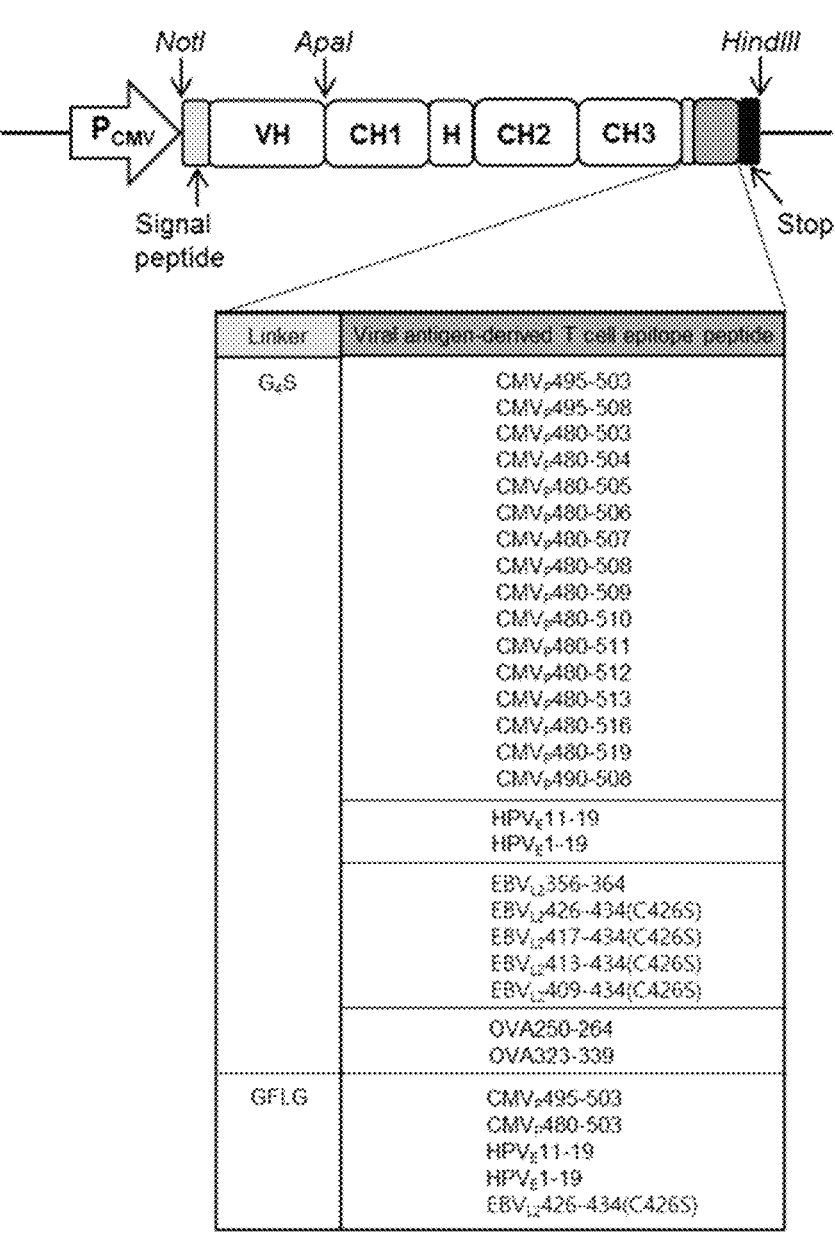
| Linker | Viral antigen-derived T cell epitope peptide |
|---|---|
| $G_4S$ | $CMV_p495-503$ |
| | $CMV_p495-508$ |
| | $CMV_p480-503$ |
| | $CMV_p480-504$ |
| | $CMV_p480-505$ |
| | $CMV_p480-506$ |
| | $CMV_p480-507$ |
| | $CMV_p480-508$ |
| | $CMV_p480-509$ |
| | $CMV_p480-510$ |
| | $CMV_p480-511$ |
| | $CMV_p480-512$ |
| | $CMV_p480-513$ |
| | $CMV_p480-518$ |
| | $CMV_p480-519$ |
| | $CMV_p490-508$ |
| | $HPV_{E7}11-19$ |
| | $HPV_{E7}1-19$ |
| | $EBV_{LMP}356-364$ |
| | $EBV_{LMP}426-434(C426S)$ |
| | $EBV_{LMP}417-434(C426S)$ |
| | $EBV_{LMP}413-434(C426S)$ |
| | $EBV_{LMP}409-434(C426S)$ |
| | OVA250-264 |
| | OVA323-339 |
| GFLG | $CMV_p495-503$ |
| | $CMV_p480-503$ |
| | $HPV_{E7}11-19$ |
| | $HPV_{E7}1-19$ |
| | $EBV_{LMP}426-434(C426S)$ |

【Fig. 3b】
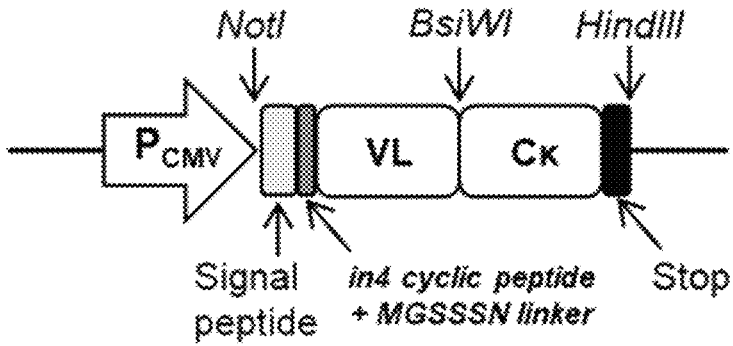
【Fig. 4a】
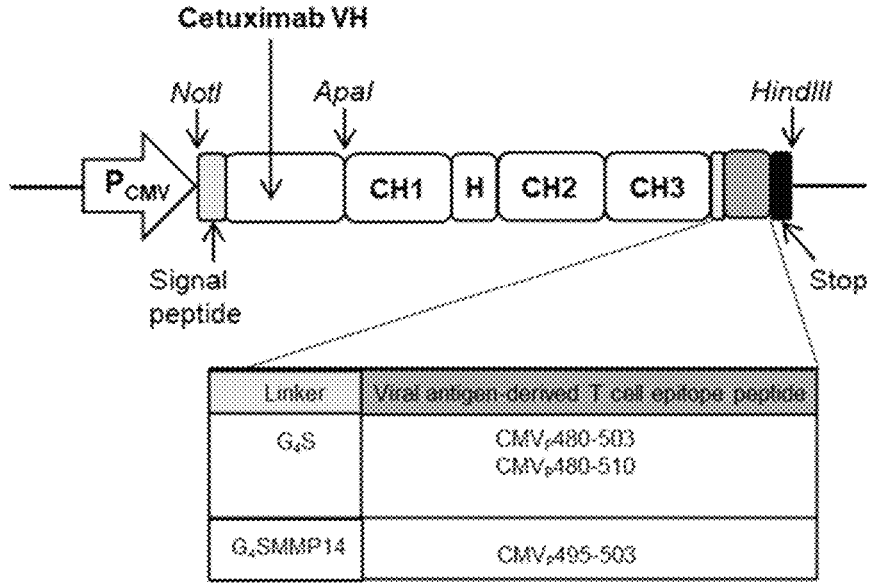
【Fig. 4b】
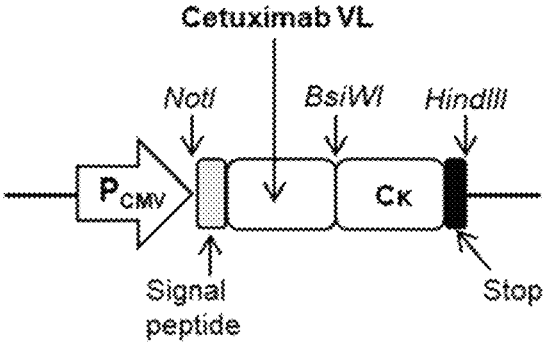

【Fig. 4c】
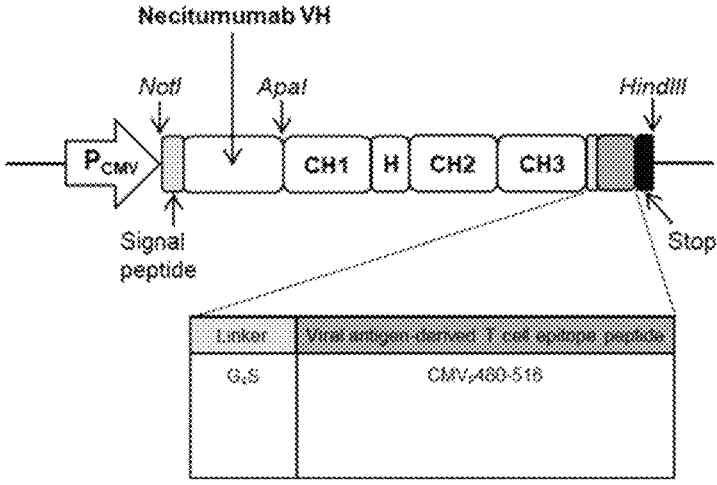
【Fig. 4d】
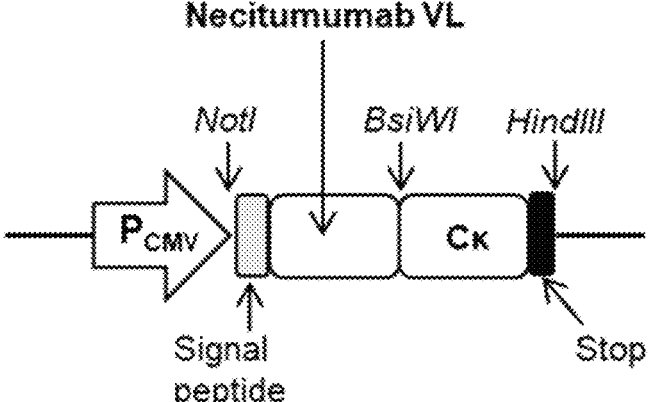

[Fig. 5a]
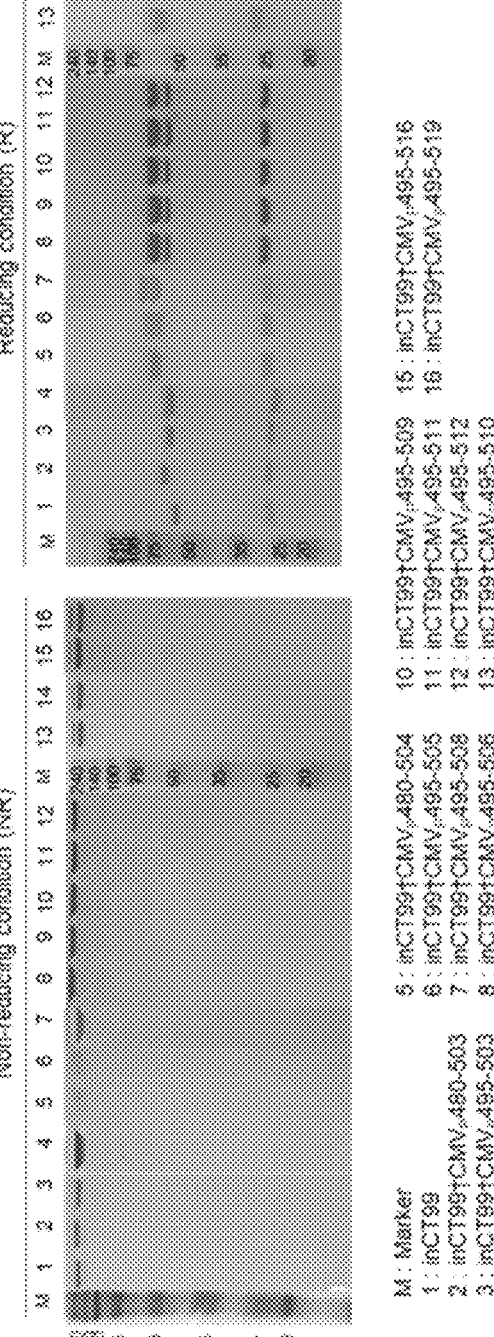

【Fig. 5b】
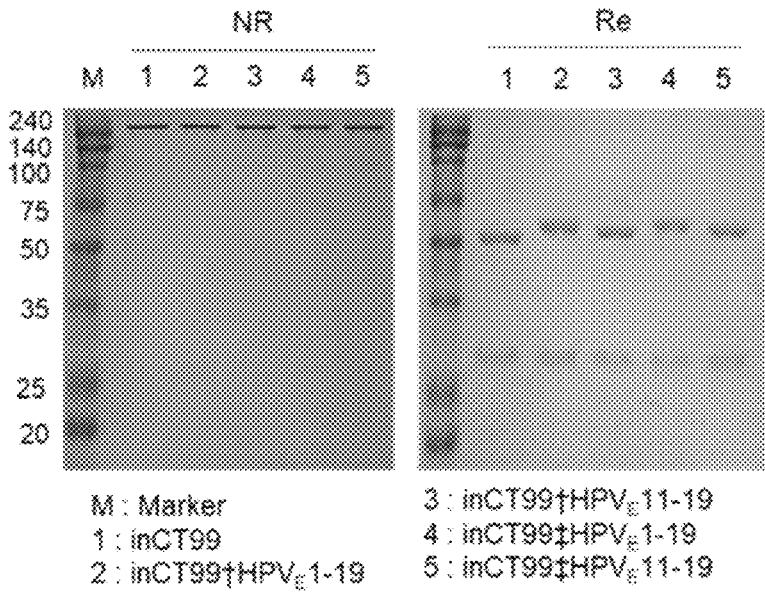
M : Marker
1 : inCT99
2 : inCT99†HPV$_E$1-19
3 : inCT99†HPV$_E$11-19
4 : inCT99‡HPV$_E$1-19
5 : inCT99‡HPV$_E$11-19
【Fig. 5c】
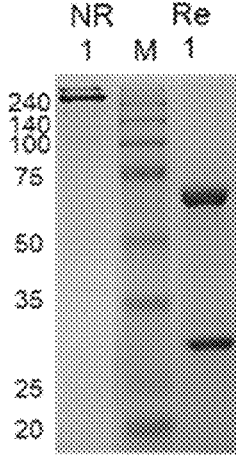
M : Marker
1: inCT99†EBV$_L$426-434(C426S)

【Fig. 5d】
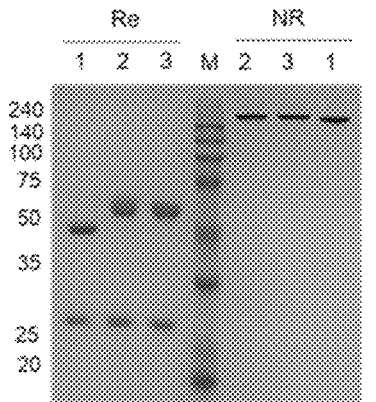
M : Marker
1 : inCT99
2 : inCT99†EBV$_L$413-434(C426S)
3 : inCT99†EBV$_L$409-434(C426S)
【Fig. 6】
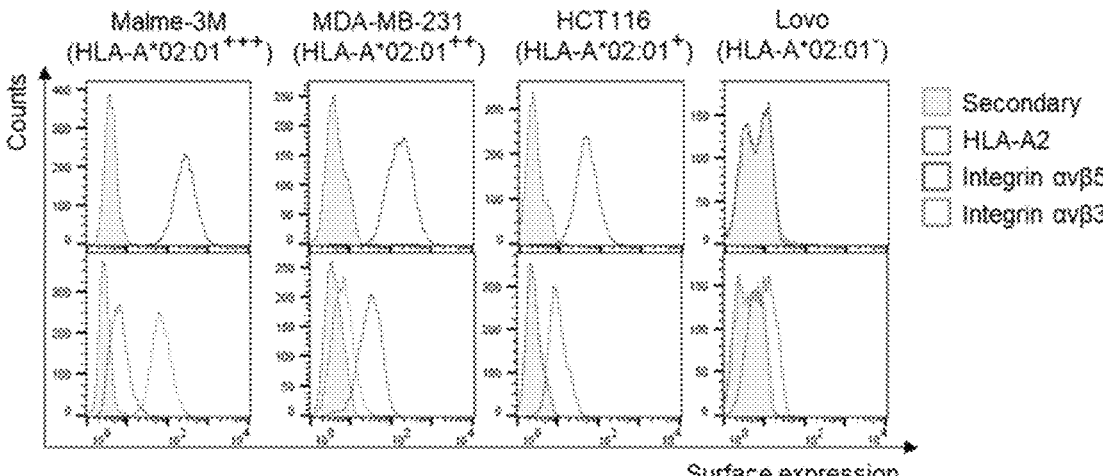

【Fig. 7a】
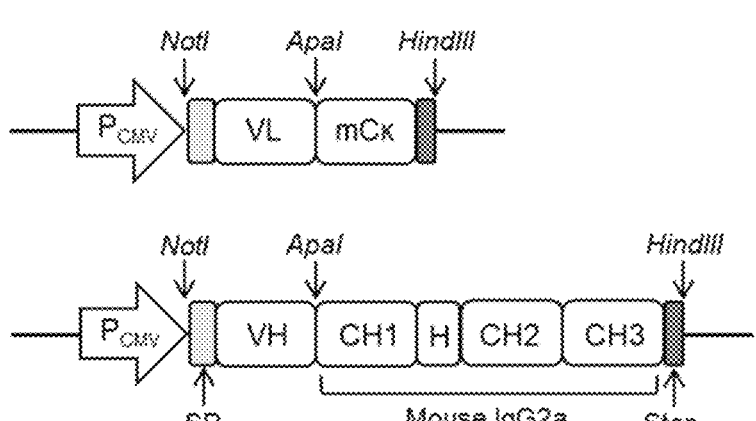
【Fig. 7b】
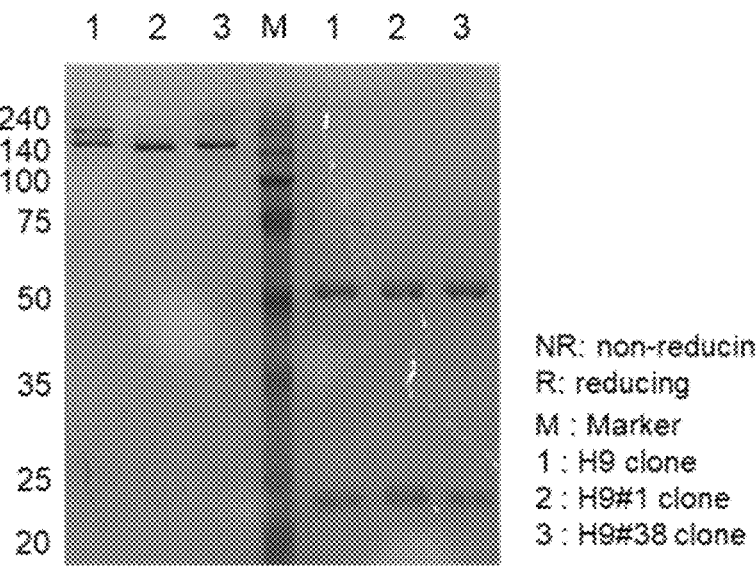
NR: non-reducing
R: reducing
M : Marker
1 : H9 clone
2 : H9#1 clone
3 : H9#38 clone 【Fig. 7c】
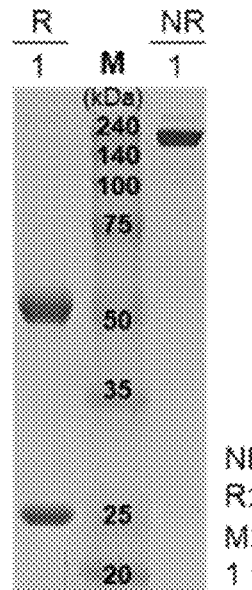
NR: non-reducing
R: reducing
M: Marker
1 : C 1-17
【Fig. 7d】
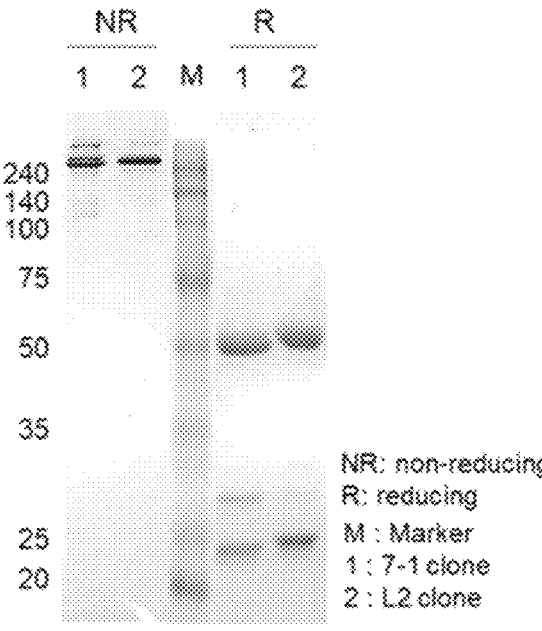
NR: non-reducing
R: reducing
M : Marker
1 : 7-1 clone
2 : L2 clone

[Fig. 8a]
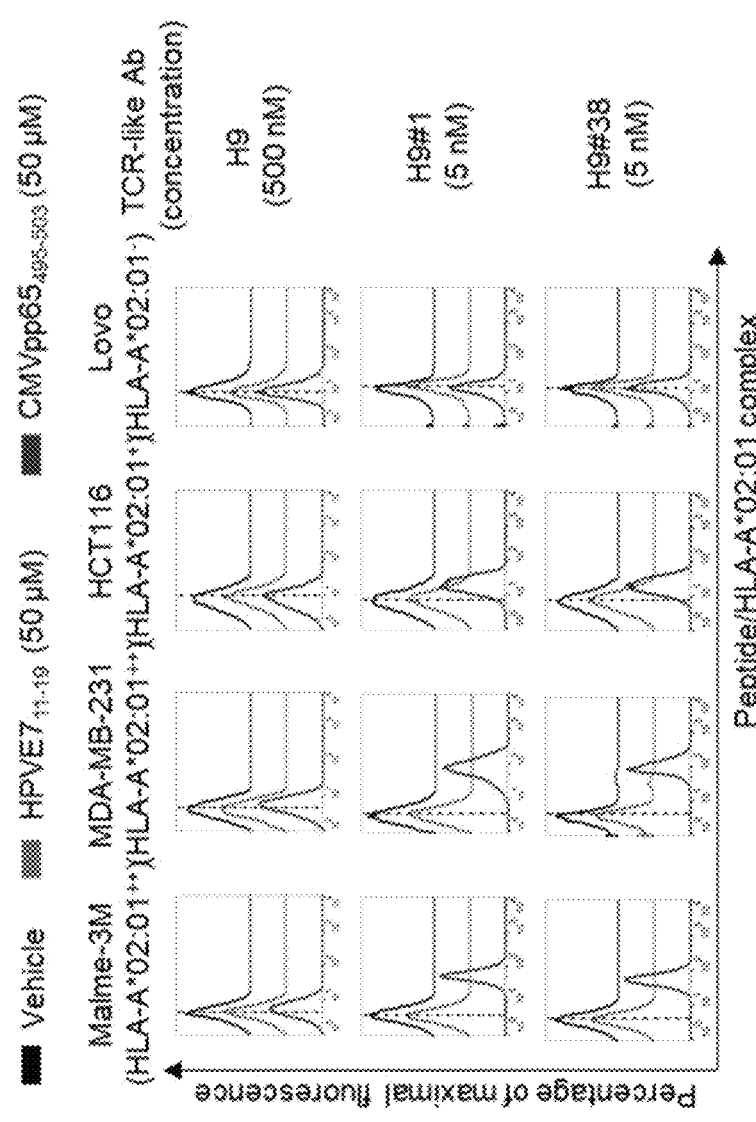

[Fig. 8b]
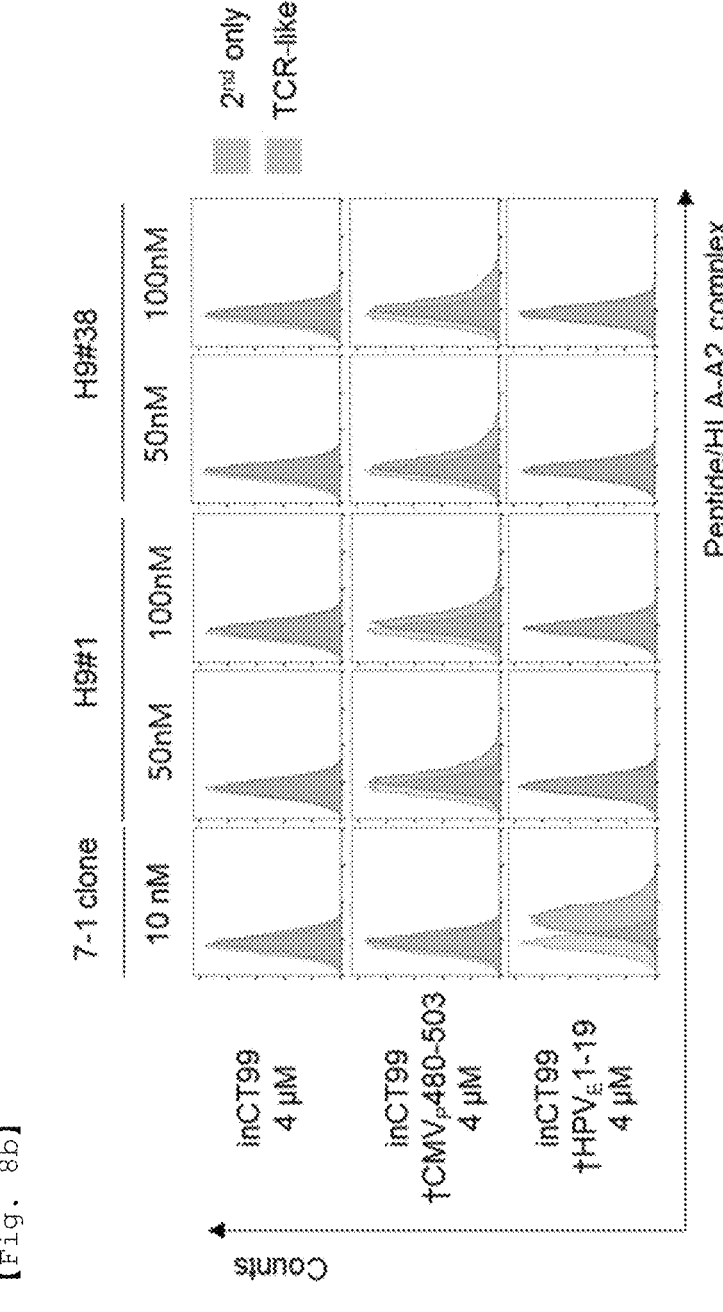

[Fig. 8c]
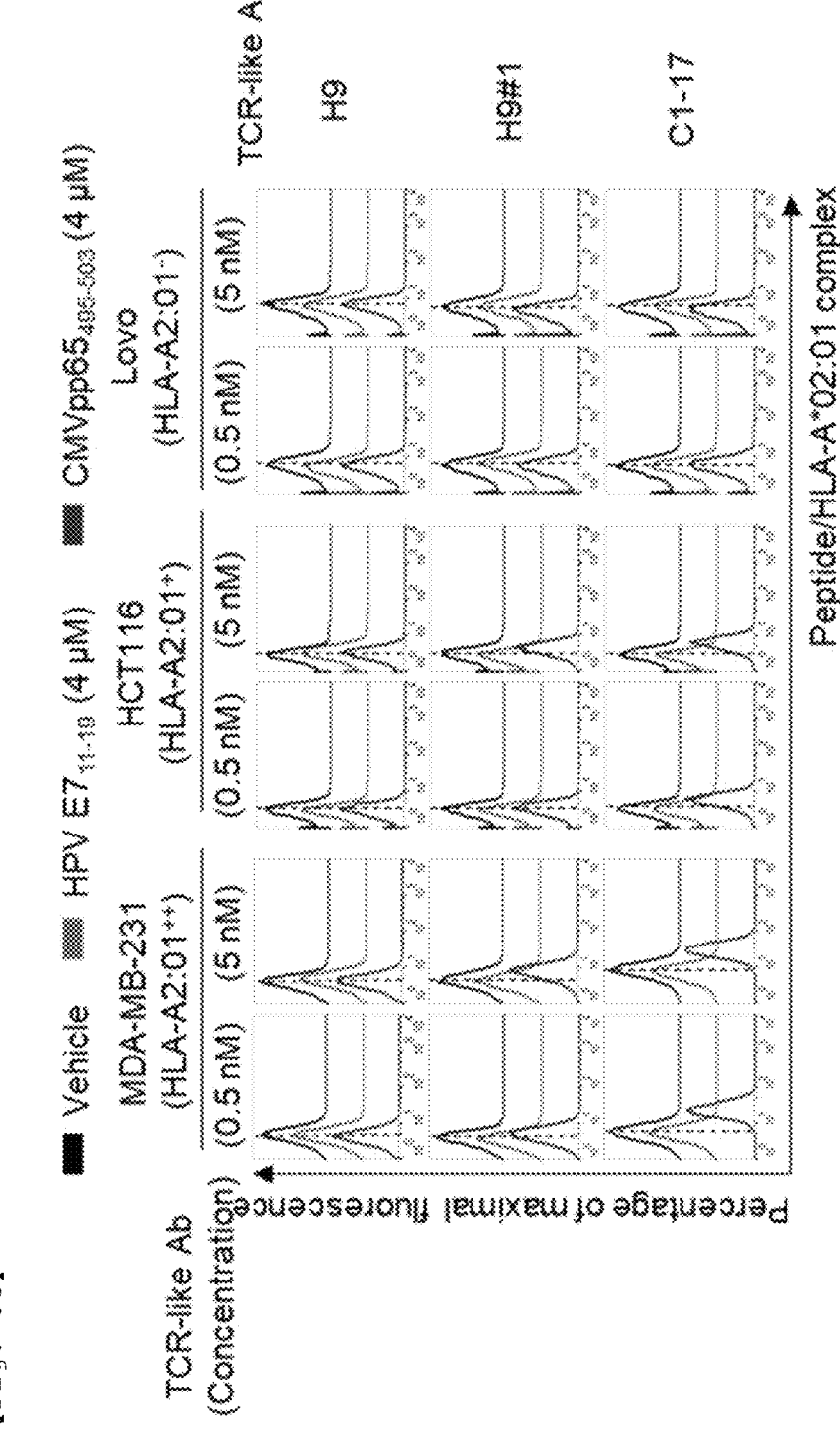

【Fig. 8d】
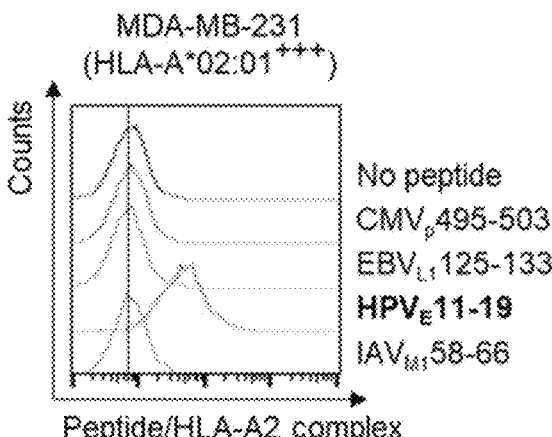
【Fig. 8e】
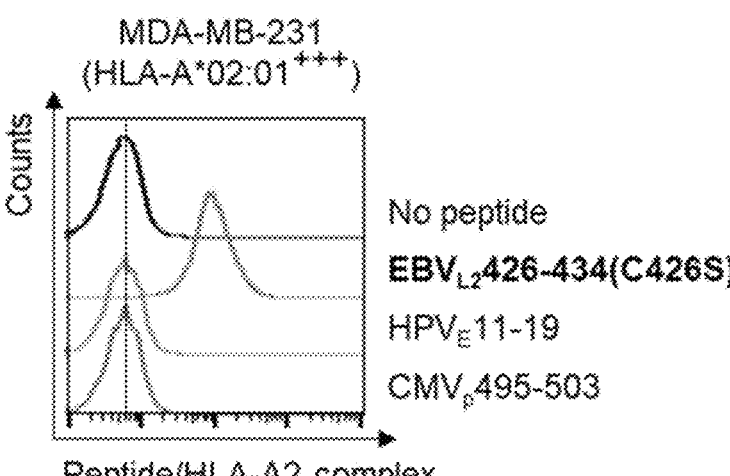

【Fig. 9a】
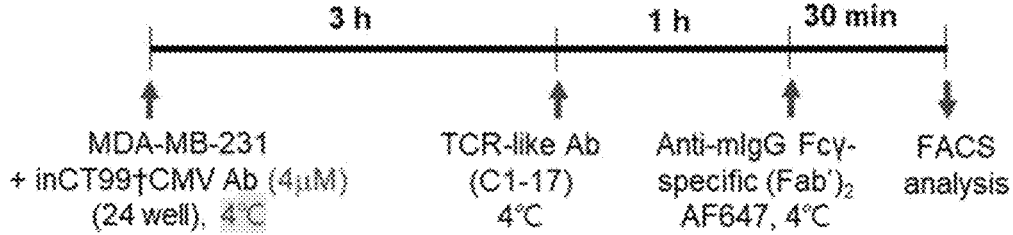
【Fig. 9b】
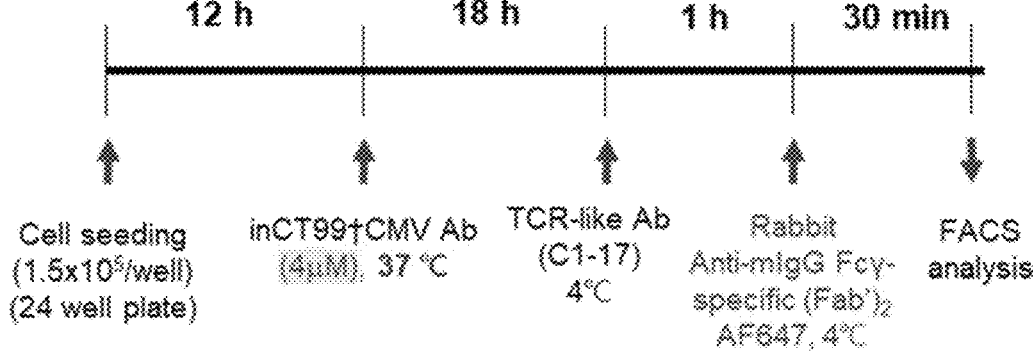

[Fig. 9c]
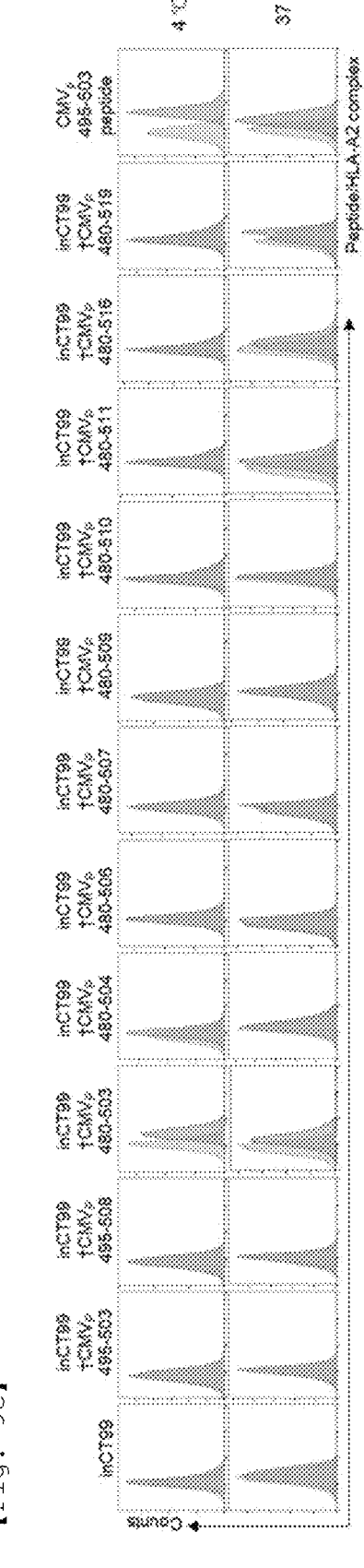
[Fig. 9d]
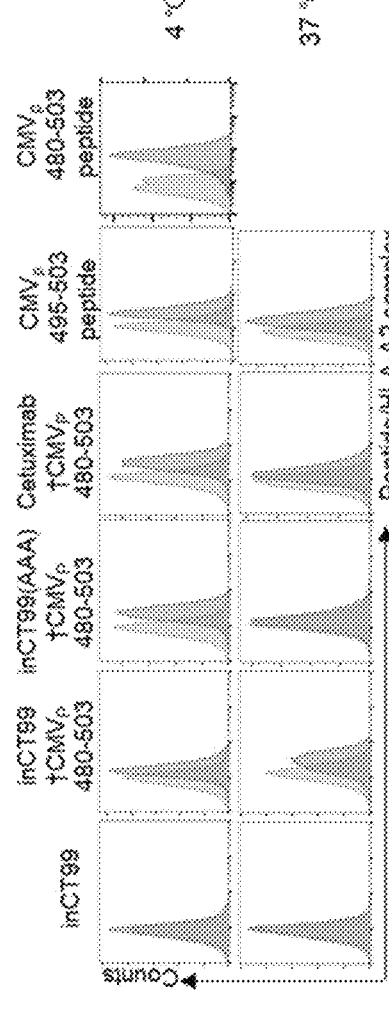

【Fig. 9e】
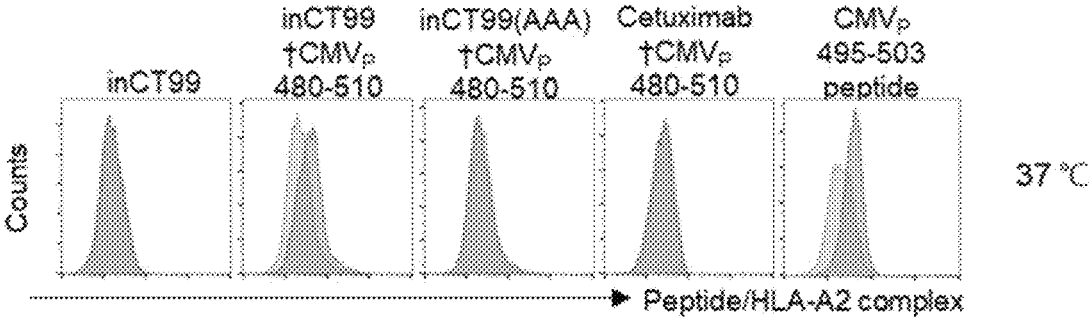
【Fig. 9f】
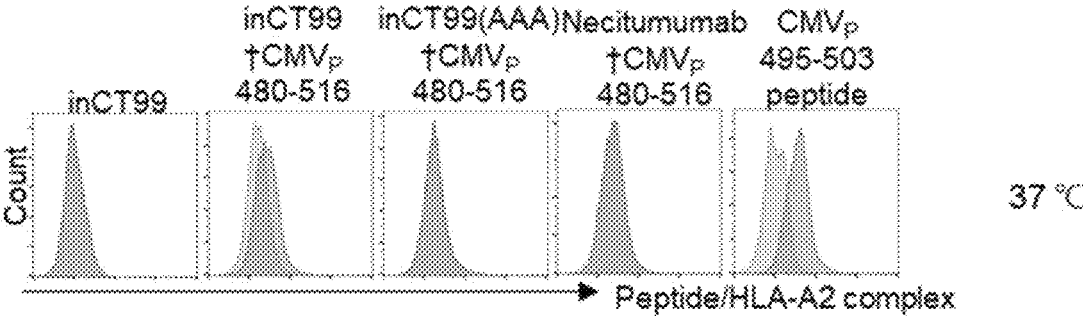
【Fig. 10a】
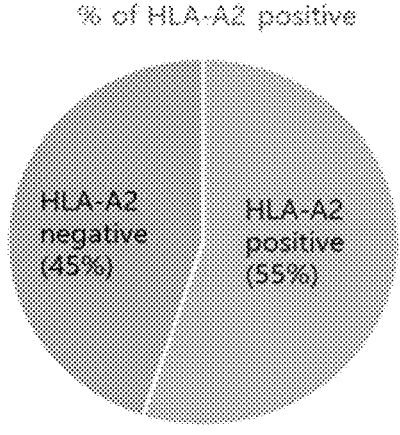

【Fig. 10b】
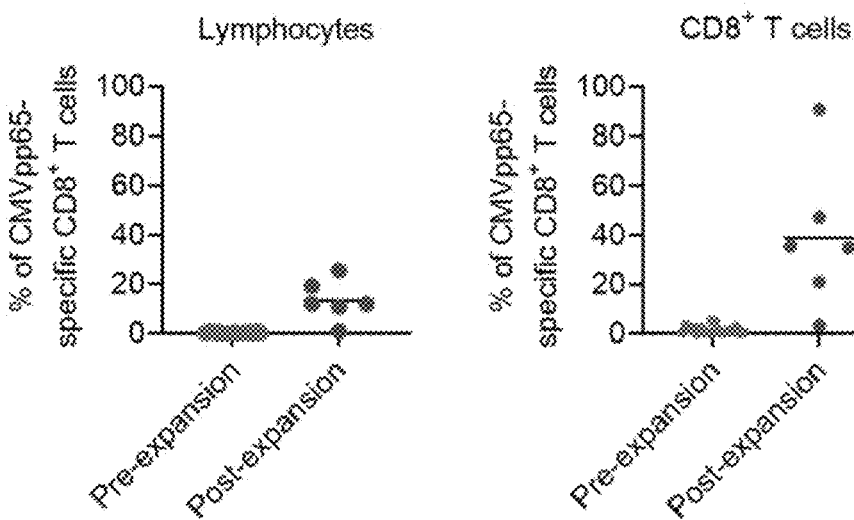
【Fig. 10c】
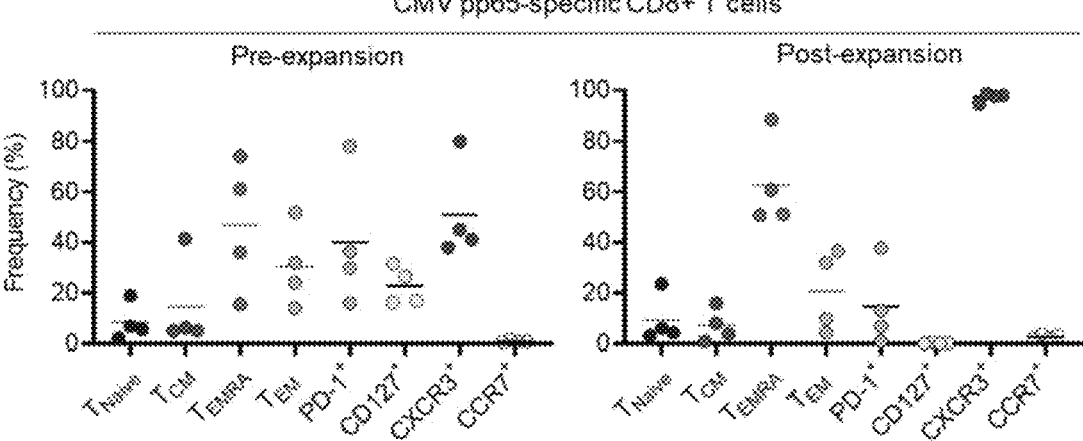

【Fig. 11a】
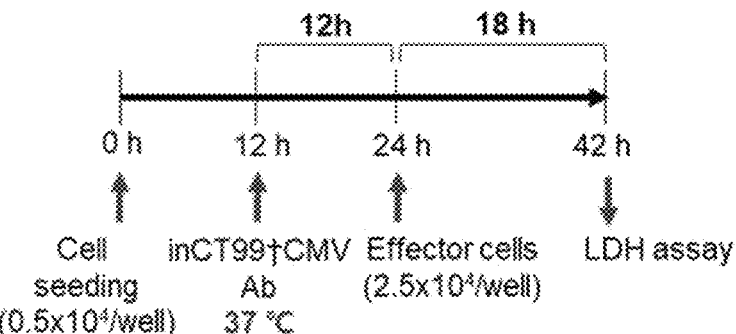
【Fig. 11b】
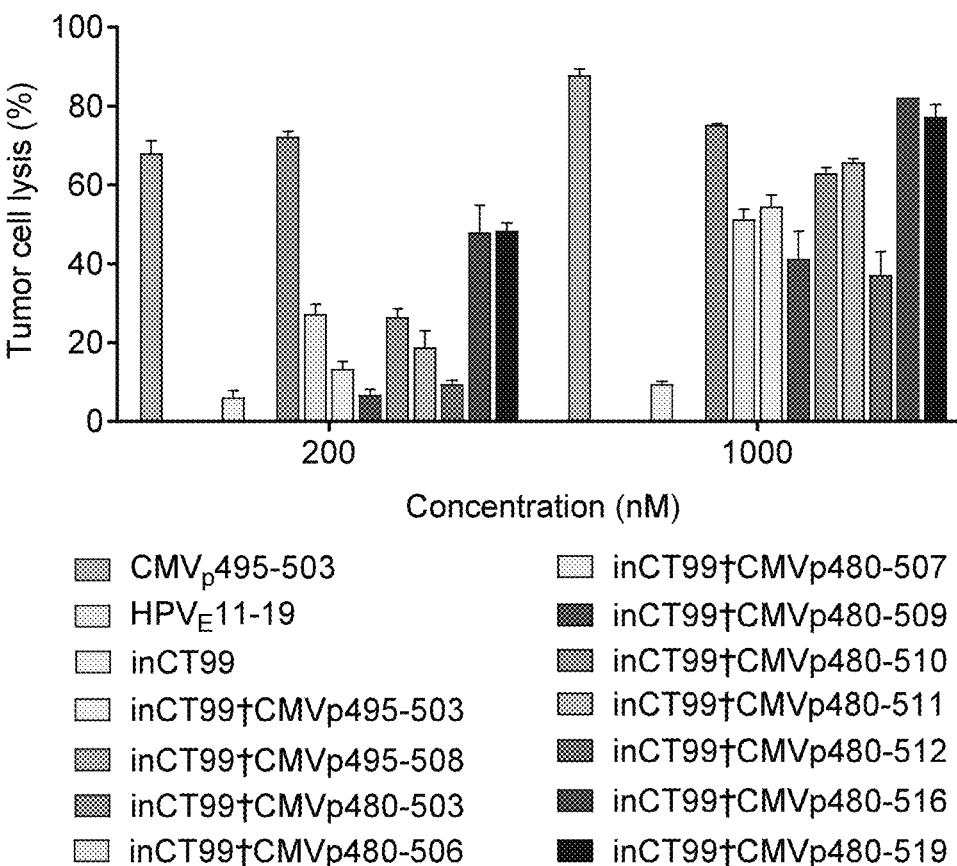

【Fig. 12a】
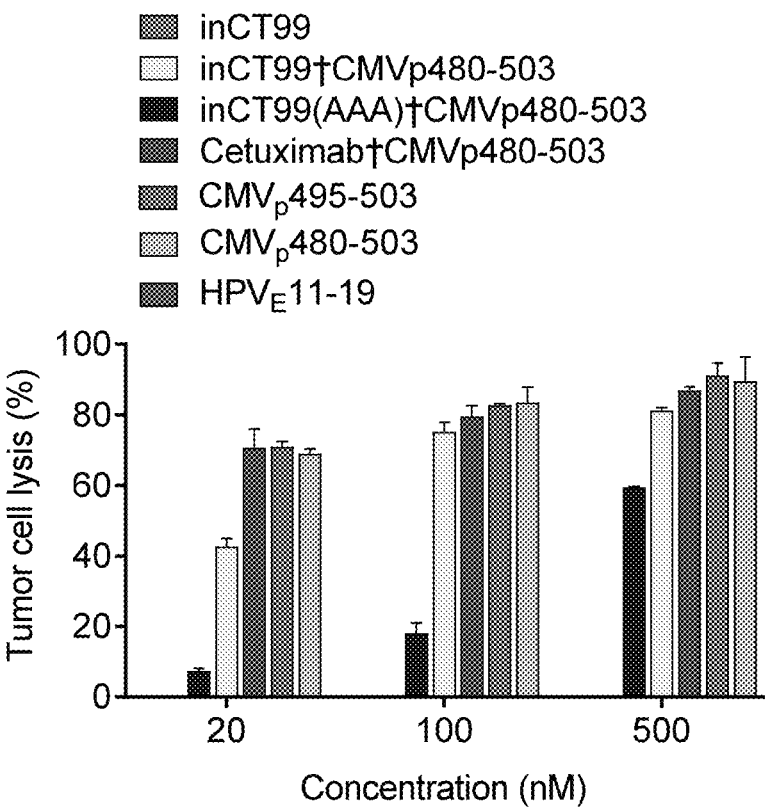
■ inCT99
▨ inCT99†CMVp480-503
■ inCT99(AAA)†CMVp480-503
▨ Cetuximab†CMVp480-503
▨ CMV_p495-503
▨ CMV_p480-503
▨ HPV_E11-19
【Fig. 12b】
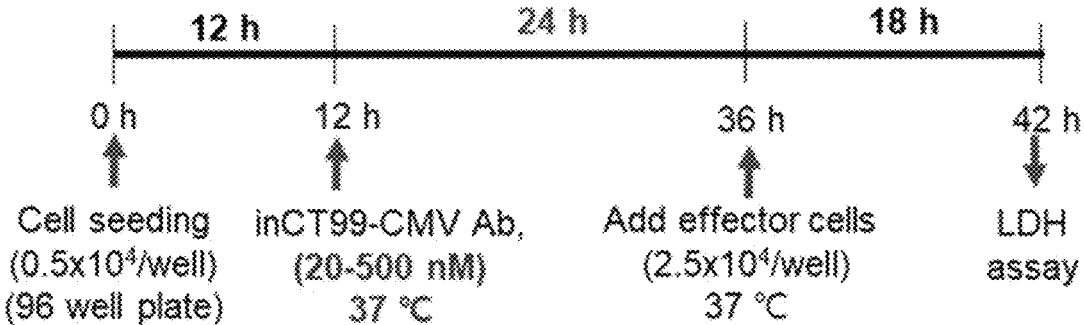

【Fig. 12c】
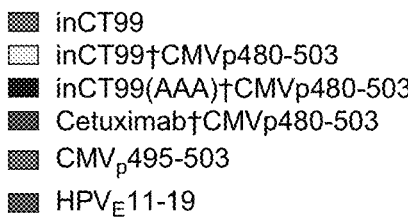
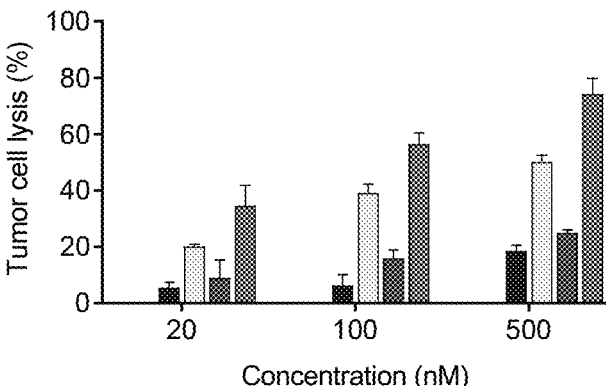
【Fig. 12d】
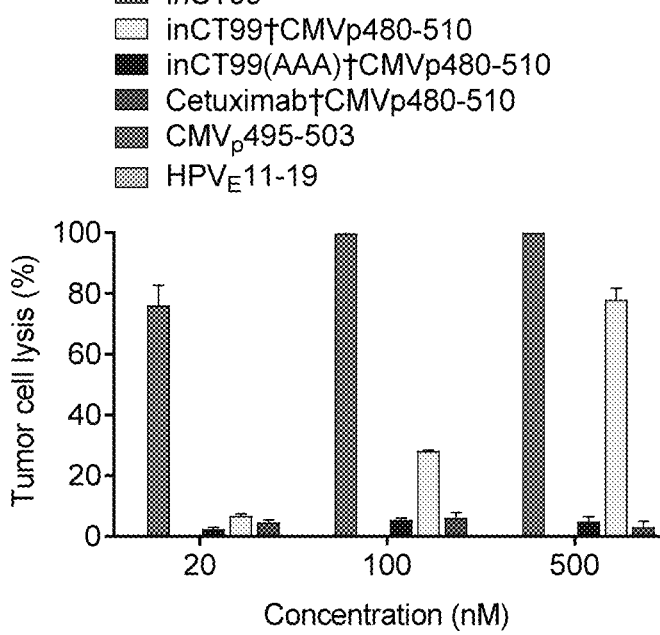

【Fig. 12e】
- ■ inCT99
- ■ Cetuximab†MMP14-CMVp495-503
- ■ inCT99†CMVp480-516
- ■ inCT99(AAA)†CMVp480-516
- ▨ Necitumumab†CMVp480-516
- ▢ CMV$_p$495-503
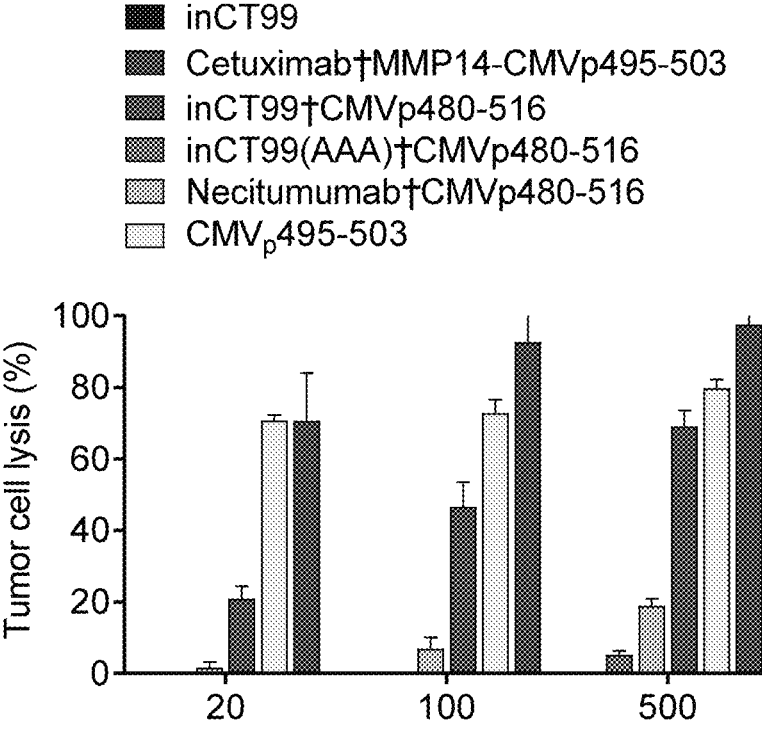
【Fig. 13a】
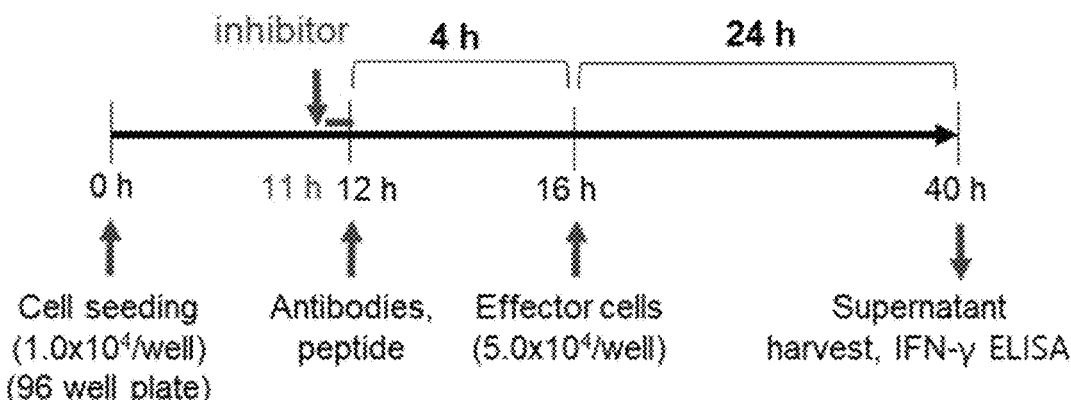

【Fig. 13b】
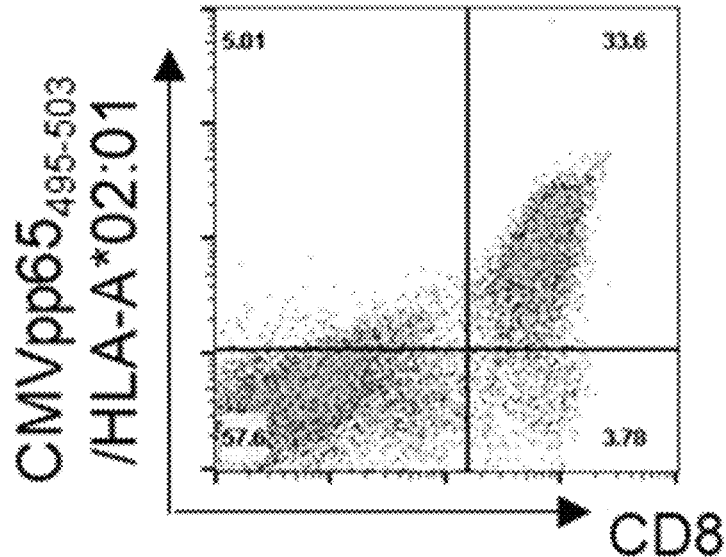
【Fig. 13c】
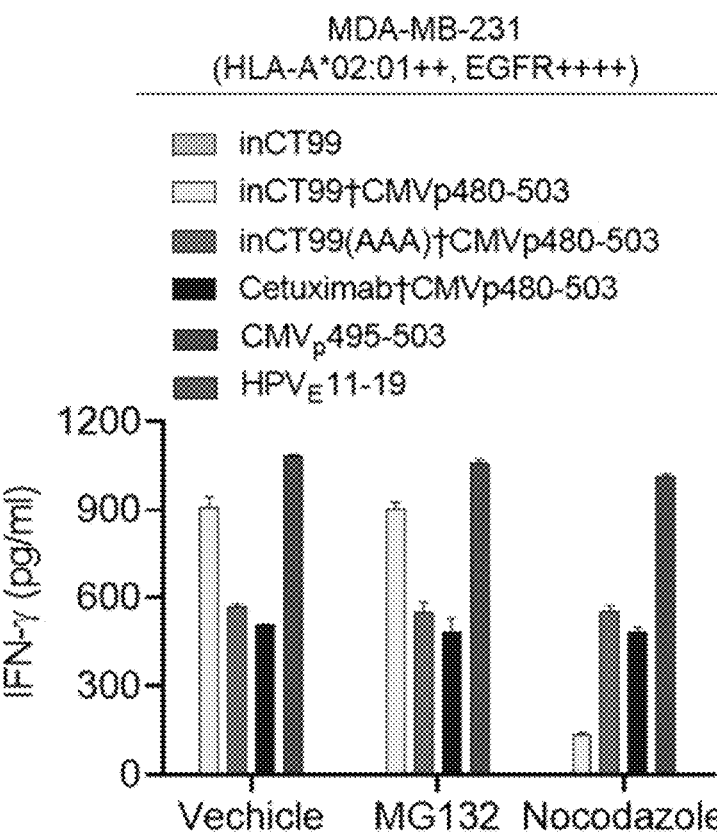

【Fig. 13d】
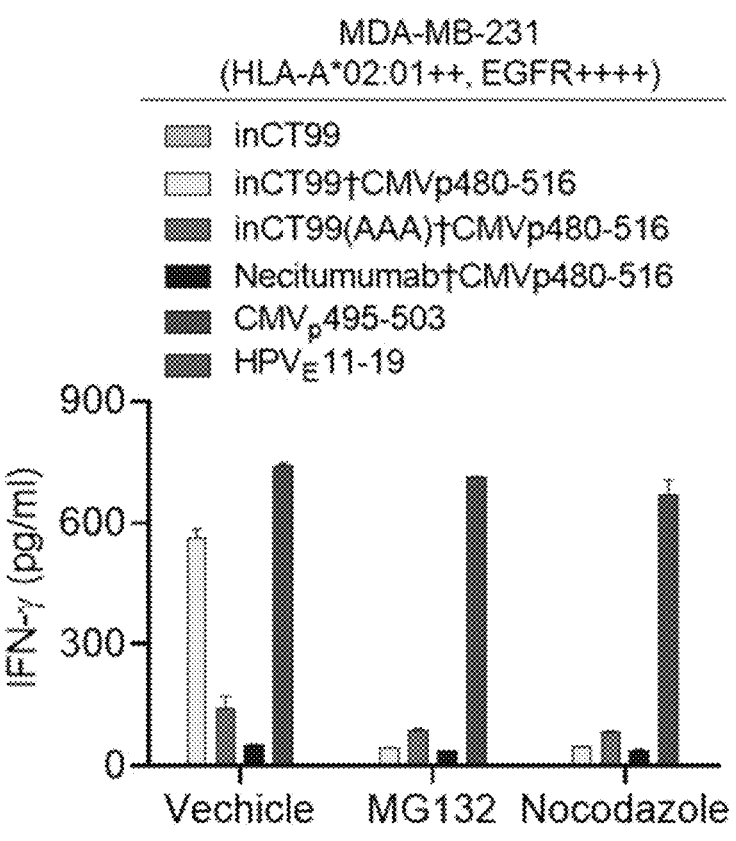

[Fig. 14a]

【Fig. 14b】
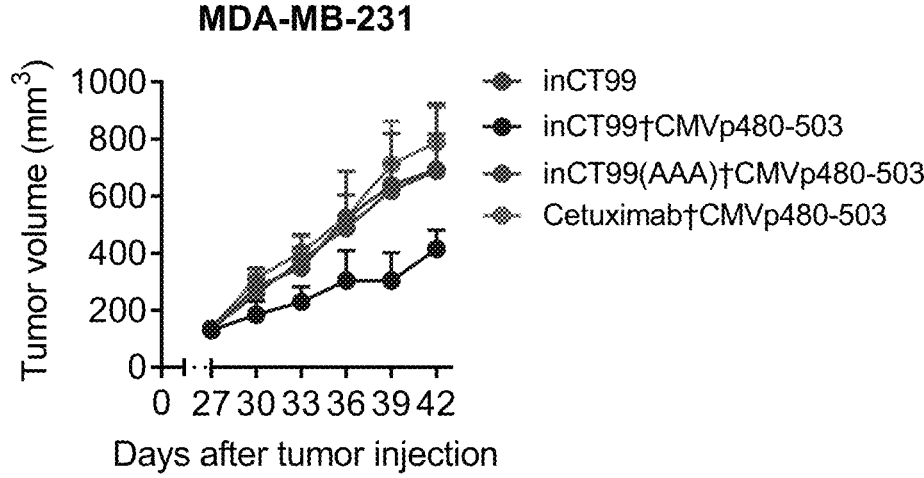
【Fig. 14c】
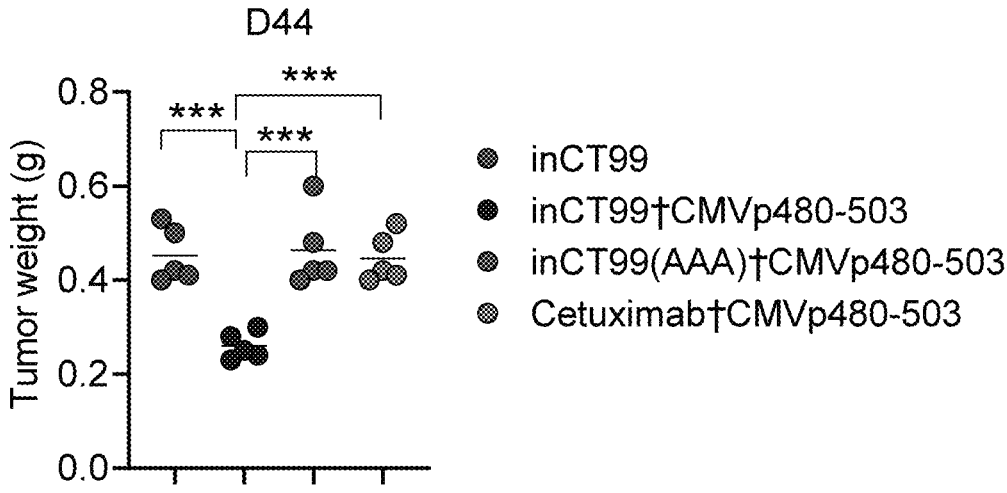
【Fig. 14d】
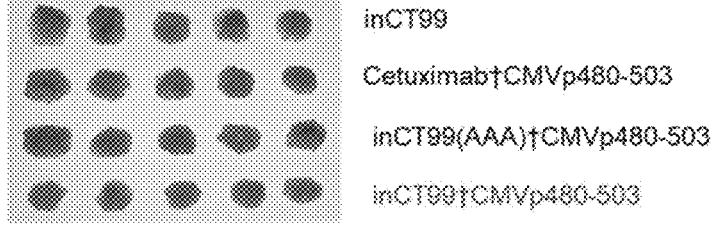

【Fig. 14e】
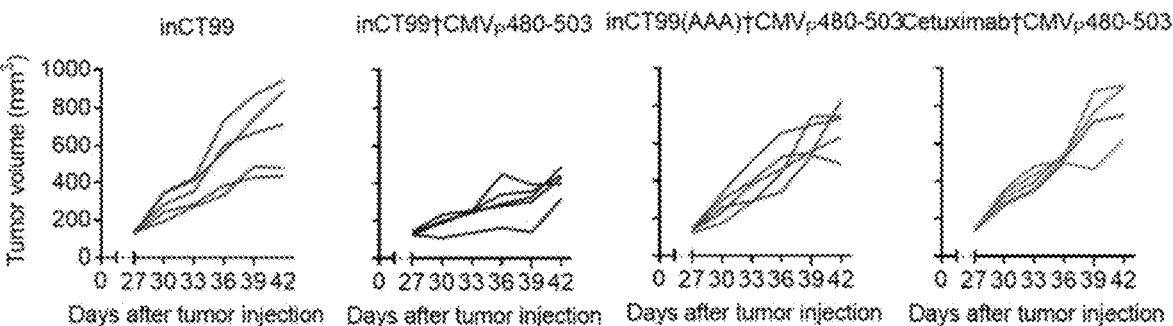
【Fig. 15a】
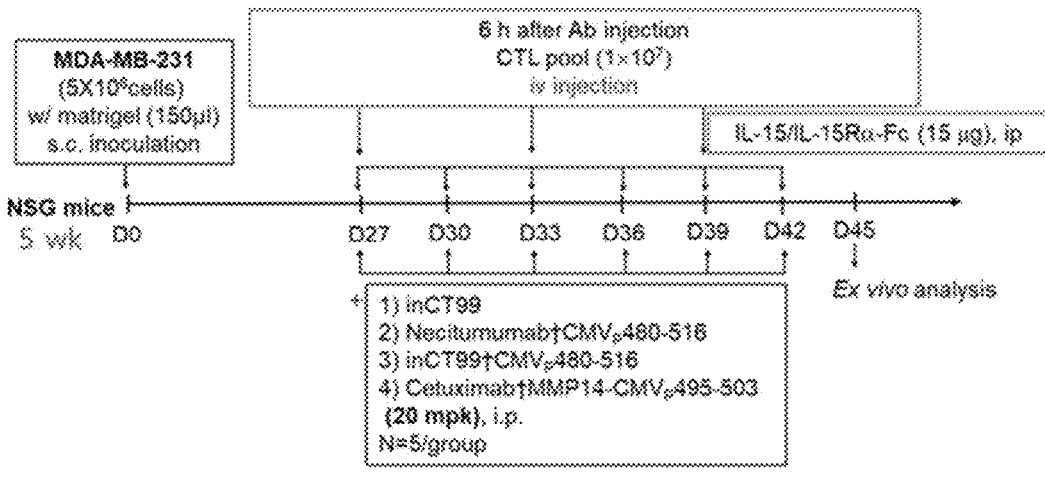
【Fig. 15b】
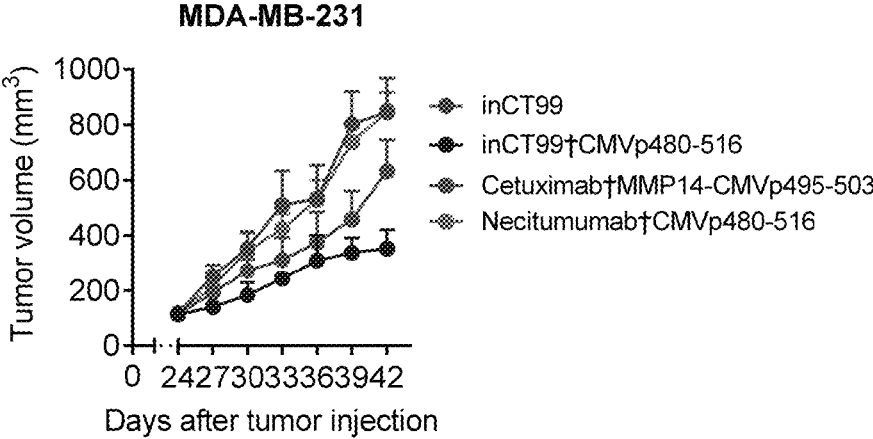

【Fig. 15c】
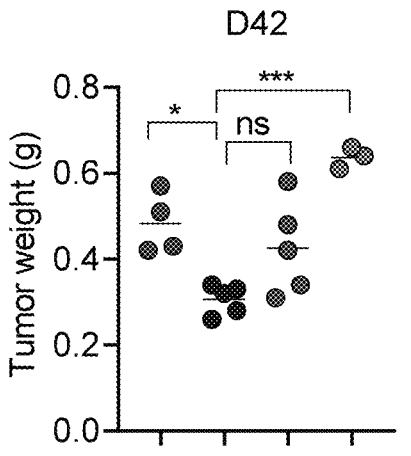
D42
- inCT99
- inCT99†CMVp480-516
- Cetuximab†MMP14-CMVp480-503
- Necitumumab†CMVp480-516
【Fig. 15d】
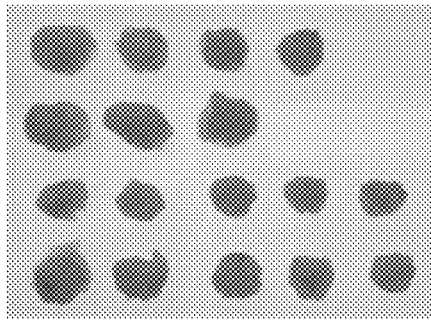
inCT99
Necitumumab†CMVp480-516
inCT99†CMVp480-516
Cetuximab†MMP14-CMVp495-503

[Fig. 15e]
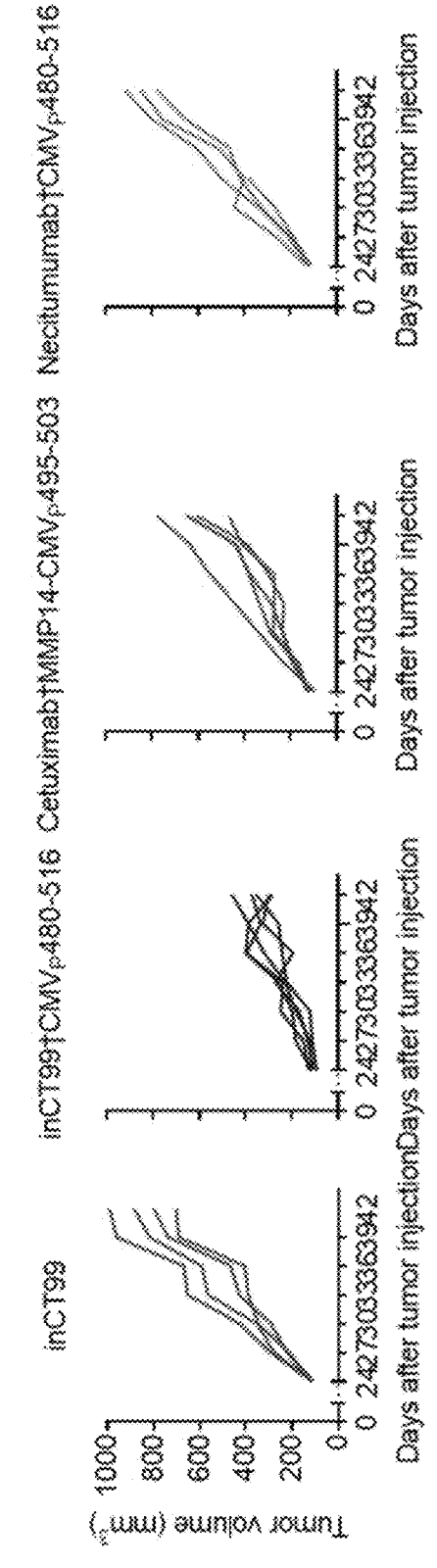
[Fig. 16a]
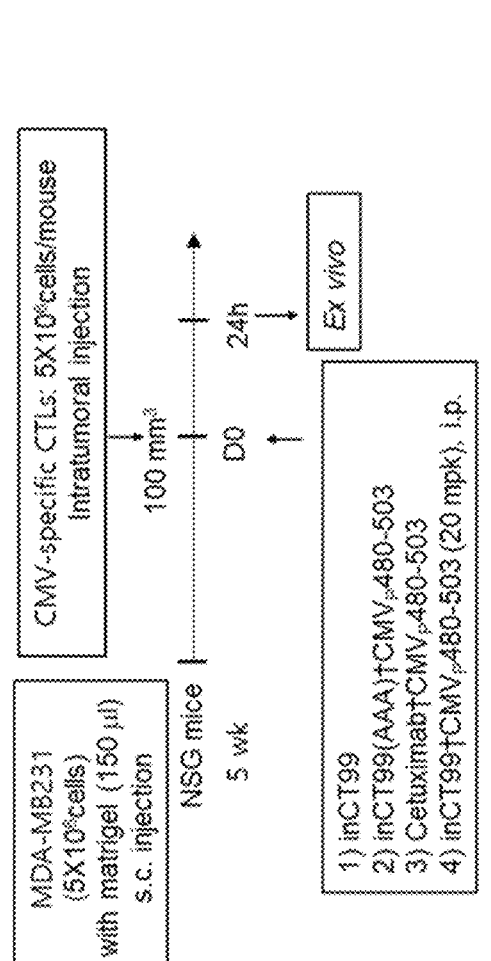

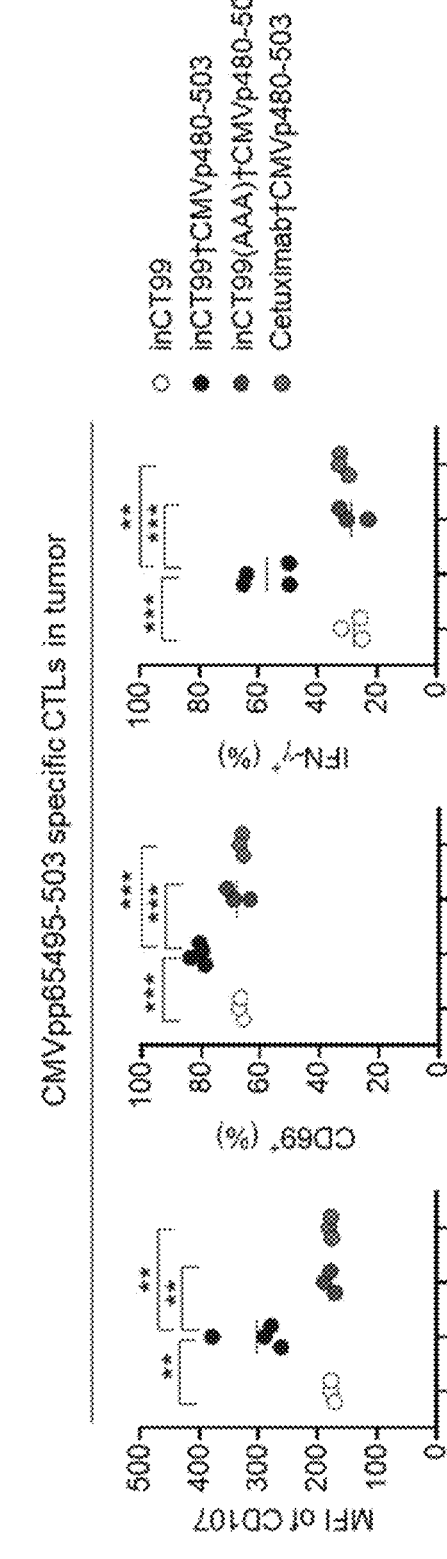
[Fig. 16b]
[Fig. 16c]

【Fig. 17a】
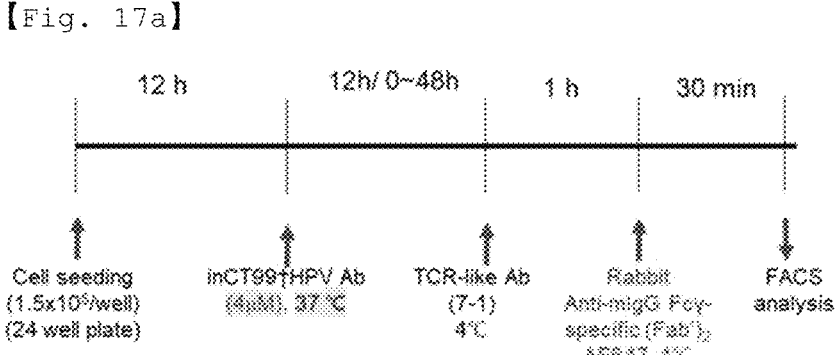
【Fig. 17b】
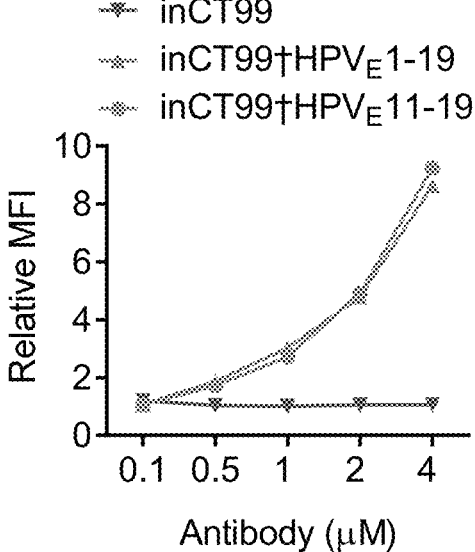

【Fig. 17c】
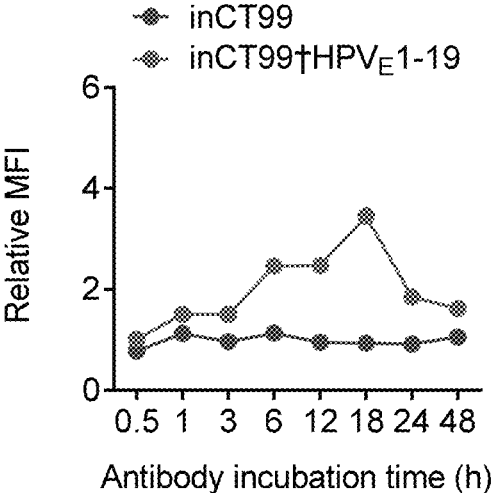
【Fig. 18a】
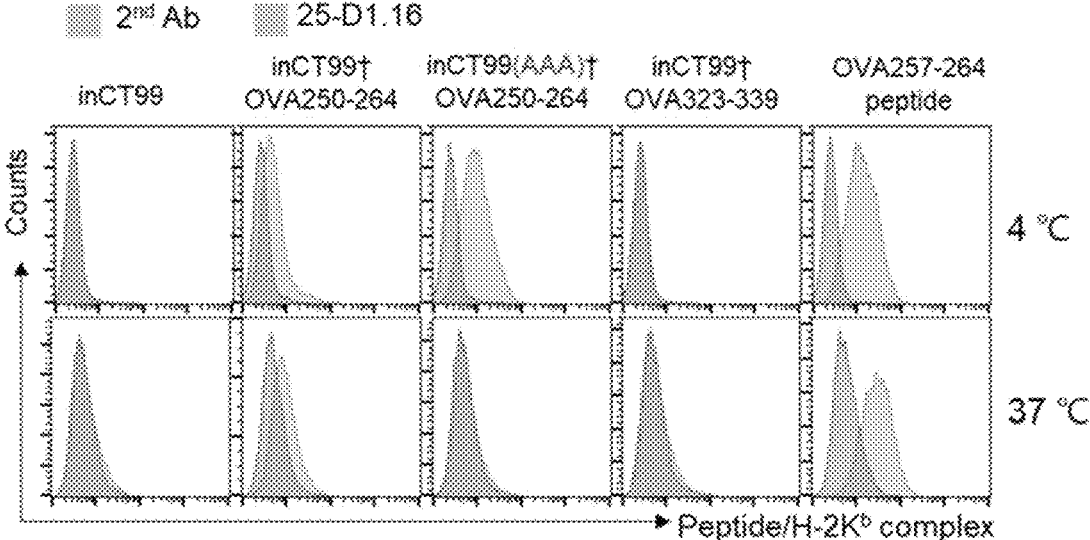

【Fig. 18b】
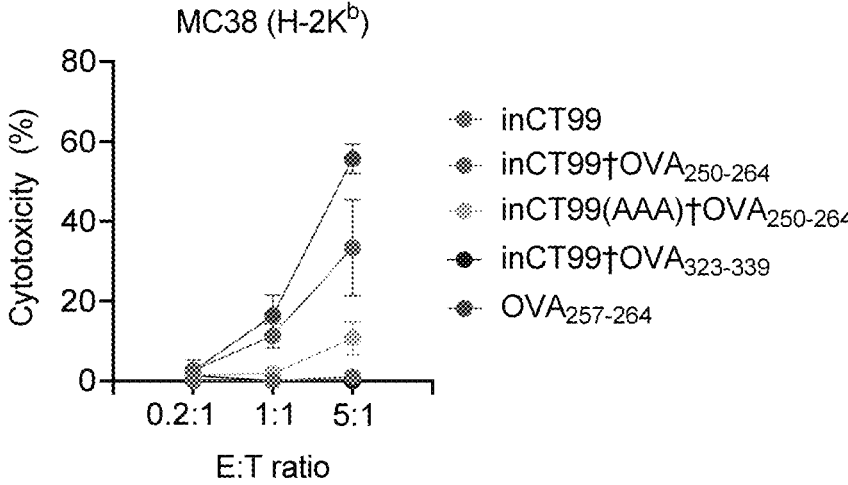
【Fig. 19a】
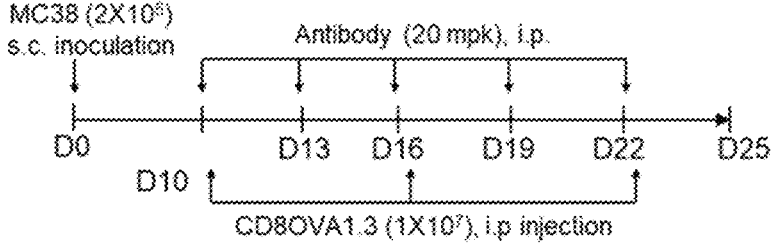
【Fig. 19b】
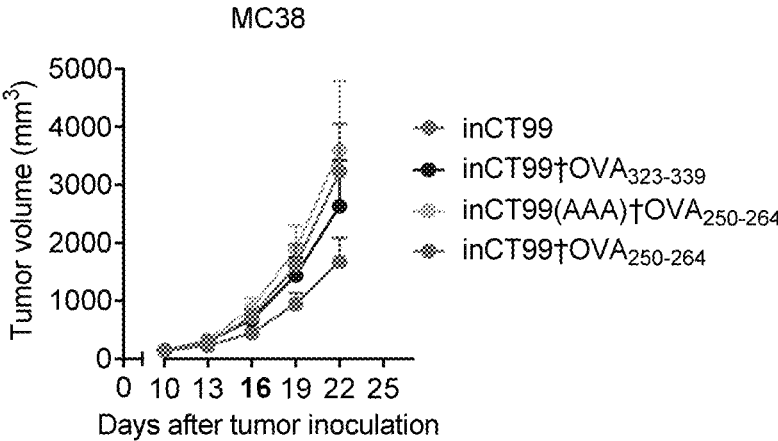

[Fig. 19c]
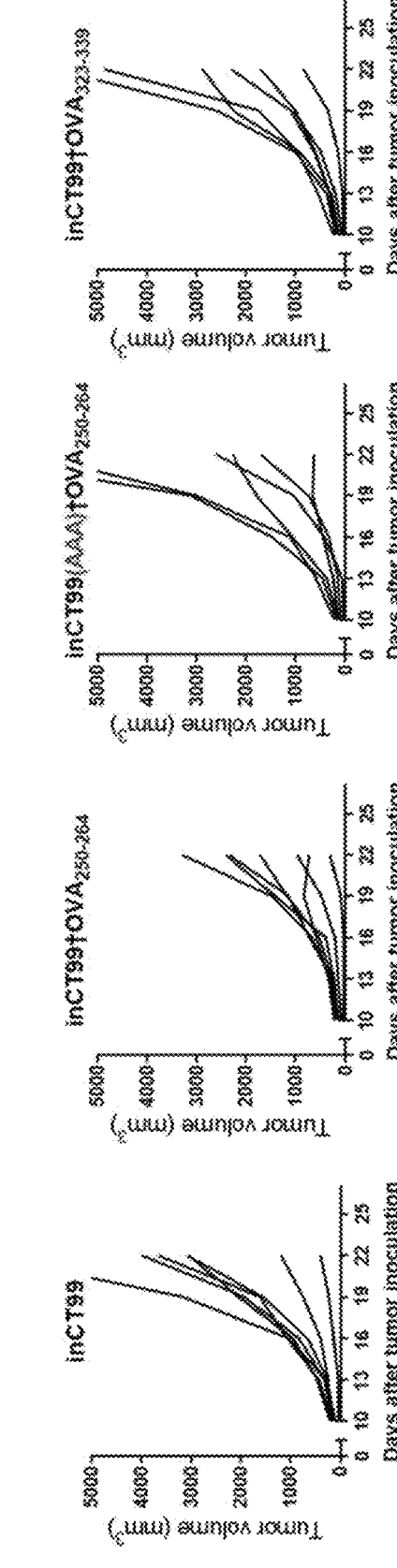

[Fig. 20]
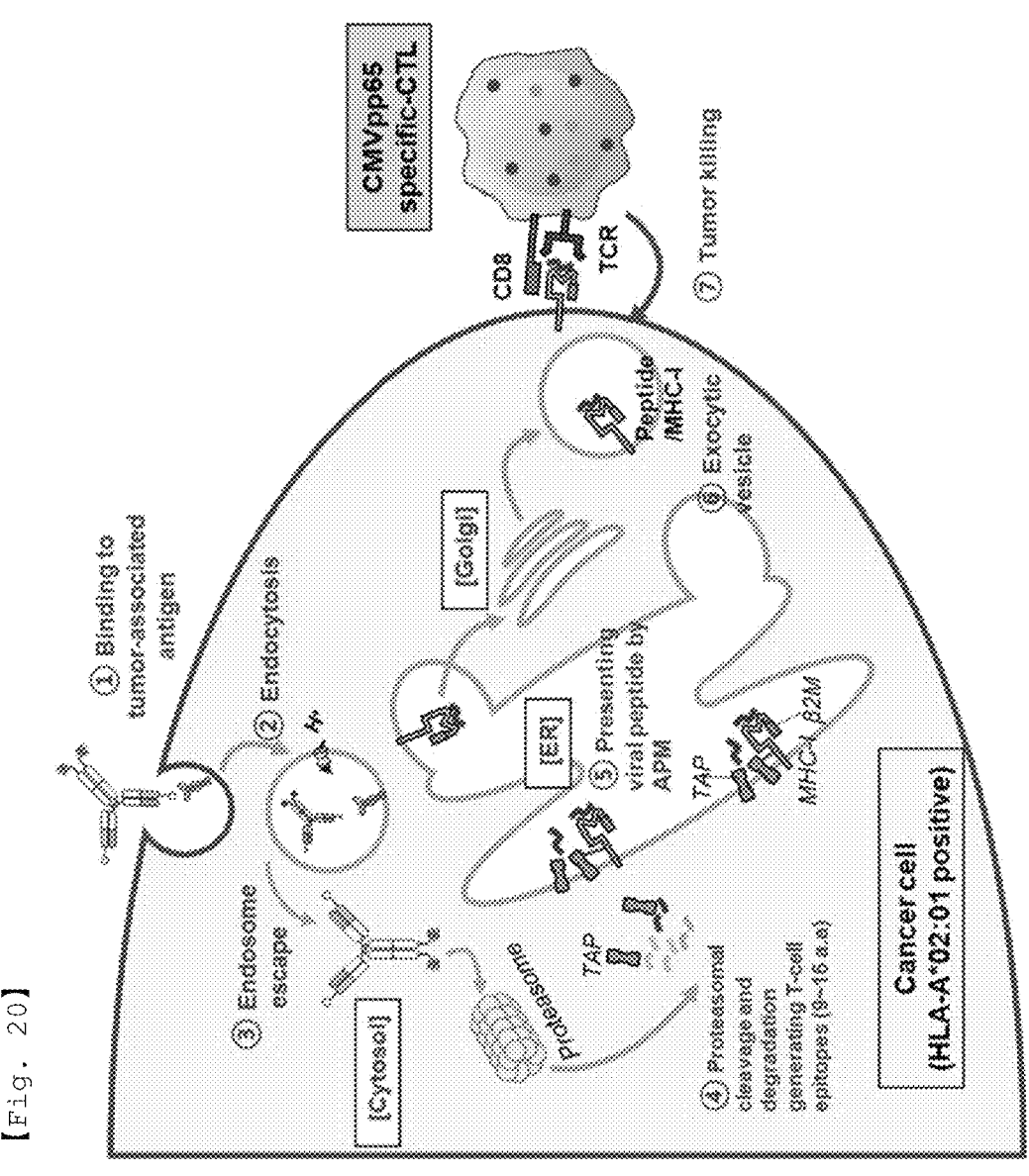

FUSION ANTIBODY FOR PRESENTING ANTIGEN-DERIVED T CELL ANTIGEN EPITOPE OR PEPTIDE CONTAINING SAME ON CELL SURFACE, AND COMPOSITION COMPRISING SAME

CROSS REFERENCE TO RELATED APPLICATIONS

THIS APPLICATION IS A NATIONAL STAGE OF INTERNATIONAL APPLICATION NO. PCT/KR2021/001571 FILED ON Feb. 5, 2021, CLAIMING PRIORITY BASED ON KOREAN PATENT APPLICATION NO. 10-2020-0014468 FILED ON Feb. 6, 2020.

INCORPORATION BY REFERENCE OF SEQUENCE LISTING

The instant application contains a sequence listing which has been filed electronically in txt format and is hereby incorporated by reference in its entirety. Said txt copy, created on Aug. 15, 2025, is named Q278251SequenceListingST25inresponseto815Notice.txt and is 42,298 bytes in size.

TECHNICAL FIELD

The present invention relates to a fusion antibody capable of displaying a CD8$^+$ T-cell antigen epitope to an antigen-presenting molecule MHC-I (major histocompatibility complex class I) on the surface of a target cell by delivering an antigen-derived CD8$^+$ T-cell antigen epitope or a peptide comprising the same to the cytosol of the target cell, a composition including the same, and the use thereof.

More particularly, the present invention relates to a fusion antibody in which an antigen-derived CD8$^+$ T-cell antigen epitope or a peptide comprising the same is genetically fused to a cellular cytosol-penetrating antibody (cytotransmab) having cell- or tissue-specific cytosol-penetrating ability, and a composition including the same. Here, the fusion antibody is capable of displaying the T-cell antigen epitope to the antigen-presenting molecule MHC-I on the surface of the target cell by being delivered to the cytosol of the target cell.

The antigen-derived CD8$^+$ T-cell antigen epitope includes a protein antigen that is a cause of diseases such as cancer, autoimmune diseases, and the like, but is preferably derived from an antigen of virus that may cause infection in humans.

The present invention relates to a fusion antibody capable of presenting the antigen-derived T-cell antigen epitope on the surface of a target cell to thus kill target cells by cytotoxic T cells (cytotoxic CD8$^+$ T cells, CTLs) that specifically recognize a peptide-MHC-I complex, and a composition thereof.

Specifically, when the antigen of virus-derived CD8$^+$ T-cell antigen epitope is delivered to the cytosol of cancer cells through the fusion antibody of the present invention and the viral peptide-MHC-I complex is expressed on the surface of cancer cells and thus the cancer cells are recognized as virus-infected cells, anti-viral cytotoxic T cells circulating in the cancer patient's body recognize the cancer cells as virus-infected cells and thus kill the cancer cells, whereby the fusion antibody is ultimately used for the purpose of eliminating cancer.

BACKGROUND ART

A major histocompatibility complex (MHC) is a set of genes encoding cell-surface proteins for recognizing foreign molecules in vertebrates, and acts as an antigen-presenting molecule that recognizes the target material of an immune response as a T-cell antigen. MHCs are broadly divided into two types: type-I MHC (MHC class I molecules, MHC-I) and type-II MHC (MHC class II molecules, MHC-II). Human MHC-II is a heterodimer structure composed of an alpha chain ($\alpha$-chain) and a beta chain ($\beta$-chain). Human MHC-I is a heterodimer structure of human leukocyte antigen (HLA) and beta-2-microglobulin ($\beta$2m). Human MHC-I has three types of genes, namely HLA-A, HLA-B, and HLA-C, and is expressed in all cells having a nucleus, including tumor cells. Antigens presented by MHC-I react with CD8$^+$ T cells. MHC-II has genes of HLA-DP, HLA-DQ, and HLA-DR, and proteins are expressed only in antigen-presenting cells (APCs), such as dendritic cells (DCs), macrophages, and B cells. Antigens presented by MHC-II react with CD4$^+$ T cells. The antigen-presenting cells express both MHC-I and MHC-II, whereas cells other than the antigen-presenting cells express only MHC-I.

In an adaptive immune response, antigens are recognized by receptor molecules (immunoglobulin) on B cells and by T-cell receptors (TCRs) on T cells. Unlike B cells, T cells are able to recognize an antigen epitope peptide only when an antigen is presented in the form of a peptide bound to MHC, namely a peptide-MHC complex. This antigen recognition by T cells is called MHC-restricted antigen recognition (MHC restriction). CD4$^+$ T cells react with antigen-presenting cells presenting the peptide-MHC-II complex, and CD8$^+$ T cells react with cells presenting the peptide-MHC-I complex.

Tumor- and virus-infected cells present T-cell antigen peptides (8-11 amino acid residues) called peptide-MHC-I complexes via cell-surface MHC-I molecules with respect to CD8$^+$ cytotoxic T lymphocytes (CTLs). CD8$^+$ cytotoxic T cells enable recognition and binding through a T-cell receptor (TCR) specific to the peptide-MHC-I complex, and secrete effector materials to thus kill target cells. In the case of virus-infected cells or tumor cells, antigen proteins are translated and exist in the cells. These antigens are subjected to intracellular antigen processing, and particularly, they are degraded into small peptides in the proteasome within the cytosol and then selectively enter the endoplasmic reticulum by TAP (transporter associated with antigen processing) proteins present on the surface of the endoplasmic reticulum (ER). Meanwhile, $\alpha$-chain mRNA of MHC-I enters the endoplasmic reticulum at the time of translation in the ribosome of the endoplasmic reticulum, and binds to the membrane of the endoplasmic reticulum. The membrane-bound $\alpha$-chain protein binds to a $\beta$-2-microglobulin protein in the endoplasmic reticulum, where it is able to bind to a peptide epitope. Thereafter, the peptide-MHC-I complex is transported to the cell membrane through the Golgi apparatus to present the complex on the cell surface, and this complex is recognized by the TCR of CD8$^+$ T cells. Thereby, a cell-mediated immune response in which antigen-bearing cells are killed by cytotoxic T cells is induced.

MHC class II (MHC-II) molecules are expressed on antigen-presenting cells such as B cells, macrophages, dendritic cells, and endothelial cells during phenomena such as inflammation or the like. MHC-II molecules on the surface of antigen-presenting cells typically present antigen-derived peptides to CD4$^+$ T cells in intracellular vesicles. Antigens present in extracellular tissue or blood are processed by cells expressing MHC-II molecules and recognized by CD4$^+$ helper T cells. Antigens enter phagocytes through phagocytosis and endocytosis, and the incoming proteins are degraded into small peptides in the endosome within the cells. Meanwhile, both α-chain and β-chain proteins of MHC-II are expressed and form a complex in the state of binding to the membrane of the endoplasmic reticulum. In the endoplasmic reticulum, an invariant-chain (Ii chain) protein additionally binds to the peptide-binding site in this complex, and thus the MHC-II molecule in the endoplasmic reticulum does not bind to the peptide epitope that binds to the MHC-I molecule. MHC-II molecules to which peptides do not bind are fused with endocytic vesicles containing peptide fragments during transport to the cell membrane, where the invariant chains are dissociated and bind to antigen-derived peptides. These peptide-MHC-II complexes are transported to the cell surface to thus present antigens to CD4$^+$ T cells, whereby humoral immune responses such as antibody production are induced. The antibody thus produced eventually binds to the antigen existing outside the cell and removes the antigen.

Among antigen-presenting cells, dendritic cells capture antigens through phagocytosis and receptor-mediated endocytosis when immature, process the antigens, and then present antigen-derived peptides to MHC molecules to induce recognition of T cells. During antigen processing, the dendritic cells become mature and migrate to the surrounding lymph nodes to thus present antigens to naive T cells. T-cell activation requires not only antigen presentation by dendritic cells, but also stimulation of co-stimulatory molecules (CD80, CD86, CD40, etc.) expressed on the surface of mature dendritic cells, cell adhesion molecules, and pro-inflammatory cytokines. Through these signals, the dendritic cells induce differentiation of CD4$^+$ T cells into T helper 1 (Th1) cells and also activate CD8$^+$ T cells. However, CD4$^+$ T cells are differentiated into Th2 cells or regulatory T cells (Tregs) without stimulation of co-stimulatory factors of antigen-presenting cells and pro-inflammatory cytokines or with stimulation of immunosuppressive cytokines.

Moreover, dendritic cells originally bind to MHC-II and present, on the cell surface, peptides derived from exogenous proteins that activate CD4$^+$ T cells, but have the ability to present such peptides through MHC-I, which is called cross-presentation. Thus, CD8$^+$ T cells are also capable of cross-priming. Therefore, dendritic cells are regarded as the most potent antigen-presenting cells known to date.

As recent cancer immunotherapy, there has been an attempt to eliminate cancer cells by activating cytotoxic CD8$^+$ T cells (CTLs) through administration of a cancer antigen to a patient, which is called a therapeutic cancer vaccine. Such a therapeutic cancer vaccine is used to confer immunogenicity to a tumor having reduced immunogenicity or to induce the activity of tumor-specific T cells. In general, a process of recognizing cancer cells by the immune system is required in order for an anti-tumor immune response to occur. When a cancer-antigen-derived peptide is presented to an antigen-presenting molecule (major histocompatibility complex class I, MHC-I) on the surface of cancer cells, cytotoxic T lymphocytes (CTLs) having a T-cell receptor (TCR) that is able to specifically bind to this complex recognize cancer cells and induce cancer cell death.

To date, most cancer vaccines have been developed through methods that directly use the corresponding cancer cells. For example, in the initial stage of cell-based cancer vaccine development, inactivated whole cancer cells or cancer cell lysates mixed with an adjuvant have been used. Since then, improved cancer vaccines have replaced existing vaccines, which apply genes encoding cytokines and co-stimulatory molecules. Recent cancer vaccines may be classified into DNA vaccines, peptide vaccines, tumor cell vaccines, vaccines using bacteria- or virus-derived vectors, and dendritic cell vaccines depending on the antigen type and the antigen delivery method.

DNA vaccines initially induce an immune response to a desired extent, but the efficacy of the vaccine decreases over time. This is because the antibody to the administered vaccine gradually obtains affinity, and eventually an immune response is induced and the administered DNA vaccine is destroyed.

As a method of presenting antigens to dendritic cells, co-culture with peptides, proteins, and autologous/allogeneic cancer cells is generally used. Short synthetic peptides (8-15 amino acid residues) bind directly to MHC molecules on the surface of dendritic cells, whereas long synthetic peptides (28-35 amino acid residues), proteins, and cancer cells have to be processed into peptides before binding to MHC molecules. In the case of a short synthetic peptide, a CD8$^+$ T-cell antigen epitope for a tumor-associated antigen (TAA) is being used in clinical trials. Here, the patient's HLA haplotype must be known, and the peptide must be capable of binding to a specific HLA haplotype. A long synthetic peptide may be cross-presented through antigen processing in dendritic cells, so it is able to induce not only CD4$^+$ T-cell responses but also CD8$^+$ T-cell responses, and has the advantage of being able to present the peptide for a longer period of time.

The use of whole tumors or lysates of tumor cell lines as cancer vaccines is also applied to various carcinomas. This method has major advantages in that (1) various epitopes may be presented on different haplotypes of MHC molecules, so CD4$^+$ T-cell and CD8$^+$ T-cell responses to various antigens may be induced, and (2) it is possible to continuously present antigen-derived epitopes through antigen processing. However, it is disadvantageous in that self-antigens may be presented and in that cancer cells are required to be isolated from the patient.

Bacterial or viral vectors are also used as cancer vaccines carrying antigens. Using such a vector, a gene encoding TAA may be inserted, a gene encoding a virulence- and replication-related protein may be removed in order to increase safety, or dendritic cell maturation may be induced. However, the patient genome must be integrated, and an immune response to the vector may be induced, which is undesirable.

Cancer-antigen-derived peptides that may be presented by cancer cells may be broadly classified into tumor-associated antigens (TAAs) and tumor-specific antigens (TSAs). TAA is an antigen overexpressed in tumor cells, such as EGFR, ERBB2, CD19, mesothelin, and the like, but is also expressed to some extent in normal cells or tissues. Also, oncofetal antigen such as CEA and cancer/testis antigen such as NY-ESO-1 are included. Since TSA is a mutant protein caused by genetic mutation of tumor cells or an oncogenic viral protein, it is a tumor-specific protein (KRAS mutant, HPV16 E6/7, etc.). Therefore, although not found in normal cells, it is highly heterogeneous due to variation in cancer cells between patients. Hence, it is considered a neoantigen. Dendritic cell vaccines usually attempt to present antigens to MHC molecules by targeting these antigens. Anticancer immunotherapy using TAA-specific T cells is widely applicable due to the use of an antigen that is common to many patients, but TAA is a self-antigen and thus an autoreactive CD4$^+$ or CD8$^+$ T cell repertoire is selectively eliminated by central immune tolerance. On the other hand, neoantigen-specific T cells have high tumor specificity and high immunogenicity (i.e. induce T-cell receptors having high affinity) compared to TAA, and do not have immune tolerance. Accordingly, the use of a combination of TAA and neoantigen in dendritic cells is expected to more effectively induce T-cell responses. Recently, cancer vaccines using the same have been under development.

However, limitations of current cancer vaccine technology for treatment are difficulty and low scalability of procedures for identification and validation of cancer-specific neoantigens for each patient. In other words, even for the same type of tumor, the genotype and protein mutations are very different across patients, and even within the same tumor from the same patient, cancer cells that make up the tumor have different mutations (tumor heterogeneity), and thus a long time and high cost are required in order to identify and validate individual cancer-specific neoantigens, and application to a large number of patients is difficult because customized manufacture based on the patient's neoantigen is necessary.

The activation of CD8$^+$ T cells upon viral infection is very important because effector cells that directly eliminate virus-infected cells are CD8$^+$ cytotoxic T cells. In general, antigen of virus proteins may be delivered from lymph nodes to antigen-presenting cells such as DCs, degraded into CD8$^+$ T-cell antigen epitope peptides through processing, and then presented to MHC-I through cross-presentation. Virus-derived peptide-MHC-I complex-specific naive CD8$^+$ T cells presented by dendritic cells are activated as effector T cells. The virus-derived peptide-MHC-I complexes of virus-infected cells are recognized by effector CD8$^+$ T-cell TCRs, and cells infected with the secreted effector materials, such as interferon-gamma (IFN-γ), granzyme B, and perforin, are immediately eliminated. However, in the case of chronic viral infections such as human immunodeficiency virus (HIV), hepatitis B virus (HBV), and hepatitis C virus (HCV), in which stimulation of antigens of virus is persistent, the effector function of virus-specific CD8$^+$ T cells is decreased and the expression of immune checkpoint receptors is increased, indicating an exhausted T-cell phenotype. In addition, exhausted virus-specific CD8$^+$ T cells result in cell death due to weakened proliferation ability.

However, depending on the type of virus, there exist cytomegalovirus (CMV) and herpes simplex virus-1 (HSV-1), which do not show the phenotype of exhausted T cells despite chronic viral infection. These virus-specific CD8$^+$ T cells are not lacking even after removal of virus-infected cells, and may be present in the blood at a high rate as effector-memory T cells for a fairly long period of time. This characteristic is referred to as "memory inflation" (O'Hara, Welten et al. 2012). Inflationary memory T cells have the effector-memory phenotype of CD62L– CD27– CD28–, and stay in the tissue without homing to the lymph node due to lack of a CCR7 marker and expression of a CXCR3 marker. In addition, according to a recent report, CD45RO+ CCR7– CD8$^+$ T cells specific to cytomegalovirus, Epstein-Barr virus, and influenza A virus (IAV) were found in the blood and tumor tissues of cancer patients, and after stimulation with virus-derived peptides, cytokines such as IFN-γ and TNF-α were expressed and shown to be functionally activated (Rosato, Wijeyesinghe et al. 2019).

Among the viruses mentioned above, human cytomegalovirus (human CMV) is a beta-herpes virus having a double-stranded DNA genome and is not a virus that generally causes tumors. 60-80% of persons are infected with CMV worldwide, and may become infected continuously throughout life. Healthy infected persons show no symptoms, but serious illness may be caused in immunocompromised persons. An immune response by CMV-specific CD8$^+$ T cells occurs by focusing on CMV-derived pp65 (65 kDa phosphoprotein) matrix protein and IE-1 (immediately early protein-1) protein (Jackson, Mason et al. 2014). In particular, it has been reported that, in the blood of healthy CMV-infected persons, the frequency of CD8$^+$ T cells that specifically recognize the complex of the HLA-A*02:01 subgenotype among MHC-I molecules and the pp65 protein-derived peptide sequence 495-503 accounts for 0.5-11% of all CD8$^+$ T cells (Schmittnaegel, Levitsky et al. 2015). In addition, it is known that the frequency of CMV-specific CD8$^+$ T cells increases significantly as a CMV-infected person ages (Staras, Dollard et al. 2006).

An MHC-I molecule is composed of alpha chains 1, 2, and 3 and beta-2-microglobulin, and a total of six different antigen-presenting molecules including two HLA-As, two HLA-Bs, and two HLA-Cs are generated depending on the type of alpha chain. Among HLA-A proteins, the HLA-A*02 type is present in about 25-30% of the global population, and in particular, the HLA-A*02:01 subtype is present in 30-90% thereof, and is thus regarded as the most common MHC-I (Lai, Choo et al. 2017).

As mentioned above, the activation of CD8$^+$ cytotoxic T cells specific to virus-derived peptides through an adaptive immune response is generally required in order to eliminate virus-infected cells. This process is very similar to the adaptive immune response in which, when cancer occurs, cancer-derived peptide (TAA or TSA) is presented to MHC class I and class II molecules of APCs and CD8$^+$ T and CD4$^+$ T cells specific to the peptide-MHC complex are activated to induce cancer cell death. Therefore, there have been various studies on cancer treatment using non-self-antigen-specific T cells and TSA-specific T cells, including virus-specific T cells. To this end, in order to directly kill cancer cells, activation of cytotoxic T cells is essential, and a process of presenting a peptide epitope to MHC-I is required therefor.

Attempts have been made to use CMV-specific CD8$^+$ T cells for the treatment of glioblastoma, because there are several reports of CMV antigen expression in glioblastoma. CMV-specific CD8$^+$ T cells present in PBMCs isolated from the blood of glioblastoma patients were stimulated in vitro using CMVpRNA-transfected autologous dendritic cells as APCs to thus effectively amplify CMV pp65-specific cytotoxic T cells and kill autologous glioblastoma cells in vitro (Nair, De Leon et al. 2014). This may be said to be a presentation method that follows the general MHC-I peptide presentation pathway because it induces antigen expression in the cytosol using RNA. However, since a process of inducing antigen expression using RNA encoding the entire antigen is required, there are disadvantages such as difficulty in isolation and maturation of dendritic cells in a patient and low efficiency of RNA transfection.

For dendritic cells, the T-cell antigen epitope derived from the foreign protein may be actively presented to the MHC-I molecule through cross-presentation. As such, attempts have been made to induce the activation of peptide-specific CD8$^+$ or CD4$^+$ T cells by constructing a protein in which peptides to be delivered are fused in various forms to antibodies targeting CD40, DC-SIGN, MR (mannose receptor), and DEC205, which are receptors specifically expressed in dendritic cells. A case of inhibition of tumor growth in a mouse tumor model that induces T-cell activation and expresses HPV16 E6/E7 using a protein obtained by fusing HPV16 E6 and E7 protein sequences to an antibody targeting CD40 has been reported (Yin, Duluc et al. 2016). In addition, a case in which a protein fragment sequence 250-264 containing the T-cell antigen epitope sequence 257-264 (SIINFEKL) (SEQ ID NO: 51) of H-2Kb, which is mouse MHC-I derived from an ovalbumin (OVA) protein, is fused to anti-DNA SCFv (single-chain variable fragment) and cross-presented to dendritic cells has been reported (Pham, Woo et al. 2012). Since the above two methods require a process in which peptide-specific T cells are activated by dendritic cells, immunization has to be performed first, and the effect may be obtained only upon administration together with an adjuvant, which is undesirable.

There has been reported a case in which a T-cell antigen epitope is delivered to MHC-I of cancer cells using antibody-targeted pathogen-derived peptides in which a virus-derived T-cell antigen epitope peptide containing a cysteine residue is fused to the C-terminal portion of the Fc domain of an antibody capable of endocytosis by targeting a cancer-cell-specific receptor via a thioether linker through a chemical reaction (Sefrin, Hillringhaus et al. 2019). The antibody-peptide complex localized in the endosome after endocytosis by binding to the cancer cell surface receptor uses a mechanism by which a disulfide bond is reduced under reducing conditions of the endosome and the peptide is dissociated within the endosome and binds to the MHC-I molecule that is recycled in the endosome so that the peptide-MHC-I complex is presented on the cell surface. In the literature, an antibody-EBV LMP 2 peptide 426-434 (CLGGLLTMV) (SEQ ID NO: 52) complex has been reported to be able to induce cancer cell death in the presence of EBV-specific cytotoxic T cells even at low concentrations after treatment of cancer cells therewith and also to inhibit the growth of transplanted tumors in vivo in mice. In addition, it was shown that the mild tumor growth inhibitory effect due to PD-1 expression of EBV-specific cytotoxic T cells and PD-L1 expression of transplanted tumors in vivo in mice may be overcome by co-administration of the anti-PD-1 antibody. However, in this method, the peptide dissociated in the endosome and MHC-I are allowed to bind and presented on the cell surface. In the method, the peptide, which is a T-cell antigen epitope, does not reach the cytosol. Therefore, since it does not follow the general MHC-I presentation pathway and a cysteine residue must exist in order to enable disulfide bonding within the epitope peptide, the type of epitope peptide capable of being used is very limited. In this method, also, since the peptide does not reach the cytosol and does not undergo intracellular antigen processing by a proteasome or ubiquitin proteasome within the cytosol, the peptide epitope capable of being linked to the antibody is limited to a peptide that binds directly to MHC-I, namely a peptide composed of 8-11 amino acid residues. A longer peptide (peptide containing 12 or more amino acid residues) has a disadvantage in that it cannot be displayed to MHC-I in the endosome. Moreover, in this method, a T-cell antigen epitope peptide is not presented to MHC-I when a non-cleavable linker is used.

Another approach is ATPP (antibody-targeted pathogen-derived peptide) technology. This technology pertains to the case in which the $CMV_p495$-503 (NLVPMVATV) (SEQ ID NO: 13) peptide, which is a CMV-specific T-cell antigen epitope peptide, is linked to the tumor surface antigen-targeting antibody via a cleavable linker in the intracellular endosomal environment (low pH, reducing environment) so that the T-cell antigen epitope peptide-MHC-I complex is displayed on the surface of tumor cells (WO2016/126611, Targeting moiety peptide epitope complexes having a plurality of T-cell epitopes). In this method, the antibody and the peptide are prepared separately and are linked via a cleavable linker through a chemical reaction. This approach uses a mechanism by which, in the antibody-peptide complex that is localized in the endosome after endocytosis by binding of the antibody to the cancer cell surface receptor, the disulfide bond is reduced under weakly acidic or reducing conditions of the endosome and the peptide is dissociated within the endosome and binds to the MHC-I molecule that is recycled within the endosome so that the peptide-MHC-I complex is presented on the cell surface. However, in this method, since the peptide does not reach the cytosol and does not undergo intracellular antigen processing by the ubiquitin proteasome within the cytosol, the peptide epitope that is linked to the antibody is limited to a peptide that directly binds to MHC-I, namely a peptide composed of 8-11 amino acid residues. A longer peptide (peptide containing 12 or more amino acid residues) has a disadvantage in that it cannot be displayed to MHC-I in the endosome. Moreover, in this method, the T-cell antigen epitope peptide is not presented to MHC-I when a non-cleavable linker is used.

Still another approach is APEC (antibody-peptide epitope conjugate) technology. This technology pertains to the case in which a CMV-specific T-cell antigen epitope, namely a $CMV_p495$-503 (NLVPMVATV) (SEQ ID NO: 13) peptide, is linked to a tumor surface antigen-targeting antibody via a cleavable linker that is cleaved by a protease that is expressed by a tumor cell or is present on the surface of a tumor cell so that the T-cell antigen epitope-MHC-I complex is displayed on the surface of tumor cells (WO2012/123755, Re-Directed Immunotherapy). In this method, when the linker is cleaved by a protease (e.g. metalloproteinase, MMP) in the state in which the antibody is not endocytosed into the cells but binds to the tumor surface antigen on the surface of cancer cells, binding of the peptide to MHC-I on the cell surface is used. However, in this method, since the peptide does not reach the cytosol and does not undergo intracellular antigen processing by the ubiquitin proteasome within the cytosol, the peptide epitope linked to the antibody is limited to a peptide that directly binds to MHC-I, namely a peptide composed of 8-11 amino acid residues. A longer peptide (peptide containing 12 or more amino acid residues) has a disadvantage in that it cannot be displayed to MHC-I in the endosome. Moreover, in this method, the T-cell antigen epitope peptide is not presented to MHC-I when a non-cleavable linker is used. Furthermore, since hydrolysis is induced using various proteases, the protease may hydrolyze the epitope peptide itself, resulting in loss of the T-cell antigen epitope peptide.

Yet another approach is construction of a pMHC-I-antibody format expressed after fusion of a complex of MHC-I and a virus-specific T-cell antigen epitope or a peptide comprising the same to a tumor surface antigen-specific antibody (IgG and SCFv form) via a peptide linker (Schmittnaegel, Levitsky et al. 2015). This is an attempt to overcome MHC-I loss that occurs due to the immune escape mechanism in a tumor microenvironment. Since the pMHC-I-antibody binds to the tumor cell surface and the peptide-MHC-I complex is present, recognition of virus-specific cytotoxic T cells may be induced even when the MHC-I molecule is lost. In an in-vitro experiment, it was possible to induce death of tumor cells in the presence of virus-specific cytotoxic T cells, and a tumor growth inhibitory effect was exhibited in vivo in mice. However, in order to prevent T-cell activation due to nonspecific TCR cross-linking in the absence of cancer cells, it is necessary to construct a single pMHC-I-IgG by introducing heterodimeric Fc technology. For expression thereof, three recombinant plasmids are required: pMHC-I-bound heavy chain, pMHC-I-free heavy chain, and light chain, which is undesirable. The expression level thereof is also much lower than that of a general antibody, and a large amount of oligomer exists even after purification, so it is not suitable for development as a therapeutic antibody. In addition, in this method, the peptide, which is a T-cell antigen epitope, does not reach the cytosol.

As described above, conventional cancer vaccines have been developed in a manner of inducing T-cell immune responses by presenting antigen-derived peptide epitopes to MHC molecules on the surface of dendritic cells. As means for presenting antigens to dendritic cells, various methods such as DNA or RNA vaccines, peptide vaccines, tumor cell vaccines, vaccines using virus-derived vectors, and the like have been utilized. However, no method has been reported so far to specifically deliver an antigen-derived T-cell antigen epitope or a peptide comprising the same to MHC-I molecules on the surface of cancer cells through intracellular antigen processing.

Moreover, the conventional cancer vaccine technology is limited because a long time and high cost are required for identification and validation of a neoantigen that is highly specific to a patient, and also because scalability is low due to customized manufacture for each patient.

DISCLOSURE

In order to overcome the above limitations, the present invention provides a fusion antibody capable of presenting a CD8⁺ T-cell antigen epitope to an antigen-presenting molecule MHC-I on the surface of a target cell by specifically delivering a virus-derived antigen to the cytosol of the target cell so that it may be used universally in patients without the need for patient-specific neoantigen identification and validation steps, and a composition for preventing and/or treating cancers, autoimmune diseases, or infectious diseases including the same.

In order to accomplish the above object, the present invention provides a fusion antibody in which a T-cell antigen epitope or a peptide comprising the same is fused to a cell- or tissue-specific cellular cytosol-penetrating antibody (cytotransmab) in order to deliver an antigen-derived CD8⁺ T-cell antigen epitope or a peptide comprising the same to the cytosol of a target cell.

In the present invention, the fusion antibody is configured such that a CD8⁺ T-cell antigen epitope or a peptide comprising the same is genetically fused to a cytosol-penetrating antibody having cell- or tissue-specific cytosol-penetrating ability, whereby the CD8⁺ T-cell antigen epitope or the peptide comprising the same is delivered to the cytosol of a target cell so that the T-cell antigen epitope may be presented to the antigen-presenting molecule MHC-I on the surface of the target cell, but the present invention is not limited thereto.

In particular, the fusion antibody according to the present invention delivers a CD8⁺ T-cell antigen epitope or a peptide comprising the same to the cytosol of a target cell, so the T-cell antigen epitope or the peptide comprising the same delivered to the cytosol is subjected to intracellular antigen processing so as to ultimately present the CD8⁺ T-cell antigen epitope to the antigen-presenting molecule MHC-I on the surface of the target cell.

Specifically, the fusion antibody according to the present invention, which immunoglobulin form, preferably an intact immunoglobulin form, is endocytosed by binding to a membrane protein receptor overexpressed on the surface of a target cell such as a tumor tissue, and is then localized in the cytosol through endosomal escape, and a virus-specific epitope generated by a proteolytic system in the cytosol enters the endoplasmic reticulum, binds to MHC-I, and is secreted through the Golgi apparatus, so a T-cell antigen epitope or a peptide comprising the same, preferably a virus-specific T-cell antigen epitope or a peptide comprising the same, may be presented to MHC-I on the surface of the target cell.

In the present invention, "CD8⁺ T-cell antigen epitope" and "T-cell antigen epitope" are used with substantially the same meaning, and refer to a peptide epitope that binds to MHC-I and is displayed on the surface of a target cell.

The fusion antibody according to the present invention is, for example, in a form in which an antigen of virus-derived CD8⁺ T-cell antigen epitope or a peptide comprising the same, such as CMV pp65, is fused to a cytosol-penetrating antibody, and when administered to a patient, the fusion antibody penetrates the cytosol of a target cell, and a CMV pp65-specific CD8⁺ T-cell antigen epitope or a peptide comprising the same generated through intracellular antigen processing enters the endoplasmic reticulum in the cell and binds to HLA-A*02:01 to form a CMVpp65 peptide/HLA-A*02:01 complex (pMHC), and this pMHC is secreted through the Golgi apparatus and presented on the target cell surface, and thus CMV pp65-specific cytotoxic T lymphocytes (CTLs) circulating in the patient's body recognize the target cell as a virus-infected cell and kill the target cell, ultimately showing the effect of treating cancer, autoimmune diseases, and infectious diseases caused by the target cell.

In the present invention, the target cell is understood to include not only abnormal cells, such as cancer cells, cells infected with viruses or pathogenic microorganisms, and the like, which are not normal cells and are thus to be removed from the human body, but also cells such as mast cells, eosinophils, basophils, neutrophils, helper T cells (CD4⁺ T cells), cytotoxic T cells (CD8⁺ T cells), macrophages, epithelial cells, muscle cells, skin cells, stem cells, etc.

In addition, in the present invention, the antigen-derived CD8⁺ T-cell antigen epitope or the peptide comprising the same is preferably derived from an antigen of virus that may cause infection in humans. More preferably, it is a T-cell antigen epitope of an antigen of virus in which CTLs (cytotoxic T lymphocytes) for the antigen are still formed in the human body despite natural immunity following widespread infection in humans, or a peptide comprising the same.

The antigen-derived CD8⁺ T-cell antigen epitope or the peptide comprising the same is preferably derived from 65 kDa phosphoprotein (pp65) antigen of cytomegalovirus (CMV), human papilloma virus (HPV), or Epstein-Barr virus (EBV), or a peptide comprising the same.

The CD8⁺ T-cell antigen epitope or the peptide comprising the same may be a cytomegalovirus (CMV)-derived T-cell antigen epitope or a peptide comprising the same, for example, CMV pp65. The CD8⁺ T-cell CMV pp65 antigen epitope or the peptide comprising the same may be a peptide including the sequence of SEQ ID NO: 13, or further extended epitopes or peptides including 1 to 16 amino acids extended residues at the N-terminus and/or C-terminus of SEQ ID NO: 13. 1, 2, 3, 4, 5, 6, 7, 8, 9, 10, 11, 12, 13, 14, 15, or 16 amino acids may be further included at the N-terminus and/or C-terminus of SEQ ID NO: 13. The amino acids that are additionally included may be provided to either or both of the N-terminus and the C-terminus.

Specifically, the CD8⁺ T-cell antigen epitope or the peptide comprising the same is more preferably any one of SEQ ID NOS: 13 to 36 derived from one of the antigens originated from CMV-, HPV-, or EBV viruses, or a peptide comprising the same, and most preferably a CMV-specific epitope having the sequence of SEQ ID NO: 26, but is not limited thereto.

Moreover, in the present invention, the antigen-derived CD8[+] T-cell antigen epitope or the peptide comprising the same may be derived from a tumor-associated antigen (TAA) or a tumor-specific antigen (TSA).

In an embodiment of the present invention, the CD8[+] T-cell antigen epitope or the peptide comprising the same may be a T-cell antigen epitope (composed of 8-11 amino acid residues) that directly binds to MHC-I, or a longer peptide (a peptide including 12 or more amino acid residues), for example, a peptide having the sequence of any one of SEQ ID NO: 13 to SEQ ID NO: 36, but is not limited thereto.

In the fusion antibody according to the present invention, the T-cell antigen epitope or the peptide comprising the same is inserted or incorporated into the interior of a cytosol-penetrating antibody (immunoglobulin), particularly into the middle portion of a heavy chain or a light chain, or is fused to the N-terminus or C-terminus thereof, but the present invention is not limited thereto.

In addition, 1 or more, preferably 1 to 20, more preferably 1 to 6, most preferably 1 to 4 T-cell antigen epitopes according to the present invention or peptides containing the same are inserted into or bound to the interior, N-terminus, or C-terminus of the cytosol-penetrating antibody, preferably fused thereto, but the present invention is not limited thereto.

One or more T-cell antigen epitopes or peptides containing the same, inserted into or bound to the interior, N-terminus, or C-terminus of the cytosol-penetrating antibody, may be the same as or different from each other. When two or more of the same T-cell antigen epitopes or peptides containing the same are inserted into or bound to the interior, N-terminus, or C-terminus of the cytosol-penetrating antibody, the efficiency of presentation of the T-cell antigen epitopes to the antigen-presenting molecule MHC-I on the target cell surface may be increased. In particular, when two or more different T-cell antigen epitopes or peptides containing the same are inserted into or bound to the interior, N-terminus, or C-terminus of the cytosol-penetrating antibody, a broad therapeutic spectrum similar to that of multivalent vaccines may be provided.

Accordingly, in one aspect, the fusion antibody according to the present invention may be configured such that the T-cell antigen epitope or the peptide comprising the same is inserted into the middle portion of the hinge region, heavy-chain variable region, CH1, CH2, or CH3 domain, light-chain variable region, or light-chain constant region domain (CL) of the cytosol-penetrating antibody. Here, since the T-cell antigen epitope or the peptide comprising the same used in the fusion antibody according to the present invention is not large in size, it does not significantly affect the intrinsic properties of the cytosol-penetrating antibody.

In another aspect, the fusion antibody according to the present invention may be in a form (T-cell epitope-fused cytotransmab) in which the T-cell antigen epitope or the peptide comprising the same is fused to the C-terminus of the heavy chain or light chain of the cytosol-penetrating antibody, and is preferably a fusion antibody (viral peptide epitope-fused cytotransmab) in which the antigen of virus-derived epitope peptide is fused to the cytosol-penetrating antibody, but is not limited thereto.

Also, in the present invention, any cell- or tissue-specific cytosol-penetrating antibody may be used without limitation, so long as it is able to be endocytosed into the cell, and it is more preferable that it be localized in the cytosol through endosomal escape after endocytosis into the cell, but the present invention is not limited thereto.

In the present invention, the "CD8[+] T-cell antigen epitope" or "T-cell antigen epitope" is a peptide that is composed of 8-11 amino acid residues and directly binds to MHC-I to form a peptide-MHC-I complex, and refers to a peptide that allows the CD8[+] T cells to recognize the peptide-MHC-I complex through the T-cell receptor. In the present invention, the "peptide comprising the CD8[+] T-cell antigen epitope" or "peptide comprising the T-cell antigen epitope" is a peptide that includes the T-cell antigen epitope and further includes an amino acid residue at the N-terminus or C-terminus thereof, the peptide comprising 20 or more amino acid residues.

In the fusion antibody according to the present invention, one, two, three, or more, preferably one, T-cell antigen epitope or peptide comprising the same is inserted into or fused to the interior or terminus of the cytosol-penetrating antibody, but the present invention is not limited thereto. More preferable is a fusion antibody in which one or two, particularly one, T-cell antigen epitope or peptide comprising the same is fused to the C-terminus of the heavy chain.

In the fusion antibody according to the present invention, the cytosol-penetrating antibody and the CD8[+] T-cell antigen epitope or the peptide comprising the same are inserted into the interior of the antibody or are fused to the terminus a non-cleavable linker or a cleavable linker that is cleavable in the endosome. Here, the linker preferably includes $G_4S$ or GFLG, but is not limited thereto.

In addition, the fusion antibody according to the present invention may further include a material targeting a target-cell-specific antigen. The material targeting the target-cell-specific antigen bind to the fusion antibody through genetic fusion, linker-mediated coupling, covalent linkage, etc., but the present invention is not limited thereto.

In the present invention, the "material targeting a target-cell-specific antigen" is a material a having function of specifically selectively inducing endocytosis of the fusion antibody according to the present invention to a target cell by specifically binding to an antigen that is specifically expressed on the surface of a target cell.

The material targeting the target-cell-specific antigen is a material having a function of specifically delivering the fusion antibody according to the present invention to a target cell of interest, and may be a ligand, an oligopeptide, an antibody, or a fragment thereof, or an aptamer, which is capable of specifically binding to the target-cell-specific antigen, but is not limited thereto.

The target-cell-specific antigen is not particularly limited, so long as it is a receptor that is specifically expressed or overexpressed in a target cell, for example, a tumor cell, a pathogenic virus, or a microorganism. It is preferably any one selected from the group consisting of EpCAM (epithelial cell adhesion molecule), EGFR (epidermal growth factor receptor, Her1), Her2/Neu, Her3, Her4, EGFRVIII, integrin $\alpha v \beta 3$, integrin $\alpha v \beta 5$, integrin $\alpha v \beta 6$, IGER (insulin-like growth factor), mesothelin, CEA (carcinoembryonic antigen), MUC1 (mucin 1), CD20 (B-lymphocyte antigen CD20), CD19, CD22, CD25, CD33, CD38, CD123, Lewis Y, PD-1 (programmed cell death protein 1), PD-L1 (programmed death-ligand 1), CTLA4 (cytotoxic T-lymphocyte-associated protein 4), PSMA (prostate-specific membrane antigen), Ang2 (angiopoietin-2), PDGF-R (platelet-derived growth factor receptor), VEGF-R (vascular endothelial growth factor receptor), neurophilin, c-Met, pathogenic virus-specific antigen, pathogenic microorganism-specific antigen, mast-cell-specific antigen, eosinophil-specific antigen, basophil-specific antigen, neutrophil-specific antigen, helper T cell (CD4[+] T cell)-specific antigen, cytotoxic T-cell (CD8⁺ T cell)-specific antigen, macrophage-specific antigen, epithelial-cell-specific antigen, muscle-cell-specific antigen, skin-cell-specific antigen, and stem-cell-specific antigen, but is not limited thereto.

In an embodiment of the present invention, it has been confirmed that a fusion antibody was produced by fusing, to the C-terminus of the heavy-chain constant region based on an inCT99 cytosol-penetrating antibody in which the heavy-chain variable region and the light-chain variable region are imparted with cytosol-penetrating ability, a T-cell antigen epitope including a CD8⁺ T-cell antigen epitope (a peptide composed of 8-11 amino acid residues binding to MHC-I) and additional amino acid residues at the N-terminus of the T-cell antigen epitope, and a peptide comprising the T-cell antigen epitope including additional amino acid residues at the N-terminus and the C-terminus of the T-cell antigen epitope, and also that the CD8⁺ T-cell antigen epitope was capable of being displayed on the target cell surface using this fusion antibody.

In addition, the present invention provides a composition for presenting a T-cell antigen epitope on the surface of a target cell, which includes the fusion antibody according to the present invention and in which the CD8⁺ T-cell antigen epitope or the peptide comprising the same is localized in the cytosol of the target cell by the cytosol-penetrating antibody.

The composition including the fusion antibody according to the present invention enables a virus-specific epitope to be presented to the antigen-presenting molecule MHC-I on the target cell surface, thereby stimulating virus-specific cytotoxic T lymphocytes (CTLS) already present in the human body to selectively recognize and eliminate target cells.

In addition, the present invention provides a composition for preventing and/or treating cancer or an infectious disease including the fusion antibody according to the present invention.

In a preferred embodiment, the target cell may be a cancer cell. Accordingly, the present invention provides a composition for preventing or treating cancer including the fusion antibody according to the present invention, namely a general-purpose therapeutic cancer vaccine.

Specifically, the general-purpose therapeutic cancer vaccine according to the present invention is capable of displaying a virus-specific CD8⁺ T-cell antigen epitope on the surface of a cancer cell to an antigen-presenting molecule MHC-1 on the surface of a target cell using an antigen of virus-derived peptide epitope fusion antibody (viral peptide epitope-fused cytotransmab), whereby cancer cells may be selectively eliminated using virus-specific cytotoxic T lymphocytes (CTLs) already present in the cancer patient's body due to prior exposure to the virus.

Among immune mechanisms for eliminating cancer that occurs in the human body, CTLs show the strongest ability to kill cancer cells. Nevertheless, the reason why tumors occur is that CTLs are not activated because cancer-specific neoantigens are not presented on the surface of cancer cells.

Accordingly, the present invention was conceived based on the question of whether it is possible to eliminate cancer cells using CTLs that have already been activated in the tumor patient's body by developing a general-purpose cancer vaccine that does not require the process of identifying/validating cancer-specific antigens, which is the biggest challenge in current cancer vaccine technology. To this end, the present inventors focused on viral antigens for which CTLs are already formed in the body due to vaccination at birth or widespread exposure during life. For example, the reason why it is possible to live in good health without major problems even when people are infected with influenza virus or cytomegalovirus (CMV) is that virus-specific CTLs in the body are activated to thus eliminate infected cells. These CTLs exist as memory T cells in the human body, and by allowing cancer cells of the patient's tumor tissue to present the virus-specific antigen as if infected with a virus, the virus-specific CTLs are redirected to thus eliminate the tumor. Simply put, this is a strategy to recognize cancer cells as virus-infected cells.

In order to accomplish the above object, as an example, a CMV-derived antigen is delivered to the cytosol of a cancer cell, and the CMV-derived antigen T-cell antigen epitope peptide binds to MHC-I through intracellular antigen processing so that the peptide-MHC-I complex is presented on the surface of the target cell, namely the cancer cell. Accordingly, the present invention provides a method of developing a CMV-derived antigen as a general-purpose vaccine, for example a cancer vaccine.

The cancer vaccine according to the present invention is advantageous because 60 to 90% of the global population show CMV infection and a significant number of infected people have CMV pp65-specific cytotoxic T cells (CTL) in their bodies, so it may be used universally, rather than requiring customized manufacture for a patient, and may thus be widely adopted.

In particular, among the CMV antigens, the pp65 protein-derived peptide (amino acid residues 495-503) forms a complex with HLA-A*02:01 in the MHC-I gene of human cells and thus this complex is presented on the surface of infected cells with high efficiency. The HLA-A*02:01 MHC-I genotype is possessed by about 16% of the global population, so it is highly versatile.

Specifically, since normal adults are frequently infected with CMV and recover, activated CTLs are always present. Among CTLs in the blood of normal CMV-infected adults, CMV pp65-specific cytotoxic T cells (CMVpp65-CTLs) are present at a very high frequency of about 0.5 to 11%. It has been reported in the literature that, when CMVpp65-CTLs are isolated from the human blood and then the synthesized CMVpp65 peptide antigen is allowed to bind to HLA-A*02:01 on the cancer cell surface and cultured with antigen-presenting cancer cells in vitro, CMVpp65-CTLs are capable of efficiently inducing cancer cell death. Moreover, when a tumor expressing a CMVpp65 antigen was transplanted into a mouse and human-derived CMVpp65-CTLs were injected into the mouse (adoptive transfer), tumor growth was observed to be inhibited in the mouse. This suggests that CMVpp65-CTLs are capable of recognizing and eliminating the tumor when the CMVpp65 antigen is presented to cancer cells in the human body.

However, the study above merely shows the potential of the CMVpp65 peptide as a therapeutic cancer vaccine, and is difficult to apply to actual clinical practice due to the absence of tumor specificity and cytosol-penetrating ability and short blood half-life when administered in the human body. In order to be practically applied to patients, technology in which the CMVpp65 peptide is distributed to cancer tissue and efficiently delivered into the cytosol of cancer cells and thus displayed on the surface of cancer cells by HLA-A*02:01 is required. Such requirements are perfectly matched with the fusion antibody according to the present invention and the composition including the same.

In addition, the present invention provides a method of producing a fusion antibody in which a T-cell antigen epitope, preferably an antigen of virus-derived T-cell antigen epitope, or a peptide comprising the same is fused to a cytosol-penetrating antibody. Here, the fusion antibody in an immunoglobulin form, preferably in an intact immunoglobulin form, is endocytosed by binding to a membrane protein receptor on the cell surface overexpressed in a tumor tissue and is then localized in the cytosol through endosomal escape, and a virus-specific epitope generated by a proteolytic system in the cytosol enters the endoplasmic reticulum, binds to MHC-I, and is secreted through the Golgi apparatus, thereby presenting the virus-specific epitope to MHC-I on the target cell surface.

Specifically, the present invention provides a method of producing a fusion antibody in which an antigen of virus-derived T-cell antigen epitope or a peptide comprising the same, preferably an epitope derived from viral proteins of cytomegalovirus (CMV), human papilloma virus (HPV16), or Epstein-Barr virus (EBV), or a peptide comprising the epitope, is fused to a cytosol-penetrating antibody.

In addition, the present invention provides a method for fragmenting the epitope of CMV-derived antigen pp65 and HPV16-derived antigen E7 or the peptide region including the same in various forms and identifying an optimal CD8$^+$ T-cell antigen epitope region capable of being fused to a cytosol-penetrating antibody.

In order to increase the efficacy of the virus-specific T-cell antigen epitope expressed on the target cell surface, the present invention provides a method of improving the sequence and length of the virus-specific T-cell antigen epitope binding to the fusion antibody or the peptide comprising the same, a method of linking different peptides, and a fusion antibody including the virus-specific T-cell antigen epitope thus improved.

Moreover, in order to efficiently present an antigen of virus-derived T-cell antigen epitope expressed on the surface of a target cell to MHC-I, the present invention provides a peptide linker for use in fusing an antigen of virus-derived T-cell antigen epitope or a peptide comprising the same to an antibody and a method of improving the linker.

In addition, the present invention provides a method of inhibiting the growth of cancer or tumor cells and/or a method of preventing or treating cancer or tumors using the fusion antibody according to the present invention or the composition including the same.

In addition, the present invention provides a method of preventing or treating an autoimmune disease or an infectious disease using the fusion antibody according to the present invention or the composition including the same.

In addition, the present invention provides a polynucleotide encoding the fusion antibody according to the present invention, a recombinant expression vector including the polynucleotide, or a host cell including the polynucleotide encoding the fusion antibody or the recombinant expression vector including the same.

In addition, the present invention provides a method of producing a fusion antibody including culturing the host cell and recovering the produced fusion antibody.

Specifically, the method of producing the fusion antibody according to the present invention may include the following steps, by way of example, but is not limited thereto:

(1) preparing a heavy-chain expression vector cloned with nucleic acids encoding a heavy chain including an endosomal escape cytosol-penetrating heavy-chain variable region (VH) and a heavy-chain constant region (CH1-hinge-CH2-CH3) of a human antibody and a T-cell antigen epitope or a peptide comprising the same is fused to the C-terminus of the heavy chain;

(2) preparing light-chain expression vector cloned with nucleic acids encoding an amino acid of a light chain including an endosomal escape cytosol-penetrating light-chain variable region (VL) and a light-chain constant region (CL) of the human antibody;

(3) expressing a fusion antibody in an intact immunoglobulin form in which a human T-cell antigen epitope or a peptide comprising the same is fused to the cytosol-penetrating antibody by co-transfecting animal cells for protein expression with the heavy-chain expression vector and the light-chain expression vector; and (4) purifying and recovering the expressed fusion antibody.

In addition, the present invention provides a method of delivering a CD8$^+$ T-cell antigen epitope or a peptide comprising the same into the cytosol using the fusion antibody according to the present invention.

Specifically, in the method of the present invention, the fusion antibody according to the present invention is endocytosed into the cell by the cytosol-penetrating antibody and is then localized in the cytosol through endosomal escape, thereby delivering the CD8$^+$ T-cell antigen epitope or the peptide comprising the same into the cytosol.

In addition, the present invention provides a method of presenting a CD8$^+$ T-cell antigen epitope or a peptide comprising the same on the surface of a target cell.

In this method, a CD8$^+$ T-cell antigen epitope or a peptide comprising the epitope is delivered into the cytosol in the form of a fusion antibody in which a CD8$^+$ T-cell antigen epitope or a peptide comprising the same is fused to a cell- or tissue-specific cytosol-penetrating antibody, and the fusion antibody is endocytosed into the cell by the cytosol-penetrating antibody and is then localized in the cytosol through endosomal escape, thereby presenting the CD8$^+$ T-cell antigen epitope or the peptide comprising the same on the target cell surface, but the present invention is not limited thereto.

DESCRIPTION OF DRAWINGS

FIG. 1 schematically shows an inCT99 antibody and an inCT99†viral epitope fusion antibody;

FIG. 2a to FIG. 2c schematically show inCT99(AAA)†CMV, Cetuximab†CMV, and Necitumumab†CMV fusion antibodies as negative control antibodies, FIG. 2a schematically showing inCT99(AAA)+CMV in which an endosomal escape motif $^{92}WYW^{94}$ present in VL-CDR3 of an inCT99+CMV fusion antibody is mutated to $^{92}AAA^{94}$ and an endosomal escape motif $^{95}WYW^{98}$ present in VH-CDR3 thereof is mutated to $^{95}AAA^{98}$, FIG. 2b schematically showing Cetuximab†CMV in which a virus-specific T-cell antigen epitope or a peptide comprising the same is fused to the C-terminus of the heavy-chain region of a Cetuximab antibody via a G$_4$S linker, FIG. 2c schematically showing Necitumumab†CMV in which a virus-specific T-cell antigen epitope or a peptide comprising the same is fused to the C-terminus of the heavy-chain region of a Necitumumab antibody via a G$_4$S linker;

FIG. 3a and FIG. 3b schematically show vectors for expressing an inCT99 antibody and inCT99†CMV, inCT99†HPV, inCT99†EBV, and inCT99†OVA fusion antibodies in animal cells (HEK293F), FIG. 3a schematically showing a heavy-chain expression vector of the inCT99†viral peptide fusion antibody in which an antigen of virus-derived epitope peptide is fused to the heavy-chain constant region of the inCT99 antibody, which is a cytosol-penetrating antibody, FIG. 3b schematically showing a light-chain expression vector of the inCT99 antibody and the inCT99†viral peptide fusion antibody;

FIG. 4a to FIG. 4d schematically show vectors for expressing Cetuximab†CMV and Necitumumab†CMV fusion antibodies as control antibodies in animal cells (HEK293F), FIG. 4a schematically showing a heavy-chain expression vector of the Cetuximab†CMV fusion antibody, FIG. 4b schematically showing a light-chain expression vector of the Cetuximab†CMV fusion antibody, FIG. 4c schematically showing a heavy-chain expression vector of the Necitumumab†CMV fusion antibody, FIG. 4d schematically showing a light-chain expression vector of the Necitumumab†CMV fusion antibody;

FIG. 5a to FIG. 5d show the results of analysis of protein size and combination form through COOMASSIE® Blue staining after the inCT99†viral peptide fusion antibody was expressed and purified in animal cells (HEK293F) and then 3 μg of protein was separated through SDS-PAGE under reducing or non-reducing conditions, FIG. 5a showing results for the inCT99†CMV fusion antibody, FIG. 5b showing results for the inCT99†HPV fusion antibody, FIGS. 5c and 5d showing results for the inCT99†EBV fusion antibody;

FIG. 6 shows the results of flow cytometry analysis of expression of HLA-A2 among major histocompatibility complex (MHC) I genotypes and expression of integrin αvβ5/αvβ3 among cancer cell surface antigens in four human cancer cell lines;

FIG. 7a to FIG. 7d schematically show the expression vectors of T-cell receptor (TCR)-like antibodies and the results of analysis of size and combination form after purification, FIG. 7a schematically showing the expression vectors of T-cell receptor (TCR)-like antibodies, FIG. 7b showing the results of analysis of protein size and combination form through COOMASSIE® Blue staining after H9, H9#1, and H9#38 antibodies were expressed and purified in animal cells (HEK293F) and then 3 μg of protein was separated through SDS-PAGE under reducing or non-reducing conditions, FIG. 7c showing the results of analysis of the C1-17 antibody in the same manner as in FIG. 7b, FIG. 7d showing the results of analysis of 7-1 and L2 antibodies in the same manner as in FIG. 7b;

FIG. 8a to FIG. 8e show the results of flow cytometry analysis to determine the ability of T-cell receptor (TCR)-like antibodies to bind to the peptide/HLA-A*02:01 complex using cancer cell lines having different expression levels of HLA-A*02:01, FIG. 8a showing the results of measurement of the ability of the H9, H9#1, and H9#38 antibodies to bind to a CMV$_P$495-503/HLA-A*02:01 complex in cancer cells pulsed with CMV$_P$495-503 peptide, FIG. 8b showing the results of analysis of the ability of the inCT99†CMV fusion antibody to present the T-cell antigen epitope to HLA-A*02:01 through intracellular antigen processing, performed using H9#1 and H9#38 antibodies, FIG. 8c showing the results of measurement of the ability of the C1-17 antibody to bind to the CMV$_P$495-503/HLA-A*02:01 complex in cancer cells pulsed with CMV$_P$495-503 peptide, FIG. 8d showing the results of measurement of the ability of the 7-1 antibody to bind to a HPV$_E$11-19/HLA-A*02:01 complex in cancer cells pulsed with HPV$_E$11-19 peptide, FIG. 8e showing the results of measurement of the ability of the L2 antibody to bind to an EBV$_{L2}$426-434 (C426S)/HLA-A*02:01 complex in cancer cells pulsed with EBV$_{L2}$426-434 (C426S) peptide;

FIG. 9a to FIG. 9f show the results of flow cytometry analysis to determine the ability of various inCT99†CMV fusion antibodies to bind to cell-surface HLA-A*02:01 and to present the T-cell antigen epitope to HLA-A*02:01 through intracellular antigen processing, FIG. 9a showing a scheme for analyzing the ability of the inCT99†CMV fusion antibody to bind to the cell-surface HLA-A*02:01 at 4° C., FIG. 9b showing a scheme for analyzing the ability of the inCT99†CMV fusion antibody to present the T-cell antigen epitope to HLA-A*02:01 through intracellular antigen processing at 37° C., FIG. 9c showing the results of flow cytometry analysis after treatment with various inCT99†CMV fusion antibodies in the same manner as in FIGS. 7a and 7b, FIG. 9d showing the results of flow cytometry analysis after treatment with the inCT99†CMV$_P$480-503 fusion antibody and the control antibodies inCT99(AAA)†CMV$_P$480-503 and Cetuximab†CMV$_P$480-503 in the same manner as in FIGS. 9a and 9b, FIG. 9e showing the results of evaluation of the ability of the inCT99†CMV$_P$480-510 fusion antibody and the control antibodies inCT99(AAA)†CMV$_P$480-510 and Cetuximab†CMV$_P$480-510 to present the T-cell antigen epitope to HLA-A*02:01 through intracellular antigen processing at 37° C. in the same manner as in FIG. 9b, FIG. 9f showing the results of evaluation of the ability of the inCT99†CMV$_P$480-516 fusion antibody and the control antibodies inCT99(AAA)†CMV$_P$480-516 and Necitumumab†CMV$_P$480-516 to present the T-cell antigen epitope to HLA-A*02:01 through intracellular antigen processing at 37° C. in the same manner as in FIG. 9b;

FIG. 10a to FIG. 10c show the results of expression of HLA-A2, which is the HLA-A subgenotype, and the proportion and phenotype of CMV pp65-specific cytotoxic T cells before or after stimulation with the CMV$_P$495-503 peptide by subjecting peripheral blood mononuclear cells (PBMCs) isolated from the blood collected from healthy blood donors to staining using an anti-HLA-A2 antibody, FIG. 10a showing the results of flow cytometry analysis of expression of HLA-A2, which is the HLA-A subgenotype, of peripheral blood mononuclear cells (PBMC), FIG. 10b showing the results of flow cytometry analysis to determine the proportion of CMV pp65-specific cytotoxic T cells, among lymphocytes or CD8$^+$ T cells, after PBMCs of healthy blood donors having the HLA-A2 genotype were stimulated with the CMV$_P$495-503 peptide, which is a T-cell antigen epitope, and then amplified for 10-14 days, FIG. 10c showing the results of flow cytometry analysis of antigen phenotype and T-cell differentiation of the amplified CMV pp65-specific cytotoxic T cells in FIG. 10b;

FIG. 11a and FIG. 11b show the results of LDH (lactate dehydrogenase) assay to determine the effect of various inCT99†CMV fusion antibodies on the death of cancer cells by CMV pp65-specific cytotoxic T cells after treatment therewith, FIG. 11a showing a scheme for the mode of administration of the antibody and the CMV pp65-specific cytotoxic T cells for LDH assay, FIG. 11b being a graph analyzing the results of the LDH assay;

FIG. 12a to FIG. 12e show the results of LDH (lactate dehydrogenase) assay to determine the effect of the inCT99†CMV antibody and the control antibodies inCT99 (AAA)†CMV, Cetuximab†CMV, and Necitumumab†CMV on the death of cancer cells by CMV pp65-specific cytotoxic T cells after treatment therewith, FIG. 12a showing the results of LDH assay to determine the effect of the inCT99†CMV$_P$480-503 antibody and the control antibodies inCT99(AAA)†CMV$_P$480-503 and Cetuximab†CMV$_P$480-503 on the death of cancer cells by CMV pp65-specific cytotoxic T cells after treatment in the same manner as in FIG. 11a, FIG. 12b showing a scheme for LDH assay to determine the ability of the above antibodies to induce cancer cell death by CMV pp65-specific cytotoxic T cells after 24 hours of treatment therewith, FIG. 12c being a graph analyzing the results after LDH assay in the same manner as in FIG. 12b, FIG. 12d showing the results of LDH assay to determine the effect of the inCT99†CMV$_P$480-510 and the control antibodies inCT99(AAA)†CMV$_P$480-510 and Cetuximab†CMV$_P$480-510 on the death of cancer cells by CMV pp65-specific cytotoxic T cells after treatment in the same manner as in FIG. 11a, FIG. 12e showing the results of LDH assay to determine the effect of the inCT99†CMV$_P$480-516 antibody, the control antibodies inCT99(AAA)†CMV$_P$480-516 and Necitumumab†CMV$_P$480-516, and the Cetuximab†MMP14-CMV$_P$495-503 antibody on the death of cancer cells by CMV pp65-specific cytotoxic T cells after treatment in the same manner as in FIG. 11a;

FIG. 13a to FIG. 13d show the results of ELISA (enzyme-linked immunosorbent assay) quantification to determine IFN-g secretion of CMV pp65-specific cytotoxic T cells by treating cancer cells with a proteasome inhibitor and a Golgi inhibitor and then with the inCT99†CMV fusion antibody, FIG. 13a showing a scheme for the above assay, FIG. 13b showing the results of flow cytometry analysis to determine the purity of CMV pp65-specific cytotoxic T cells used for the assay;

FIG. 13c showing the results of ELISA quantification to determine the effect of proteasome and Golgi inhibitors on IFN-g secretion of CMV pp65-specific cytotoxic T cells by inCT99†CMV$_P$480-503 and the control antibodies inCT99 (AAA)†CMV$_P$480-503 and Cetuximab†CMV$_P$480-503, FIG. 13d showing the results of ELISA quantification to determine the effect of the inhibitors on IFN-g secretion of CMV pp65-specific cytotoxic T cells by the inCT99†CMV$_P$480-516, inCT99(AAA)†CMV$_P$480-516, and Necitumumab†CMV$_P$480-516 antibodies;

FIG. 14a to FIG. 14e show the results of measurement of the effect of the inCT99†CMV$_P$480-503 fusion antibody on inducing the inhibition of cancer cell growth by CMV pp65-specific cytotoxic T cells in NSG mice in which MDA-MB231 cells as human a breast cancer cell line were orthotopically xenografted into mammary fat pads, compared to the control antibodies inCT99(AAA)†CMV$_P$480-503 and Cetuximab†CMV$_P$480-503, FIG. 14a showing a scheme for the interval, dose, and mode of administration of antibody/IL-15/receptor complex molecules and the interval and mode of administration of CMV pp65-specific cytotoxic T cells after tumor transplantation in the above experiment, FIG. 14b being a graph showing a change in the tumor volume in each antibody-administered group depending on the date in the experiment of FIG. 14a, FIG. 14c being a graph showing weights of tumors extracted from killed mice 48 hours after the last administration of the antibody in the experiment of FIG. 14a, FIG. 14d being a photograph showing tumors extracted from killed mice 48 hours after the last administration of the antibody in the experiment of FIG. 14a, FIG. 14e being graphs showing changes in the tumor volume in each antibody-administered group depending on the date for each mouse in the experimental result of FIG. 14a;

FIG. 15a to FIG. 15e show the results of measurement of the effect of the inCT99†CMV$_P$480-516 fusion antibody on inducing the inhibition of cancer cell growth by CMV pp65-specific cytotoxic T cells in NSG mice in which MDA-MB231 cells as a human cancer breast cell line were orthotopically xenografted into mammary fat pads, compared to the Cetuximab†MMP14-CMV$_P$495-503 antibody used in conventional APEC technology, FIG. 15a being a scheme showing the interval, dose, and mode of administration of antibody/IL-15/receptor complex molecules and the interval and mode of administration of CMV pp65-specific cytotoxic T cells after tumor transplantation in the above experiment, FIG. 15b being a graph showing a change in the tumor volume in each antibody-administered group depending on the date in the experiment of FIG. 15a, FIG. 15c being a graph showing weights of tumors extracted from killed mice 48 hours after the last administration of the antibody in the experiment of FIG. 15a, FIG. 15d being a photograph showing tumors extracted from killed mice 48 hours after the last administration of the antibody in the experiment of FIG. 15a, FIG. 15e being graphs showing changes in the tumor volume in each antibody-administered group depending on the date for each mouse in the experimental result of FIG. 15a;

FIG. 16a to FIG. 16c show the results of measurement of the effect of the inCT99†CMV$_P$480-503 fusion antibody on activation of CMV pp65-specific cytotoxic T cells in NSG mice in which MDA-MB231 cells as a human breast cancer cell line were orthotopically xenografted into mammary fat pads, compared to the control antibodies inCT99(AAA) †CMV$_P$480-503 and Cetuximab†CMV$_P$480-503, FIG. 16a being a scheme showing the dose and mode of administration of the antibody and the mode of administration of CMV pp65-specific cytotoxic T cells after tumor transplantation in the above experiment, FIG. 16b showing the experimental results of flow cytometry analysis to determine the proportion of amplified CMV pp65-specific cytotoxic T cells for injection into NSG mice, FIG. 16c showing the results of analysis of the expression level of CD107 among CMV pp65-specific cytotoxic T cells and the proportion of CMV pp65-specific cytotoxic T cells expressing CD69 and IFN-g, after the mice in each administration group were killed and tumor-infiltrating lymphocytes were isolated;

FIG. 17a to FIG. 17c show the results of flow cytometry analysis to determine the ability of the inCT99†HPV$_E$11-19 and inCT99†HPV$_E$1-19 fusion antibodies to present the T-cell antigen epitope to HLA-A*02:01 through intracellular antigen processing, FIG. 17a showing a scheme for analyzing the ability of the antibodies to present the T-cell antigen epitope to HLA-A*02:01 through intracellular antigen processing at 37° C., FIG. 17*b* showing the results of flow cytometry analysis after treatment with the antibodies at various concentrations in the same manner as in FIG. 17*a*, FIG. 17*c* showing the results of flow cytometry analysis to determine the ability of the antibodies to present the T-cell antigen epitope to HLA-A*02:01 after treatment over time in the same manner as in FIG. 17*a;*

FIG. 18*a* and FIG. 18*b* show the results of flow cytometry analysis to determine the ability of various inCT99†OVA250-264 fusion antibodies to bind to cell-surface H-2K$^b$ and to present the T-cell antigen epitope to H-2K$^b$ through intracellular antigen processing and the results of LDH assay to determine the effect thereof on the death of cancer cells by OVA-specific cytotoxic T cells, FIG. 18*a* showing the results of flow cytometry analysis to determine the ability of the inCT99†OVA250-264 fusion antibody to bind to cell-surface H-2K$^b$ at 4° C. after treatment in the same manner as in FIGS. 9*a* and 9*b* and the ability of the inCT99†OVA250-264 fusion antibody to present the T-cell antigen epitope to H-2K$^b$ through intracellular antigen processing at 37° C., FIG. 18*b* showing the results of LDH assay to determine the effect of cancer cell death after H-2K$^b$-expressing MC38 cells were treated with the inCT99†OVA250-264 antibody and then with OVA-specific cytotoxic T cells in different amounts;

FIG. 19*a* to FIG. 19*c* show the results of measurement of the effect of the inCT99†OVA250-264 fusion antibody on inducing the inhibition of cancer cell growth by OVA257-264-specific cytotoxic T cells after MC38 cells as a mouse colorectal cancer cell line were allografted to the back of C57BL/6 immunocompetent mice, FIG. 19*a* showing a scheme for the interval, dose, and mode of administration of the antibody and the interval and mode of administration of OVA257-264-specific cytotoxic T cells after tumor transplantation in the above experiment, FIG. 19*b* being a graph showing a change in the tumor volume in each antibody-administered group depending on the date in the experiment of FIG. 18*a*, FIG. 19*c* being graphs showing changes in the tumor volume in each antibody-administered group for each mouse in the experiment of FIG. 19*b*; and FIG. 20 schematically shows the mechanism of action of a general-purpose therapeutic cancer vaccine by which a virus-specific epitope is expressed on the surface of cancer cells using a fusion antibody in which an antigen of virus-derived epitope peptide is fused to a cytosol-penetrating antibody and cancer cells are eliminated using virus-specific cytotoxic T cells already present in the tumor patient's body.

MODE FOR INVENTION

Unless otherwise defined, all technical and scientific terms used herein have the same meanings as those typically understood by those skilled in the art to which the present invention belongs. In general, the nomenclature used herein is well known in the art and is typical.

The present invention pertains to a fusion antibody in which a T-cell antigen epitope or a peptide comprising the same is fused to a cell- or tissue-specific cellular cytosol-penetrating antibody (cytotransmab) in order to deliver an antigen-derived CD8$^+$ T-cell antigen epitope or a peptide comprising the same to the cytosol of a target cell, and to a composition for presenting a CD8$^+$ T-cell antigen epitope to the surface of a target cell including the fusion antibody.

The present invention pertains to a method of delivering a CD8$^+$ T-cell antigen epitope or a peptide comprising the epitope into the cytosol in a form in which a CD8$^+$ T-cell antigen epitope or a peptide comprising the same is fused to a cytosol-penetrating antibody, in which the fusion antibody is endocytosed into the cell via the cytosol-penetrating antibody and is then localized in the cytosol through endosomal escape, thereby delivering the CD8$^+$ T-cell antigen epitope or the peptide comprising the same into the cytosol.

In the present invention, the target cell may include abnormal cells such as cancer cells, cells infected with viruses or pathogenic microorganisms, etc. that are not normal cells and are thus to be removed from the body, and may also be selected from the group consisting of mast cells, eosinophils, basophils, neutrophils, helper T cells (CD4$^+$ T cells), cytotoxic T cells (CD8$^+$ T cells), macrophages, epithelial cells, muscle cells, skin cells, and stem cells, but is not limited thereto. The target cell is not particularly limited, so long as it is an abnormally activated cell that causes a disease in the human body and needs to be removed from or treated in the body.

The target cell is preferably a cancer cell, virus, or pathogen, but is not limited thereto, and examples of the cancer cell include, but are not limited to, cells related to bladder cancer, breast cancer, stomach cancer, lung cancer, ovarian cancer, thyroid cancer, cervical cancer, central nerve cancer, glioblastoma, liver cancer, skin cancer, pancreatic cancer, stomach cancer, colorectal cancer, rectal cancer, esophageal cancer, kidney cancer, lung cancer, epithelial cancer, blood cancer, prostate cancer, soft tissue sarcoma, and the like.

Also, the virus or pathogen is not particularly limited, so long as it causes an infectious disease, which is a pathological condition caused by infection of the virus or pathogen, and examples thereof may include, but are not limited to, hepatitis B and C, human papilloma virus (HPV) infection, cytomegalovirus (CMV) infection, viral respiratory disease, influenza, and the like.

The fusion antibody according to the present invention expresses a virus-specific T-cell antigen epitope on the surface of a target cell and removes the target cell using virus-specific cytotoxic CD8$^+$ T cells already present in the patient's body.

Specifically, the fusion antibody according to the present invention is capable of penetrating a cytosol in a cell- or tissue-specific manner, and thus, after a penetration of the fusion antibody into the cytosol, virus-specific T-cell antigen epitope generated by a proteolytic system in the cytosol or a peptide comprising the same enters the endoplasmic reticulum, binds to MHC-I, and is secreted through the Golgi apparatus to thus express the virus-specific T-cell antigen epitope on the surface of a target cell, and the target cell expressing the virus-specific epitope is eliminated using virus-specific cytotoxic CD8$^+$ T cells already present in the tumor patient's body, so the fusion antibody of the present invention may be used as a general-purpose therapeutic antibody.

In addition, the present invention pertains to a pharmaceutical composition including a fusion antibody in which the antigen of virus-derived epitope peptide is fused to the cytosol-penetrating antibody, and a composition and method for treating a disease, particularly cancer, using the same.

In addition, the pharmaceutical composition for the treatment of cancer including the fusion antibody in which the antigen of virus-derived CD8$^+$ T-cell antigen epitope peptide is fused to the cytosol-penetrating antibody may be used for combination therapy with another anticancer agent, and the other anticancer agent is preferably, but is not limited to, cytotoxic CD8[+] T cells. Any anticancer agent that may be used in the art is useful for combination therapy.

In particular, when a pharmaceutical composition for cancer treatment including the fusion antibody in which the antigen of virus-derived epitope peptide is fused to the cytosol-penetrating antibody is used for combination therapy with cytotoxic T cells, cytotoxic T cells may be stimulated and thus cytokine secretion may be increased;

the number of cytotoxic T cells may be increased; and an increase in the influx of lymphocytes to the vicinity of the tumor may be induced.

The cytosol-penetrating antibody having cytosol-penetrating ability for the above purpose may be an intact immunoglobulin antibody or a fragment thereof (Korea Patent No. 10-1602870 (Method for cell penetration and cytosol localization of intact immunoglobulin antibody and use thereof)).

variable region (VL) and/or the heavy-chain variable region (VH) includes a WYWX sequence motif having endosomal escape activity, in which W is tryptophan, Y is tyrosine, and X is selected from the group consisting of methionine (M), isoleucine (I), and leucine (L), and 2) the first amino acid of the light-chain variable region (VL) and/or the heavy-chain variable region (VH) is aspartic acid (D) or glutamic acid (E).

The sequence information of the heavy chain and the light chain of the cytosol-penetrating antibody inCT99 having cytosol-penetrating ability for the above purpose may have the heavy-chain variable region sequence of SEQ ID NO: 1 and the light-chain variable region sequence of SEQ ID NO: 2, but is not limited thereto. Any sequence may be used without limitation, so long as it has cytosol-penetrating ability and/or endosomal escape activity suitable for the purpose of the present invention.

| Names of cytotransmab | Amino acid sequence | SEQ ID NO: |
|---|---|---|
| inCT99 heavy chain | 1 10 20 30 40 50 60<br>EVQLVESGGGLVQPGGSLRLSCAASGFTFSDFSMSWVRQAPGKGLEWVSYISRTSHTTYY<br>70 80 90 100 110 120<br>ADSVKGRFTISRDNSKNTLYLQMNSLRAEDTAVYYCARGWYWMDLWGQGTLVTVSSASTK<br>130 140 150 160 170 180<br>GPSVFPLAPSSKSTSGGTAALGCLVKDYFPEPVTVSWNSGALTSGVHTFPAVLQSSGLYS<br>190 200 210 220 230 240<br>LSSVVTVPSSSLGTQTYICNVNHKPSNTKVDKKVEPKSCDKTHTCPPCPAPEAAGGPSVF<br>250 260 270 280 290 300<br>LFPPKPKDTLMISRTPEVTCVVVDVSHEDPEVKFNWYVDGVEVHNAKTKPREEQYNSTYR<br>310 320 330 340 350 360<br>VVSVLTVLHQDWLNGKEYKCKVSNKALGAPIEKTISKAKGQPREPQVYTLPPSRDELTKN<br>370 380 390 400 410 420<br>QVSLTCLVKGFYPSDIAVEWESNGQPENNYKITPPVLDSDGSFFLYSKLTVDKSRWQQGN<br>430 440 446<br>VFSCSVMHEALHNHYTQKSLSLSPGK | 1 |
| inCT99 light chain | 1 10 20 30 40 50 60<br>SDGVRQCRGDCFDGPLMGSSSNDIQMTQSPSSLSASVGDRVTITCKSSQSLLNSRDGKNY<br>70 80 90 100 110 120<br>LAWYQQKPGKAPKLLIYDASNLETGVPSRFSGSGSGTDPTFTISSLQPEDIATYFCQQYW<br>130 140 150 160 170 180<br>YWMYTFGGGTKVEIKRTVAAPSVFIFPPSDEQLKSGTASVVCLLNNFYPREAKVQWKVQN<br>190 200 210 220 230 240 242<br>ALQSGNSQESVTEQDSKDSTYSLSSTLTLSKADYEKHKVYACEVTHQGLSSPVTKSFNRGEC | 2 |

The cytosol-penetrating antibody having cytosol-penetrating ability for the above purpose may be a chimeric, human, or humanized antibody.

The cytosol-penetrating antibody having cytosol-penetrating ability for the above purpose may be a tissue-specific cell-penetrating antibody having the ability to penetrate the cytosol of a target tissue cell by fusing a cyclic peptide that specifically binds to the surface membrane protein of a target cell to the N-terminus of the light-chain variable region (VL) and/or heavy-chain variable region (VH) of the antibody in an intact immunoglobulin antibody having endosomal escape activity at the light-chain variable domain (VL) and/or heavy-chain variable domain (VH) of the antibody.

The cytosol-penetrating antibody having endosomal escape activity for the above purpose may be a tissue-specific cytosol-penetrating antibody, the properties of which change under endosomal acidic pH conditions due to the following structure contained in the light-chain variable region and/or the heavy-chain variable region of the antibody: 1) the antigen-binding region 3 (complementarity-determining region 3, CDR3) sequence of the light-chain The amino acid residue numbers of all antibodies specified in SEQ ID NOs provided herein are based on the Kabat numbering scheme.

In an embodiment of the present invention, in order to impart tumor tissue specificity, an in4 cyclic peptide targeting integrin αvβ3 and αvβ5, which are strongly expressed in target cells such as cancer cells, was fused to the N-terminus of the light-chain variable region via a MGSSSN linker.

The sequence information of the in4 cyclic peptide for the above purpose is shown below.

| Name of cyclic peptide | Target receptor | Amino acid sequence | SEQ ID NO: |
|---|---|---|---|
| in4 | Integrin αvβ3/αvβ5 | DGVRQCRGDCFDGPL | 3 |

The fusion antibody in which the CD8[+] T-cell antigen epitope provided in the present invention or the peptide comprising the same is fused to the cell- or tissue-specific cytosol-penetrating antibody may be used as a vaccine that targets a target cell and presents a CD8$^+$ T-cell antigen epitope or a peptide comprising the same to MHC-I on the surface of the target cell.

According to the present invention, the fusion antibody in which the CD8$^+$ T-cell antigen epitope or the peptide comprising the epitope is fused to the cell- or tissue-specific cytosol-penetrating antibody is developed to target all cells having nuclei expressing MHC-I in addition to cancer cells, thereby presenting the CD8$^+$ T-cell antigen epitope to MHC-I on the target cell surface. When the cell- or tissue-specific cytosol-penetrating antibody of the present invention targets a certain cell or tissue, a method of delivering the CD8$^+$ T-cell antigen epitope antigen to the cytosol of all cells having nuclei expressing MHC-I, as well as cancer cells, is provided. Here, the cells other than cancer cells may be mast cells, eosinophils, basophils, neutrophils, helper T cells (CD4$^+$ T cells), cytotoxic T cells (CD8$^+$ T cells), macrophages, epithelial cells, muscle cells, skin cells, stem cells, etc.

The present invention pertains to a method of producing an antibody in which an epitope derived from viral proteins of cytomegalovirus (CMV), human papilloma virus 16 (HPV16), or Epstein-Barr virus (EBV) or a peptide comprising the epitope is fused to an inCT99 antibody having cell- or tissue-specific cytosol-penetrating ability.

As used herein, the term "fusion" refers to the integration of two molecules having the same or different functions or structures, preferably using a linker peptide, in which the linker peptide is able to mediate fusion of a virus-specific T-cell antigen epitope or a peptide comprising the same at various positions in each domain of an antibody of the present invention, an antibody, or a fragment thereof.

The virus-specific CD8$^+$ epitope peptide or a long peptide comprising the epitope was fused to the C-terminus of the inCT99 heavy chain using a G$_4$S linker or a GFLG linker.

In order to evaluate whether the antibody according to the present invention exhibits an improved anticancer effect compared to conventional APEC (antibody-peptide epitope conjugate) technology, a representative MMP14-specific linker, among the linkers used in APEC technology, was used. In APEC technology, a CMV-specific T-cell antigen epitope, that is, a CMV$_p$495-503 (NLVPMVATV) (SEQ ID NO: 13) peptide, is linked to a tumor surface antigen-targeting antibody via a cleavable linker that is cleaved by a protease that is expressed by a tumor cell or is present in a tumor, thus displaying a T-cell antigen epitope-MHC-I complex on the tumor cell surface.

In order to achieve the above purpose, exemplary linker sequence information is described below.

| Name of peptide linker | Symbol | Linker length | Amino acid sequence | SEQ ID NO: |
|---|---|---|---|---|
| G$_4$S | † | 5 amino acids | GGGGS | 4 |
| G$_4$SGFLG | ‡ | 9 amino acids | GGGGSGFLG | 5 |
| MMP14 | MMP14 | 8 amino acids | PRSAKLER | 6 |

The virus-specific CD8$^+$ T-cell antigen epitope, which is fused to the fusion antibody in which the antigen of virus-derived CD8$^+$ epitope peptide is fused to the cytosol-penetrating antibody, or a peptide comprising the same is represented as the sequence (SEQ ID NOs: 12-29) including 1) a group in which only a virus-specific CD8$^+$ T-cell antigen epitope of 9 amino acids is fused to the C-terminus of an inCT99 antibody, 2) a group in which the extended N-terminal fragment of a CD8$^+$ T-cell antigen epitope is fused thereto, 3) a group in which the extended C-terminal fragment of a CD8$^+$ T-cell antigen epitope is fused thereto, and 4) a group in which both the extended N-terminal and C-terminal fragments of a CD8$^+$ T-cell antigen epitope are fused thereto. Here, one CD8$^+$ T-cell antigen epitope or one peptide comprising the same may be directly fused to the C-terminus of the antibody.

Conventionally, only the antibody and the CD8$^+$ T-cell antigen epitope peptide portion, that is, a peptide composed of 8-11 amino acid residues directly binding to MHC-I, were linked through chemical conjugation by a disulfide bond (S—S bond). Specifically, the antibody and the peptide are prepared separately, the linker peptide is used to connect the same, and the peptide is cleavable in a specific environment. However, according to the present invention, there is a difference in that the CD8$^+$ T-cell antigen epitope peptide is directly linked to the C-terminus of the antibody heavy chain through genetic fusion without cysteine (Cys).

In the present invention, an inCT(AAA)†CMV antibody and Cetuximab†CMV and Necitumumab†CMV fusion antibodies were used as negative control antibodies not having cytosol-penetrating ability.

The inCT(AAA)†CMV antibody is configured such that $^{92}$WYW$^{94}$, which is an endosomal escape motif present in VL-CDR3 of the inCT99 antibody, is mutated to $^{92}$AAA$^{94}$, and $^{95}$WYW$^{98}$, which is an endosomal escape motif present in VH-CDR3 thereof, is mutated to $^{95}$AAA$^{98}$. Therefore, the inCT(AAA)†CMV antibody, which is endocytosed by binding to integrin $\alpha v\beta 3$ and $\alpha v\beta 5$ receptors, does not penetrate the cytosol because it does not escape from the endosome, and thus cannot present a virus-specific T-cell antigen epitope on the cell surface.

The Cetuximab†CMV fusion antibody is constructed by fusing a virus-specific T-cell antigen epitope or a peptide comprising the same to the C-terminus of the heavy-chain region of the EGFR-targeting Cetuximab antibody via a G$_4$S linker. Since the Cetuximab†CMV fusion antibody binds to EGFR and is endocytosed and then degraded by lysosomes, it does not have the ability to present a virus-specific T-cell antigen epitope on the cell surface due to penetration into the cytosol.

The Necitumumab†CMV fusion antibody is constructed by fusing a virus-specific T-cell antigen epitope or a peptide comprising the same to the C-terminus of the heavy-chain region of the EGFR-targeting Necitumumab antibody via a G$_4$S linker. Since the Necitumumab†CMV fusion antibody binds to EGFR and is endocytosed and then degraded by lysosomes, it does not have the ability to present a virus-specific T-cell antigen epitope on the cell surface due to penetration into the cytosol.

In order to evaluate whether the antibody according to the present invention exhibits an improved anticancer effect compared to conventional APEC (antibody-peptide epitope conjugate) technology, a representative Cetuximab†MMP14-CMV$_p$495-503 antibody, among the antibodies used in APEC technology, was constructed. In APEC technology, a CMV-specific T-cell antigen epitope, that is, a CMV$_p$495-503 (NLVPMVATV) (SEQ ID NO: 13) peptide, is linked to a tumor surface antigen-targeting antibody via a cleavable linker that is cleaved by a protease that is expressed by a tumor cell or is present in a tumor, thus displaying a T-cell antigen epitope-MHC-I complex on the tumor cell surface.

The sequence information of the heavy-chain variable region and the light-chain variable region of each of the Cetuximab and Necitumumab antibodies, which are control antibodies described above, is shown in SEQ ID NOs: 7-10 below.

| Antibody | Name of variable regions | Amino acid sequence | SEQ ID NO: |
|---|---|---|---|
| Cetuximab | VH | 1     10     20     30     40     50     60<br>QVQLKQSGPGLVQPSQSLSITCTVSGFSLTNYGVHWVRQSPGKGLEWLGVIWSGGNTDYN<br>70     80     90     100     110     119<br>TPFTSRLSINKDNSKSQVFFKMNSLQSNDTAIYYCARALTYYDYEFAYWGQGTLVTVSA | 7 |
| | VL | 1     10     20     30     40     50     60<br>DILLTQSPVILSVSPGERVSFSCRASQSIGTNIHWYQQRTNGSPRLLIKYASESISGIPS<br>70     80     90     100     108<br>RFSGSGSGTDFTLSINSVESEDIADYYCQQNNNWPTTFGAGTKLELKR | 8 |
| Necitumumab | VH | 1     10     20     30     40     50     60<br>QVQLQESGPGLVKPSQTLSLTCTVSGGSISSGDYYWSWIRQPPGKGLEWIGYIYYSGSTD<br>70     80     90     100     110     120<br>YNPSLKSRVTMSVDTSKNQFSLKVNSVTAADTAVYYCARVSIFGVGTFDYWGQGTLVTVS<br>121<br>S | 9 |
| | VL | 1     10     20     30     40     50     60<br>EIVMTQSPATLSLSPGERATLSCRASQSVSSYLAWYQQKPGQAPRLLYDASNRATGIPA<br>70     80     90     100     108<br>RFSGSGSGTDFTLTISSLEPEDFAVYYCHQYGSTPLTFGGGTKAEIKR | 10 |

The sequence information of the heavy-chain constant region and light-chain constant region of human IgG1 used to produce the Cetuximab and Necitumumab antibodies, which are the control antibodies described above, is described below. In order to exclude cancer cell inhibitory activity due to antibody-dependent cell cytotoxicity (ADCC), a heavy chain named hIgG1 (AAG) in which lysine at positions 234 and 235 in the heavy-chain CH2-CH3 region is substituted with alanine and in which proline at position 329 is substituted with glycine was used.

| Names of constant regions | Amino acid sequence | SEQ ID NO: |
|---|---|---|
| Human IgG1 heavy chain constant region (AAG) | 1     10     20     30     40     50     60<br>ASTKGPSVFPLAPSSKSTSGGTAALGCLVKDYFPEPVTVSWNSGALTSGVHTFPAVLQSS<br>70     80     90     100     110     120<br>GLYSLSSVVTVPSSSLGTQTYICNVNHKPSNTKVDKKVEPKSCDKTHTCPPCPAPEAAGG<br>130     140     150     160     170     180<br>PSVFLFPPKPKDTLMISRTPEVTCVVVDVSHEDPEVKFNWYVDGVEVHNAKTKPREEQYN<br>190     200     210     220     230     240<br>STYRVVSVLTVLHQDWLNGKEYKCKVSNKALGAPIEKTISKAKGQPREPQVYTLPPSRDE<br>250     260     270     280     290     300<br>LTKNQVSLTCLVKGFYPSDIAVEWESNGQPENNYKTTPPVLDSDGSFFLYSKLTVDKSRW<br>310     320     330<br>QQGNVFSCSVMHEALHNHYTQKSLSLSPGK | 11 |
| Human IgG1 light chain constant region | 1     10     20     30     40     50     60<br>RTVAAPSVFIFPPSDEQLKSGTASVVCLLNNFYPREAKVQWKVONALQSGNSQESVTEQD<br>70     80     90     100     107<br>SKDSTYSLSSTLTLSKADYEKHKVYACEVTHQGLSSPVTKSFNRGEC | 12 |

The inCT99†CMV fusion antibody and the control antibodies produced through the above method are named as set forth below.

| Origin of viral antigen | | Name of T cell epitope-fused cytotransmab | Ag residue number | HCMV pp65-derived peptides | SEQ ID No |
|---|---|---|---|---|---|
| CMV pp65 | 9mer epitope | inCT99†CMV$_p$495-503<br>inCT99‡CMV$_p$495-503<br>Cetuximab†MMP14-CMV$_p$495-503 | 495-503 | NLVPMVATV | 13 |
| | C-term extended | inCT99†CMV$_p$495-508 | 495-508 | NLVPMVATVQGQNLKY | 14 |
| | N-term extended | inCT99†CMV$_p$480-503<br>inCT99‡CMV$_p$480-503<br>Cetuximab†CMV$_p$480-503<br>inCT99(AAA)†CMV$_p$480-503 | 480-503 | AVFTWPPWQAGILARNLVPMVATV | 15 |

-continued

| Origin of viral antigen | | Name of T cell epitope-fused cytotransmab | Ag residue number | HCMV pp65-derived peptides | SEQ ID No |
|---|---|---|---|---|---|
| N-term end C-term extended | | inCT99†$CMV_p$480-504 | 480-504 | AVFTWPPWQAGILARNLVPMVATVQ | 16 |
| | | inCT99†$CMV_p$480-505 | 480-505 | AVFTWPPWQAGILARNLVPMVATVQG | 17 |
| | | inCT99†$CMV_p$480-506 | 480-506 | AVFTWPPWQAGILARNLVPMVATVQGQ | 18 |
| | | inCT99†$CMV_p$480-507 | 480-507 | AVFTWPPWQAGILARNLVPMVATVQGQN | 19 |
| | | inCT99†$CMV_p$480-508 | 480-508 | AVFTWPPWQAGILARNLVPMVATVQGQNL | 20 |
| | | inCT99†$CMV_p$480-509 | 480-509 | AVFTWPPWQAGILARNLVPMVATVQGQNLK | 21 |
| | | inCT99†$CMV_p$480-510 Cetuximab†$CMV_p$-480-510 inCT99(AAA)†$CMV_p$480-510 | 480-510 | AVFTWPPWQAGILARNLVPMVATVQGQNLKY | 22 |
| | | inCT99†$CMV_p$480-511 | 480-511 | AVFTWPPWQAGILARNLVPMVATVQGQNLKYQ | 23 |
| | | inCT99†$CMV_p$480-512 | 480-512 | AVFTWPPWQAGILARNLVPMVATVQGGNLKYQE | 24 |
| | | inCT99†$CMV_p$480-513 | 480-513 | AVFTWPPWQAGILARNLVPMVATVQGGNLKYQEF | 25 |
| | | inCT99†$CMV_p$480-516 Necitumumab†$CMV_p$480-518 inCT99(AAA)†$CMV_p$480-516 | 480-516 | AVFTWPPWQAGILARNLVPMVATVQGQNLKYQSFFWD | 26 |
| | | inCT99†$CMV_p$480-519 | 480-519 | AVFTWPPWQAGILARNLVPMVATVQGQNLKYQEFFWDAND | 27 |
| | | inCT99†$CMY_p$490-508 | 490-508 | GILARNLVPMVATVQGQNL | 28 |

†: G4S linker (non-cleavable linker)
‡: GFLG linker (cleavabie linker)
MMP14: Metrix metalloprotease 14 sensitive linker The inCT99†HPV and inCT99†EBV fusion antibodies produced through the above method are named as set forth below. The sequence of the Epstein-Barr virus (EBV)-derived T-cell antigen epitope EBV L2 426-434 is CLG-GLLTMV, but the sequence SLGGLLTMV of EBV L2 426-434 (C426S) in which the residue at position 426 is substituted with Ser in order to prevent oligomerization due to a Cys residue upon fusion to the inCT99 antibody was used.

| Origin of viral antigen | | Name of T cell epitope-fused cytotransmab | Ag residue number | HCMV pp65-derived peptides | SEQ ID No |
|---|---|---|---|---|---|
| HPV E7 | 9 mer epitope | inCT99†$HPV_E$11-19 inCT99‡$HPV_E$11-19 | 11-19 | YMLDLQPET | 29 |
| | N-term extended | inCT99†$HPV_E$1-19 inCT99‡$HPV_E$1-19 | 1-19 | MHGDTPTLHEYMLDLQPET | 30 |
| EBV LMP2 | 9 mer epitope | inCT99†$EBV_{12}$356-364 | 356-364 | FLVALALLL | 31 |
| | | inCT99†$EBV_{12}$426-364* | 426-434(C426S) | SLGGLLTMV | 32 |
| | | inCT99‡$EBV_{12}$426-364* | 426-434(C426S) | | 33 |
| | N-term extended | inCT99†$EBV_{12}$417-434* | 417-434(C426S) | NRTYGPVFMSLGGLLTMV | 34 |
| | | inCT99†$EBV_{12}$413-434* | 413-434(C426S) | WGSGNRTVGPVFMSLGGLLTMV | 35 |
| | | inCT99†$EBV_{12}$409-434* | 409-434(C426S) | ILTEWGSGNRTYGPVFMSLGGLLTMV | 38 |

†: G4S linker (non-cleavable linker)
‡: GFLG linker (cleavabie linker)

In the present invention, H9 shown in the table above is the TCR-like antibody used to analyze whether the CMV epitope forms a complex with HLA-A2 to present the viral epitope on the cell surface in practice after treating tumor cells with the inCT†CMV fusion antibody in which the CMV antigen-derived CD8[+] epitope peptide is fused to the cytosol-penetrating antibody.

In an embodiment of the present invention, antibodies having improved affinity to the complex of $CMV_p$495-503 and HLA-A2 are H9#1, H9#38, and C1-17.

The TCR-like antibody for analyzing the complex of HPV epitope and HLA-A2 is 7-1, and the TCR-like antibody for analyzing the complex of EBV epitope and HLA-A2 is L2.

The sequences of the heavy-chain variable region, light-chain variable region, mouse IgG2a heavy-chain constant region, and mouse IgG2a light-chain constant region used to produce the TCR-like antibody are shown below.

| Neme of TCR-like antibody | Variable region | Amino acid sequence | SEQ ID NO: |
|---|---|---|---|
| H9 | VH | 1    10    20    30    40    50    60<br>EVQLVQSGAEVKKPGSSVKVSCKASGGTFSSYAISWVRQAPGQGLEWMGGIIPIFGTANNY<br>      70    80    90    100    110    120<br>AQKFQGRVTITADESTSTAVMELSSLRSEDTAVYYCARGDLYYYDSSGVPRYVFDYWGQG<br>      127<br>TLVTVSS | 37 |
| | VL | 1    10    20    30    40    50    60<br>ETTLTQSPGTLSLSPGERATLSCRASQSVSSSYLAWVQQKPGQAPRLVIYGASSRATGIP<br>      70    80    90    100    110<br>DRFSGSGSGTDFTLTISRLEPEDFAVYYCQHVSTSPGFTFGQGTKLEIRR | 38 |
| H9 #1 | VH | 1    10    20    30    40    50    60<br>EVQLVQSGAEVKKPGSSVKVSCKASGGTFSSVAISWVRQAPGQGLEWMGGIIPIFGTANY<br>      70    80    90    100    110    120<br>AQKFQGRVTITADESTSTAYMELSSLRSEDTAVYYCARGDLYYYDSSGYPLWVMDYWGQG<br>      127<br>TLVTVSS | 39 |
| | VL | 1    10    20    30    40    50    60<br>ETTLTQSPGTLSLSPGERATLSCRASQSVSSSYLAWYQQKPGQAPRLVIYGASSRATGIP<br>      70    80    90    100    110<br>DRFSGSGSGTDFTLTISRLEPEDFAVYYCQDVSTYPAFTFGQGTKLEIRR | 40 |
| H9 #38 | VH | 1    10    20    30    40    50    60<br>EVQVQSGAEVKKPGSSVKVSCKASGGTFSSYAISWVRQAPGQGLEWMGGIIPIFGTANY<br>      70    80    90    100    110    120<br>AQKFQGRVTITADESTSTAYMELSSLRSEDTAVYYCARGDLYYYDSSGYPWYYMDYWGQG<br>      127<br>TLVTVSS | 41 |
| | VL | 1    10    20    30    40    50    60<br>ETLLTQSPGTLSLSPGERATLSCRASQSVSSSYLAWYQQKPGQAPRLVIYGASSRATGIP<br>      70    80    90    100    110<br>DRFSGSGSGTDFTLTSRLEPEDFAYYYCQHSVAFPGFTFGQGTKLEIRR | 42 |
| C1-17 | VH | 1    10    20    30    40    50    60<br>EVQLVQSGAEVKKPGSSVKVSCKASGGTFSSYAISWVRQAPGQGLEWMGSIIPIFGVAEY<br>      70    80    90    100    110    120<br>AHKFQGRVTITADESTSTAYMELSSLRSEDTAVYYCARGDLYYYDSSGYPLWYMDYWGQG<br>      127<br>TLVTVSS | 43 |
| | VL | 1    10    20    30    40    50    60<br>ETTLTQSPGTLSLSPGERATLSCRASQSVSSSVLAWYQQKPGQAPRLYIYGASTRPTGIP<br>      70    80    90    100    110<br>DRFSGSGSGTDFTLTISRLEPEDFAVYYCQDYSTYPAFTFGQGTKLEIRR | 44 |

| Name of TCR-like antibody | Variable region | Amino acid sequence | SEQ ID NO: |
|---|---|---|---|
| 7-1 | VH | 1    10    20    30    40    50    60<br>QVQLOGWGAGLLKPSETLSLTCAVYGGSFSGYYWSWIRQPPGKGLEWIGEINHSGSTNYN<br>      70    80    90    100    110    118<br>PSLKSRVTISVDTSKNQFSLKLSSVTAADTAVYYCARAPQSWYRGDVWGQGTLVTVSS | 45 |
| | VL | 1    10    20    30    40    50    60<br>SYELTQPPSVSGTPGQRVAISCSGSSSNIGTAMVTWYQHVPGTAPKLLIFNNNQRPSGVP<br>      70    80    90    100    110<br>DRFSASKSGTSASLAIIGLQSDDEADYYCAAWDDNLKSYVFGTGTKVIVL | 46 |
| L2 | VH | 1    10    20    30    40    50    60<br>QVQLKQSGPGLVQPSQSLSITCTVSGFSLTNYGVHWVRQSPGKGLEWLGVIWSGGSTDYN<br>      70    80    90    100    110    117<br>AAFISRLSISKDNSKSQVFFKMNSLQANDTAIYYCARNWPYYFDYWGQGTTLTVSS | 47 |
| | VL | 1    10    20    30    40    50    60<br>DIVMTQSQKFMSTSVGDRVSVTCRASQNVFTNVAWYQQKPGQAPKALIYSTSYRYSGVPD<br>      70    80    90    100    108<br>RFTGSGSGTDFTLTISNVQSEDLAEYFCQQYISYPLTFGAGTKLELKR | 48 |

| Names of constant regions | Amino acid sequence | SEQ ID NO: |
|---|---|---|
| Mouse IgG2a heavy chain constant region | 1    10    20    30    40    50    60<br>AKTTAPSVYPLAPVCGDTTGSSVTLGCLVKGYFPEPVTLTWNSGSLSSGVHTFPAVLQSD<br>70    80    90    100    110    120<br>LYTLSSSVTVTSSTWPSQSITCNVAHPASSTKVDKKIEPRGPTIKPCPPCKCPAPNLLGG<br>130    140    150    160    170    180<br>PSVFIFPPKIKDVLMISLSPIVTCVVVDVSEDDPDVQISWFVNNVEVHTAQTQTHREDYN<br>190    200    210    220    230    240<br>STLRVVSALPIQHQDWMSGKEFKCKVNNKDLPAPIERTISKPKGSVRAPQVYVLPPPEEE<br>250    260    270    280    290    300<br>MTKKQVTLTCMVTDFMPEDIYVEWTNNGKTELNYKNTEPVLDSDGSYFMYSKLRVEKKNW<br>310    320    330<br>VERNSYSCSVVHEGLHNHHTTKSFSRTPGK | 48 |
| Mouse C kappa light chain constant region | 1    10    20    30    40    50    60<br>ADAAPTVSIFPPSSEQLTSGGASVVCFLNNFYPKDINVKWKIDGSERQNGVLNSWTDQDS<br>70    80    90    100    106<br>KDSTYSMSSTLTLTKDEYERHNSYTCEATHKTSTSPIVKSFNRNEC | 50 |

A conventional mechanism by which the CD8$^+$ T-cell antigen epitope is cleaved in the antibody-T-cell antigen epitope fusion and displayed to MHC-I is one in which the cleavable linker is cleavable in an intracellular or extracellular environment (a low-pH reducing environment) to thus expose the T-cell epitope peptide, which then binds to MHC-I in the endosome or on the cell surface, particularly one in which peptide/MHC-I is bound on the cell surface or in the endosome and is presented on the cell surface.

However, according to the present invention, the antibody-peptide is cleaved through antigen-processing machinery (original cellular mechanism) after penetration of the fusion antibody into the cytosol, and the T-cell antigen epitope or the peptide comprising the epitope enters the ER from the cytosol, binds to MHC-I, and is presented. Briefly, the T-cell antigen epitope peptide is generated in the cytosol, enters the ER, binds to MHC-I, and is presented on the cell surface. More briefly, it follows the peptide/MHC-I presentation mechanism occurring in the cell.

According to the conventional mechanism, when a non-cleavable linker is used, the T-cell antigen epitope peptide is not presented to MHC-I, and when the antibody is linked with a longer peptide than the T-cell epitope peptide (a peptide composed of 8-11 amino acid residues that actually bind to MHC-I), presentation to MHC-I is impossible. This is because intracellular antigen processing in the cytosol is not performed. Moreover, the T-cell antigen epitope or peptide must necessarily include cysteine in order to be conjugated to the antibody through a disulfide bond (S—S bond), which is undesirable.

However, according to the present invention, since the antigen-processing machinery of the cell is used, two non-cleavable/cleavable linkers may be used, and even when a longer peptide than the T-cell antigen epitope peptide (8-11 amino acid residues) is fused, presentation to MHC-I is possible, and the peptide portion does not require cysteine by virtue of genetic fusion.

In addition, the present invention pertains to a method of inhibiting the growth of cancer or tumor cells using the fusion antibody in which the CD8$^+$ T-cell antigen epitope is fused to the cytosol-penetrating antibody, and a method of treating cancer or tumors.

The cancer may be selected from the group consisting of squamous cell carcinoma, small cell lung cancer, non-small cell lung cancer, adenocarcinoma of the lung, squamous cell carcinoma of the lung, peritoneal cancer, skin cancer, skin or intraocular melanoma, rectal cancer, perianal cancer, esophageal cancer, small intestine cancer, endocrine adenocarcinoma, parathyroid cancer, adrenal cancer, soft tissue sarcoma, urethral cancer, chronic or acute leukemia, lymphocytic lymphoma, hepatocellular carcinoma, gastrointestinal cancer, pancreatic cancer, glioblastoma, cervical cancer, ovarian cancer, liver cancer, bladder cancer, liver tumors, breast cancer, colon cancer, colorectal cancer, endometrial or uterine cancer, salivary gland cancer, kidney cancer, liver cancer, prostate cancer, vulvar cancer, thyroid cancer, liver cancer, and head and neck cancer.

In addition, the present invention pertains to a method of treating an infectious disease using the fusion antibody in which the CD8$^+$ T-cell antigen epitope is fused to the cytosol-penetrating antibody.

The infectious disease may be a pathological condition caused by infection with a virus or pathogen, and may include, for example, hepatitis B and c, human papilloma virus (HPV) infection, cytomegalovirus (CMV) infection, Epstein-Barr virus (EBV) infection, viral respiratory diseases, influenza, etc., but is not limited thereto.

The pharmaceutical composition for preventing or treating cancer or an infectious disease may be administered orally or parenterally. For parenteral administration, intravenous injection, subcutaneous injection, intramuscular injection, intraperitoneal injection, endothelial administration, topical administration, intranasal administration, intrapulmonary administration, intrarectal administration, etc. may be carried out. Upon oral administration, the protein or peptide is digestible and therefore an oral composition has to be formulated in order to coat the active agent or to protect the same from degradation in the stomach. Moreover, the composition may be administered using any device capable of transporting the active material to a target cell.

When the composition is prepared as a pharmaceutical composition for the prevention or treatment of cancer or an infectious disease, the composition may include a pharmaceutically acceptable carrier. Pharmaceutically acceptable carriers that may be contained in the composition include, but are not limited to, those commonly used in formulations, for example, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, and the like. The pharmaceutical composition may further include a lubricant, a wetting agent, a sweetener, a flavoring agent, an emulsifier, a suspension agent, a preservative, and the like, in addition to the above components.

The pharmaceutical composition for preventing or treating cancer or an infectious disease may be administered orally or parenterally. For parenteral administration, intravenous injection, subcutaneous injection, intramuscular injection, intraperitoneal injection, endothelial administration, topical administration, intranasal administration, intrapulmonary administration, intrarectal administration, etc. may be carried out. Upon oral administration, the protein or peptide is digestible and therefore an oral composition has to be formulated in order to coat the active agent or to protect the same from degradation in the stomach. Moreover, the composition may be administered using any device capable of transporting the active material to a target cell.

Suitable dosages of the pharmaceutical composition for the prevention or treatment of cancer or an infectious disease may be determined in various ways depending on factors including the formulation method, the mode of administration, the patient's age, body weight, gender, and pathologic status, diet, the time of administration, the route of administration, the rate of excretion, and reaction sensitivity. A preferred dosage of the composition falls in the range of 0.001-100 mg/kg for an adult. The "pharmaceutically effective amount" is an amount sufficient to prevent or treat cancer, or to prevent or treat a disease caused by angiogenesis.

The present invention pertains to a polynucleotide or nucleic acid encoding the fusion antibody including the cell- or tissue-specific cytosol-penetrating antibody and the T-cell antigen epitope or the peptide comprising the same fused thereto.

The "polynucleotide" or "nucleic acid" is a polymer of deoxyribonucleotides or ribonucleotides in single-stranded or double-stranded form. It encompasses RNA genomic sequences and DNA (gDNA and cDNA) and RNA sequences transcribed therefrom, and includes analogues of natural polynucleotides, unless otherwise specified.

The polynucleotide includes a nucleotide sequence encoding a recombinant immunotoxin in a form in which the cytosol-penetrating antibody and human RNAase are fused to each other, and also a sequence complementary to the sequence. The complementary sequence includes not only perfectly complementary sequences, but also substantially complementary sequences.

The nucleotides according to the present invention may be modified. Such modifications include addition and deletion of nucleotides. A polynucleotide encoding the amino acid sequence is to be understood as including a nucleotide sequence exhibiting substantial identity to the nucleotide sequence. When the nucleotide sequence of the present invention and any other sequence are aligned so as to correspond to each other as closely as possible and the aligned sequence is analyzed using an algorithm commonly used in the art, "substantial identity" refers to a sequence exhibiting at least 80% homology, at least 90% homology, or at least 95% homology.

In an embodiment of the present invention, a method of producing a fusion antibody (a viral epitope-fused cytotransmab) in which an antigen of virus-derived epitope peptide, in which a virus-specific T-cell antigen epitope or a peptide comprising the same is fused to the C-terminus of a human heavy-chain variable region (VH) region and heavy-chain constant region having cytosol-penetrating ability and a human light-chain variable region (VL) having tumor-tissue-specific cytosol-penetrating ability, is fused to a cytosol-penetrating antibody, includes:

1) preparing a heavy-chain expression vector of the fusion antibody in which an antigen of virus-derived epitope peptide is fused to a cytosol-penetrating antibody by cloning nucleic acids in which a virus-specific T-cell antigen epitope or a peptide comprising the same is fused to the C-terminus of a heavy chain including the human heavy-chain variable region (VH) and human heavy-chain constant region (CH1-hinge-CH2-CH3) having cytosol-penetrating ability;

2) preparing a cytosol-penetrating light-chain expression vector cloned with nucleic acids in which the light-chain variable region (VL) of a light chain including the human light-chain variable region (VL) and human light-chain constant region (CL) is substituted with a cytosol-penetrating humanized light-chain variable region (VL) and a humanized light-chain variable region (VL) having tumor-tissue-specific cytosol-penetrating ability;

3) expressing a fusion antibody in which an antigen of virus-derived epitope peptide is fused to a cytosol-penetrating antibody, capable of expressing a viral epitope in target cells so as to be recognized by virus-specific cytotoxic T cells already present in the tumor patient's body by co-transfecting animal cells for protein expression with the heavy-chain and light-chain expression vectors prepared above; and 4) purifying and recovering the expressed antibody in an intact immunoglobulin form.

In the method, it is possible to express a general-purpose therapeutic antibody in which the antibody penetrates the cell in a tumor-tissue-specific manner using the heavy-chain expression vector and the light-chain expression vector and a virus-specific epitope generated by a proteolytic system in the cytosol after penetration into the cytosol enters the endoplasmic reticulum, binds to MHC-I, and is secreted through the Golgi apparatus to express a virus-specific epitope on the surface of target cells and to eliminate target cells expressing the virus-specific epitope using virus-specific cytotoxic T cells already present in the tumor patient's body. The vector may be a vector system in which the light chain and the heavy chain are expressed simultaneously in one vector or in separate vectors. In the latter case, both vectors may be introduced into the host cell through co-transfection and targeted transfection.

In the recombinant vector, the light-chain variable region (VL), the light-chain constant region (CL), the heavy-chain variable region (VH), and the heavy-chain constant region (CH1-hinge-CH2-CH3) according to the present invention may be operatively linked to a promoter. Here, the term "operatively linked" refers to a functional linkage between a nucleotide expression control sequence (e.g. a promoter sequence) and another nucleotide sequence. Thus, the control sequence is capable of regulating transcription and/or translation of the other nucleotide sequence.

The recombinant vector may typically be constructed as a vector for cloning or a vector for expression. The expression vector may be a typical vector used to express a foreign protein in plants, animals, or microorganisms in the art. The recombinant vector may be constructed through various methods known in the art.

The recombinant vector may be constructed using a prokaryotic cell or a eukaryotic cell as a host. For example, when the vector that is used is an expression vector and a prokaryotic cell is used as a host, a strong promoter capable of promoting transcription (e.g. a pLλ promoter, trp promoter, lac promoter, tac promoter, T7 promoter, etc.), a ribosome-binding site for initiation of translation, and a transcription/translation termination sequence are generally included. When a eukaryotic cell is used as a host, the origin of replication operating in the eukaryotic cell included in the vector includes, but is not limited to, the f1 origin of replication, the SV40 origin of replication, the pMB1 origin of replication, the adeno origin of replication, the AAV origin of replication, the CMV and origin of replication, the BBV origin of replication. Moreover, promoters derived from the genome of or mammalian cells (e.g. metallothionine promoter) promoters derived from mammalian viruses (e.g. adenovirus late promoter, vaccinia virus 7.5K promoter, SV40 promoter, cytomegalovirus (CMV) promoter, and tk promoter of HSV) may be used, and a polyadenylation sequence is generally used as a transcription termination sequence.

In addition, the present invention pertains to a host cell transformed with the recombinant vector.

As the host cell, any host cell known in the art may be used, and examples of the prokaryotic cell include *E. coli* JM109, *E. coli* BL21, *E. coli* RR1, *E. coli* LE392, *E. coli* B, *E. coli* X 1776, *E. coli* W3110, *Bacillus* genus strains such as *Bacillus subtilis* or *Bacillus thuringiensis*, Enterobacteriaceae strains such as *Salmonella typhimurium, Serratia marcescens*, and various *Pseudomonas* species, and the like. In the case of transfection into eukaryotic cells, as a host cell, yeast (*Saccharomyces cerevisiae*), insect cells, plant cells, and animal cells, for example, SP2/0, CHO (Chinese hamster ovary) K1, CHO DG44, PER.C6, W138, BHK, COS-7, 293, HepG2, Huh7, 3T3, RIN, and MDCK cell lines, may be used.

In addition, the present invention pertains to a method of producing a general-purpose therapeutic antibody including culturing the host cell, in which the antibody penetrates cells in a cell- or tissue-specific manner and a virus-specific epitope generated by a proteolytic system in the cytosol after penetration into the cytosol enters the endoplasmic reticulum, binds to MHC-I, and is secreted through the Golgi apparatus to express a virus-specific epitope on the surface of target cells and to eliminate target cells expressing the virus-specific epitope using virus-specific cytotoxic T cells already present in the tumor patient's body.

Insertion of the recombinant vector into the host cell may be carried out using an insertion method well known in the art. For the transport method, for example, when the host cell is a prokaryotic cell, a method using $CaCl_2$) or an electroporation method may be performed, and when the host cell is a eukaryotic cell, a microinjection method, calcium phosphate precipitation method, electroporation method, liposome-mediated transfection method, or gene bombardment method may be performed, but the present invention is not limited thereto. The use of microorganisms such as *E. coli* may result in high productivity compared to when using animal cells, etc. Although not suitable for the production of an intact Ig antibody due to glycosylation problems, such microorganisms are potentially useful for the production of antigen-binding fragments such as Fab and Fv.

The method of selecting the transformed host cell may be easily performed according to a method well known in the art using the phenotype expressed by the selective marker. For example, when the selective marker is a specific antibiotic resistance gene, a transformant may be easily selected by culturing the transformant in a medium containing the antibiotic.

The present invention pertains to a general-purpose therapeutic vaccine capable of eliminating a target cell using virus-specific cytotoxic T cells already present in a patient's body, as well as expressing a virus-specific epitope on the surface of a target cell using a fusion antibody (viral epitope-fused cytotransmab) in which a virus antigen-derived epitope peptide in which a virus-specific T-cell antigen epitope or a peptide comprising the same is fused to the C-terminus of the heavy-chain region of an antibody (immunoglobulin) having cell- or tissue-specific cytosol-penetrating ability is fused to a cytosol-penetrating antibody.

The virus-specific $CD8^+$ T-cell antigen epitope or the peptide comprising the same may be linked to Fc, an antibody, or an antibody fragment through linker-mediated coupling, chemical linkage, genetic fusion, or the like.

In the present invention, the "heavy-chain constant region" refers to a region including an antibody-derived CH2 domain, CH3 domain, and hinge domain. However, in the case of IgE, it means a region including a CH2 domain, a CH3 domain, a CH4 domain, and a hinge domain.

The heavy-chain constant region may be any one isotype selected from among gamma ($\gamma$), mu ($\mu$), alpha ($\alpha$), delta ($\delta$), and epsilon ($\epsilon$), and may have gamma1 ($\gamma$1), gamma2 ($\gamma$2), gamma3 ($\gamma$3), gamma4 ($\gamma$4), alpha1 ($\alpha$1), and alpha2 ($\alpha$2) subclasses. The light-chain constant region may be a kappa or lambda type.

As used herein, the term "heavy chain" is understood to include a full-length heavy chain and fragments thereof, the full-length heavy chain including a variable region domain VH including an amino acid sequence having a variable region sequence sufficient to confer specificity to an antigen and three constant region domains CH1, CH2, and CH3. Also, the term "light chain" is understood to include a full-length light chain and fragments thereof, the full-length light chain including a variable region domain VL including an amino acid sequence having a variable region sequence sufficient to confer specificity to an antigen and a constant region domain CL.

A better understanding of the present invention may be obtained through the following examples. These examples are merely set forth to illustrate the present invention, and are not to be construed as limiting the scope of the present invention.

Example 1. Construction of inCT99 Antibody and inCT99†Viral Epitope Fusion Antibody Having Cytosol-Penetrating Ability In order to confirm whether it is possible to activate virus-specific cytotoxic T cells by presenting a virus-derived T-cell epitope to cancer cells using an inCT99†viral epitope fusion antibody in which a peptide corresponding to a T-cell antigen epitope and a protein fragment containing the same are fused to a cytosol-penetrating antibody inCT99, inCT99†CMV, inCT99†HPV, and inCT99†EBV fusion antibodies were constructed.

FIG. 1 schematically shows the inCT99 antibody and the inCT99†viral epitope fusion antibody.

Specifically, "inCT99" used in the present invention included a light chain in which an in4 cyclic peptide having specificity to integrins $\alpha v\beta 3$ and $\alpha v\beta 5$ is genetically fused via a MGSSSN linker to the N-terminus of an hT4-5941 VL light-chain variable region capable of penetrating the cytosol in order to impart tumor-specific cytosol-penetrating ability. In addition, a heavy chain named RT22-01 (AAG) was used, which includes an RT22-01 VH heavy-chain variable region capable of penetrating the cytosol and in which lysine at positions 234 and 235 in the heavy-chain CH2-CH3 region is substituted with alanine and proline at position 329 is substituted with glycine, in order to exclude cancer cell inhibitory activity due to antibody-dependent cell cytotoxicity (ADCC) by binding to integrin on the surface of cancer cells.

In the present invention, "inCT99†CMV" is a protein in which a cytomegalovirus (CMV) pp65-derived $CMV_P$495-503 peptide or a peptide resulting from extending either or both of an N-terminus and a C-terminus of $CMV_P$495-503 is fused to an inCT99 antibody. Also, "inCT99†HPV" is a protein in which an $HPV_E$11-19 peptide derived from human papillomavirus subtype 16 (HPV16) or a peptide resulting from extending the N-terminus of $HPV_E$11-19 is fused to an inCT99 antibody. Also, "inCT99†EBV" is a protein in which an $EBV_{L2}$356-364 peptide derived from Epstein-Barr virus (EBV) LMP2, an $EBV_{L2}$426-434 (C426S) peptide derived therefrom, or a peptide resulting from extending the N-terminus of $EBV_{L2}$426-434 (C426S) is fused to an inCT99 antibody. Although the sequence of the T-cell antigen epitope $EBV_{L2}$426-434 derived from Epstein-Barr virus (EBV) is CLGGLLTMV, SLGGLLTMV, which is the sequence of $EBV_{L2}$426-434 (C426S) in which the residue at position 426 was substituted with Ser, was used in order to prevent oligomerization due to a Cys residue when fused to the inCT99 antibody.

Here, the virus-specific $CD8^+$ epitope peptide or a long peptide comprising the epitope was fused to the C-terminus of the inCT99 heavy chain using a $G_4S$ linker (†) or a GFLG linker (‡).

Example 2. Construction of Fusion Antibody in which Virus-Derived T-Cell Epitope Peptide and Protein Fragment Containing the Same Are Fused to inCT99(AAA), Cetuximab, and Necitumumab not Having Cytosol-Penetrating Ability In order to validate the antigen presentation mechanism of the inCT99†CMV fusion antibody and the cell death induction mechanism of the CMV pp65-specific CTLs, inCT (AAA)†CMV, Cetuximab†CMV, and Necitumumab†CMV fusion antibodies were constructed as negative control antibodies.

FIG. 2 schematically shows inCT99(AAA)†CMV, Cetuximab†CMV, and Necitumumab†CMV fusion antibodies as negative control antibodies.

FIG. 2a schematically shows inCT99(AAA)†CMV in which an endosomal escape motif $^{92}WYW^{94}$ present in VL-CDR3 of the inCT99†CMV fusion antibody is mutated to $^{92}AAA^{94}$ and an endosomal escape motif $^{95}WYW^{98}$ present in VH-CDR3 is mutated to $^{95}AAA^{98}$.

Specifically, in the inCT(AAA)†CMV antibody of the present invention, the endosomal escape motif $^{92}WYW^{94}$ present in VL-CDR3 of the inCT99 antibody is mutated to $^{92}AAA^{94}$ and the endosomal escape motif $^{95}WYW^{98}$ present in VH-CDR3 is mutated to $^{95}AAA^{98}$. Therefore, the inCT (AAA)†CMV antibody, which is endocytosed by binding to integrin $\alpha v\beta 3$ and $\alpha v\beta 5$ receptors, does not penetrate the cytosol because it does not escape from the endosome, and thus cannot present a virus-specific T-cell antigen epitope on the cell surface.

FIG. 2b schematically shows Cetuximab†CMV in which a virus-specific T-cell antigen epitope or a peptide comprising the fused to the C-terminus of the heavy-chain region of the Cetuximab antibody via a $G_4S$ linker.

Specifically, the Cetuximab†CMV fusion antibody of the present invention is an antibody in which CMV is fused to Cetuximab that targets EGFR. Since it is endocytosed by binding to EGFR and then degraded by lysosomes, it does not have ability to present the virus-specific T-cell antigen epitope on the cell surface due to penetration into the cytosol.

FIG. 2c schematically shows Necitumumab†CMV in which a virus-specific T-cell antigen epitope or a peptide comprising the same is fused to the C-terminus of the heavy-chain region of the Necitumumab antibody through a $G_4S$ linker.

Specifically, the Necitumumab†CMV fusion antibody of the present invention is an antibody in which CMV is fused to Necitumumab that targets EGFR. Since it is endocytosed by binding to EGFR and then degraded by lysosomes, it does not have ability to present the virus-specific T-cell antigen epitope on the cell surface due to penetration into the cytosol.

Example 3. Expression and Purification of inCT99 and inCT99†Viral Epitope Fusion Antibody Having Cytosol-Penetrating Ability and Control Antibodies not Having Cytosol-Penetrating Ability, Such as inCT99(AAA)†CMV, Cetuximab†CMV, and Necitumumab†CMV Fusion Antibodies In order to confirm whether it is possible to activate virus-specific cytotoxic T cells by presenting a virus-derived T-cell epitope to cancer cells using an inCT99†viral epitope fusion antibody, an inCT99 antibody and inCT99†CMV and inCT99†HPV fusion antibodies in which a virus-derived epitope peptide or a peptide resulting from extending either or both of the N-terminus and the C-terminus of the virus-derived epitope peptide was fused to the C-terminus of the heavy-chain region of the inCT99 antibody were constructed, expressed, and purified.

FIG. 3 schematically shows vectors for expressing an inCT99 antibody and inCT99†CMV, inCT99†HPV, inCT99†EBV, and inCT99†OVA fusion antibodies in animal cells (HEK293F).

FIG. 3a schematically shows the heavy-chain expression vector of an inCT99†viral peptide fusion antibody in which an antigen of virus-derived epitope peptide is fused to the heavy-chain constant region of inCT99, which is a cytosol-penetrating antibody.

FIG. 3b schematically shows the light-chain expression vector of the inCT99 antibody and the inCT99†viral peptide fusion antibody.

Specifically, when describing the heavy-chain expression vector of the inCT99†CMV$_P$495-503 fusion antibody as an example, a synthetic oligonucleotide (Macrogen, Korea) was designed such that a DNA sequence encoding the amino acid sequence 495-503 of CMVp protein was genetically fused using a $G_4S$ linker to the C-terminus based on an RT22-01 heavy chain in which DNA encoding a secretory signal peptide is fused to the 5' end, and a DNA fragment was constructed through a PCR technique and cloned into an animal cell expression vector pcDNA3.4 using NotI and HindIII restriction enzymes. In addition, a synthetic oligonucleotide for fusing the amino acid sequence 480-503 corresponding to the protein fragment including the CMVp peptide based on the constructed CMV fusion heavy chain was designed and cloning was performed as described above.

FIG. 4 schematically shows vectors for expressing Cetuximab†CMV and Necitumumab†CMV fusion antibodies as control antibodies in animal cells (HEK293F).

FIG. 4a schematically shows the heavy-chain expression vector of the Cetuximab†CMV fusion antibody.

FIG. 4*b* schematically shows the light-chain expression vector of the Cetuximab†CMV fusion antibody.

Specifically, when describing the heavy-chain expression vector of the Cetuximab†CMV$_P$480-503 fusion antibody as an example, in order to construct a heavy-chain expression vector for producing a Cetuximab†CMV$_P$480-503 fusion antibody in which a CMVp protein-derived T-cell antigen epitope peptide and a protein fragment containing the same are fused to the C-terminus of the heavy-chain constant region of a Cetuximab antibody, a synthetic oligonucleotide (Macrogen, Korea) was designed such that a DNA sequence encoding the amino acid sequence 480-503 of the CMVp protein was genetically fused using a G$_4$S linker to the C-terminus based on a Cetuximab heavy chain in which DNA encoding a secretory signal peptide is fused to the 5' end, and a DNA fragment was constructed through a PCR technique and cloned into an animal cell expression vector pcDNA3.4 using NotI and HindIII restriction enzymes. In addition, a synthetic oligonucleotide for fusing the amino acid sequence 480-503 corresponding to the protein fragment including the CMVp peptide based on the constructed CMV fusion heavy chain was designed and cloning was performed as described above. For construction of Cetuximab†MMP14-CMV$_P$495-503, which a is representative antibody of conventional APEC technology, a CMV fusion heavy chain in which the G$_4$S linker was replaced with a G$_4$SMMP14 linker (G$_4$SPRSAKLER) (SEQ ID NO: 53) at the C-terminus of the Cetuximab heavy chain was also constructed as described above by designing a synthetic oligonucleotide.

FIG. 4*c* schematically shows the heavy-chain expression vector of the Necitumumab†CMV fusion antibody.

FIG. 4*d* schematically shows the light-chain expression vector of the Necitumumab†CMV fusion antibody.

Specifically, when describing the heavy-chain expression vector of the Necitumumab†CMV$_P$480-503 fusion antibody as an example, in order to construct a heavy-chain expression vector for producing a Necitumumab†CMV$_P$480-503 fusion antibody in which a CMV pp65 protein-derived T-cell antigen epitope peptide and a protein fragment containing the same are fused to the C-terminus of the heavy-chain constant region of a Necitumumab antibody, a synthetic oligonucleotide (Macrogen, Korea) was designed such that a DNA sequence encoding the amino acid sequence 480-503 of the CMVp protein was genetically fused using a G$_4$S linker to the C-terminus based on a Necitumumab heavy chain in which DNA encoding a secretory signal peptide is fused to the 5' end, and a DNA fragment was constructed through a PCR technique and cloned into an animal cell expression vector pcDNA3.4 using NotI and HindIII restriction enzymes. In addition, a synthetic oligonucleotide for fusing the amino acid sequence 480-503 corresponding to the protein fragment including the CMVp peptide based on the constructed CMV fusion heavy chain was designed and cloning was performed as described above.

The inCT99-viral peptide antibody and the inCT99 (AAA)/Cetuximab/Necitumumab-viral peptide antibodies were expressed and purified using transient transfection, and the yields thereof were compared.

Specifically, HEK293F cells suspended in a serum-free FreeStyle 293 expression medium in a shake flask were transfected with a mixture of plasmid and polyethyleneimine (PEI). Upon transfection of 200 ml thereof into a shake flask, HEK293F cells were seeded at a density of $2.0 \times 10^6$ cells/ml in 100 ml of a medium, followed by culture at 120 rpm, 8% $CO_2$, and 37° C. The heavy-chain and light-chain plasmids suitable for antibody production were diluted to a total of 250 μg (2.5 μg/ml) including 125 μg of a heavy chain and 125 μg of a light chain in 10 ml of a FREESTYLE™ 293 expression medium, filtered, mixed with 10 ml of a medium diluted with 750 μg (7.5 μg/ml) of PEI, and then allowed to react at room temperature for 10 minutes. Thereafter, the reacted mixed medium was placed in the cells seeded in 100 ml and cultured at 120 rpm and 8% $CO_2$ for 4 hours, and the remaining 100 ml of the FREESTYLE™ 293 expression medium was added thereto, followed by culture for 6 days. Protein was purified from the collected cell culture supernatant with reference to the standard protocol. The antibody was applied to a Protein A Sepharose column and washed with PBS (pH 7.4). After the antibody was eluted at a pH of 3.0 using 0.1 M glycine and a 0.5 M NaCl buffer, the sample was immediately neutralized using a 1 M Tris (pH 9.0) buffer. The eluted antibody fraction was exchanged with 25 mM histidine and a 125 mM NaCl (pH 6.5) buffer through a PD-10 desalting column (GE Healthcare) and concentrated using a 30K centrifugal filter tube (Corning). The purified protein was measured for absorbance at a wavelength of 562 nm using the solution in a BCA protein assay kit (Thermo), and was then quantified with reference to a standard curve.

The yields of the inCT99†CMV, inCT99†HPV, and inCT99†EBV fusion antibodies and the control antibodies obtained as shown in the following tables varied depending on the type and length of protein fragment.

| Origin of viral antigen | | Name of T cell epitope-fused cytotransmab | Expression yield (mg/L) | Cleavage (Y/N) |
|---|---|---|---|---|
| CMV pp65 | 9 mer epitope | inCT99†CMV$_P$495-503 | ~90 | N |
| | | inCT99‡CMV$_P$495-503 | ~107 | N |
| | | Cetuximab†CMV$_P$495-503 | ~54 | N |
| | | inCT99(AAA)†CMV$_P$495-503 | ~100 | N |
| | | Cetuximab†MMP14-CMV$_P$495-503 | -90 | N |
| | C-term extended | inCT99†CMV$_P$495-508 | ~9 | N |
| | N-term extended | inCT99†CMV$_P$480-503 | ~40 | N |
| | | inCT99‡CMV$_P$480-503 | ~17 | N |
| | | Cetuximab†CMV$_P$480-503 | ~18 | N |
| | | inCT99(AAA)†CMV$_P$480-503 | ~55 | N |
| | N-term and C-term extended | inCT99†CMV$_P$480-504 | ~50 | N |
| | | inCT99†CMV$_P$480-505 | — | Y |
| | | inCT99†CMV$_P$480-506 | ~90 | N |
| | | inCT99†CMV$_P$480-507 | ~120 | N |
| | | inCT99†CMV$_P$480-508 | — | Y |
| | | inCT99†CMV$_P$480-509 | ~50 | N |
| | | inCT99†CMV$_P$480-510 | ~25 | N |
| | | Cetuximab†CMV$_P$-480-510 | ~10 | N |
| | | inCT99(AAA)†CMV$_P$480-510 | ~30 | N |
| | | inCT99†CMV$_P$480-511 | ~50 | N |
| | | inCT99†CMV$_P$480-512 | ~60 | N |
| | | inCT99†CMV$_P$480-513 | — | Y |
| | | inCT99†CMV$_P$480-516 | ~10 | N |
| | | Necitumumab†CMV$_P$480-516 | ~10 | N |
| | | inCT99(AAA)†CMV$_P$480-516 | ~15 | N |
| | | inCT99†CMV$_P$480-519 | ~30 | N |
| | | inCT99†CMV$_P$490-508 | ~90 | N |

†G$_4$S linker (non-cleavable linker)
‡GFLG linker (cleavable linker)
MMP14: Metrix metalloprotease 14 sensitive linker

| Origin of viral antigen | | Name of T cell epitope-fused cytotransmab | Expression yield (mg/L) | Cleavage (Y/N) |
|---|---|---|---|---|
| HPVE7 | 9 mer epitope | inCT99†HPV$_E$11-19 | ~100 | N |
| | | inCT99‡HPV$_E$11-19 | ~34 | N |

-continued

| Origin of viral antigen | | Name of T cell epitope-fused cytotransmab | Expression yield (mg/L) | Cleavage (Y/N) |
|---|---|---|---|---|
| | N-term | inCT99†HPV$_E$g1-19 | ~100 | N |
| | extended | inCT99‡HPV$_E$g1-19 | ~28 | N |
| EBV LMP2 | 9 mer | inCT99†EBV$_{L2}$356-364 | ~3 | N |
| | epitope | inCT99†EBV$_{L2}$426-434* | ~70 | N |
| | | inCT99‡EBV$_{L2}$426-434* | ~67 | N |
| | N-term | inCT99†EBV$_{L2}$417-434* | — | Y |
| | extended | inCT99†EBV$_{L2}$413-434* | ~50 | N |
| | | inCT99†EBV$_{L2}$409-434* | ~24 | N |

†G$_4$S linker (non-cleavable linker)
‡GFLG linker (cleavable linker)

FIG. 5 shows the results of analysis of size and combination form through Coomassie Blue staining after the inCT99†viral peptide fusion antibody was expressed and purified in animal cells (HEK293F) and then 3 μg of protein was separated through SDS-PAGE under or non-reducing conditions.

FIG. 5a shows results for the inCT99†CMV fusion antibody.

FIG. 5b shows results for the inCT99†HPV fusion antibody.

FIGS. 5c and 5d show results for the inCT99†EBV fusion antibody.

Specifically, 3 μg of each of the inCT99†CMV fusion antibody, the inCT99†HPV fusion antibody, and the inCT99†EBV fusion antibody purified above was separated through SDS-PAGE under 12% non-reducing conditions, and the size and combination form thereof were analyzed through COOMASSIE® Blue staining.

Consequently, inCT99 was confirmed to have a molecular weight of about 150 k Da under non-reducing conditions, and showed a heavy chain having a molecular weight of 50 kDa and a light chain having a molecular weight of 25 kDa under reducing conditions. Via SDS-PAGE analysis, it was confirmed that most of the expressed and purified individual clones were present as singletons in a solution state, and under non-reducing conditions, the inCT99 and inCT99†CMV fusion antibody clones formed a small amount of oligomer by the integrin-targeted cyclic peptide. Also, the fusion antibody was observed to have a molecular weight of 50 kDa or more due to the protein fused to the heavy chain under reducing conditions. However, in the inCT99†CMV$_P$480-506, inCT99†CMV$_P$480-507, inCT99†CMV$_P$480-508, inCT99†CMV$_P$480-509, inCT99†CMV$_P$480-511, inCT99†CMV$_P$480-512, and inCT99†CMV$_P$480-513 antibodies, some cleavage of the peptide fused to the heavy chain was observed.

In the inCT99†HPV and inCT99†EBV fusion antibodies, it was confirmed that most of the expressed and purified individual clones were present as singletons in a solution state.

Example 4. Verification of T-Cell Receptor-Like Antibody to Detect Peptide/MHC-I Complex For the inCT99†viral peptide antibodies used in the present invention, an in4 cyclic peptide targets αvβ3 and αvβ5 and a viral epitope that binds to HLA-A2 is fused thereto, and thus, in order for the antibodies to present the viral epitope on the surface of cancer cells, cancer cells must express HLA-A2 among several MHC-I molecules, and αvβ3 and αvβ5 targeted by the in4 cyclic peptide must be expressed.

FIG. 6 shows the results of flow cytometry analysis of expression of HLA-A2 among major histocompatibility complex (MHC) I genotypes and expression of integrin αvβ5/αvβ3 among cancer cell surface antigens in four human cancer cell lines.

Specifically, $2 \times 10^5$ Malme-3M, MDA-MB-231, HCT116, and Lovo cells were prepared for each sample. The cells were added with an anti-HLA-A2 antibody (Santa Cruz), an anti-integrin αvβ5 antibody, or an anti-integrin αvβ3 antibody diluted 1:100 in a FACS buffer (PBS buffer, 2% FBS), and allowed to react at 4° C. for 1 hour. After each sample was washed with 1 ml of a FACS buffer, an antibody that specifically recognizes Alexa488 (green fluorescence)-conjugated human Fc was diluted 1:600, followed by reaction at 4° C. for 30 minutes. After washing with a FACS buffer, the protein expression level on each cell surface was measured through flow cytometry.

Consequently, all the cells expressed integrin αvβ5, and integrin αvβ3 was hardly expressed in three cell lines other than Malme-3M.

The expression of HLA-A2 was the highest in Malme-3M, followed by MDA-MB-231 and then HCT116. Malme-3M showed the highest HLA-A2 expression level, but the growth rate was too slow, so MDA-MB-231 cells having a relatively high HLA-A2 expression level were mainly used for the experiment. In Lovo, which is not an HLA-A2 genotype, expression of HLA-A2 was not observed, so it was used as a negative control.

A T-cell receptor-like antibody is a monoclonal antibody having specificity similar to that of a T-cell receptor capable of recognizing and binding to a complex of cytotoxic T-cell antigen epitope peptide and MHC-I. Most therapeutic antibodies take a strategy to target proteins expressed on the cell surface or to target intracellular proteins through intracellular expression of the antibody, making it difficult to target intracellular proteins.

Intracellular proteins are degraded into peptides composed of 8-11 amino acids by the proteasome and are then delivered into the endoplasmic reticulum (ER) to form a complex with MHC-I and B2-microglobulin, which is then presented on the cell surface through the Golgi, and thus various T-cell antibodies receptor-like capable of specifically recognizing the peptide-MHC-I complex have been reported. Therefore, for an experiment to determine whether a virus- and cancer-antigen-derived protein containing a T-cell antigen epitope peptide is delivered into the cell and then presented in the form of a peptide-MHC-I complex on the cell surface using the inCT99†viral peptide fusion antibody, various T-cell receptor-like antibodies capable of specifically recognizing the peptide-MHC-I complex were constructed.

H9 is a TCR-like antibody that detects a complex of CMV$_P$495-503, which is a CD8$^+$ T-cell epitope peptide derived from a CMV antigen, and HLA-A2. However, the affinity of the H9 antibody was reported to be 300 nM, and in a preliminary experiment, the H9 antibody did not recognize the peptide-MHC-I complex presented on the cell surface after treatment of cancer cells with the inCT99†CMV fusion antibody. Therefore, by introducing a library to the CDR sequences of VH and VL of the H9 antibody using a protein antigen in which the CMV$_P$495-503 peptide-β2-microglobulin-HLA-A*02:01 was made in the form of a single-chain trimer (SCT) via a peptide linker (Schmittnaegel, Hoffmann et al. 2016), the affinity thereof was improved. In the primary experiment for affinity improvement using the H9 antibody, H9#1 and H9#38 were selected, and in the secondary experiment for affinity improvement using H9#1, C1-17 was selected. The finally selected C1-17 was constructed, purified, and used to analyze the ability to present the CMV peptide-MHC-I complex on the cell surface after treatment with the inCT99†CMV fusion antibody.

7-1 was constructed, purified, and used as a TCR-like antibody for analyzing the complex of HPV epitope and HLA-A2, and L2 was constructed, purified, and used as a TCR-like antibody for analyzing the complex of EBV epitope and HLA-A2.

FIG. 7 schematically shows the expression vectors of T-cell receptor (TCR)-like antibodies and the results of analysis of size and combination form after purification.

FIG. 7a schematically shows the expression vectors of T-cell receptor (TCR)-like antibodies.

FIG. 7b shows the results of analysis of size and combination form through COOMASSIE® Blue staining after H9, H9#1, and H9#38 antibodies were expressed and purified in animal cells (HEK293F) and then 3 μg of protein was separated through SDS-PAGE under reducing or non-reducing conditions.

FIG. 7c shows the results of analysis of the C1-17 antibody in the same manner as in FIG. 7b.

FIG. 7d shows the results of analysis of 7-1 and L2 antibodies in the same manner as in FIG. 7b.

Specifically, the sequences of the human heavy-chain variable region (VH) and the human light-chain variable region (VL) of the monoclonal antibodies H9, H9#1, and H9#38 and C1-17 clones, which specifically recognize the $CMV_p480$-503/HLA-A*02:01 complex, which is a complex of the CMV pp65-derived peptide 495-503 and the HLA-A*02:01 molecule, were prepared through gene synthesis (Bioneer, Korea).

The sequences of the human heavy-chain variable region (VH) and the human light-chain variable region (VL) of the 7-1 clone (WO2016/182957, Constructs targeting HPV16-E7 peptide/MHC complexes and uses thereof), which is a monoclonal antibody that specifically recognizes the $HPV_E11$-19/HLA-A*02:01 complex, which is a complex of the HPV16 E7 protein-derived peptide 11-19 and the HLA-A*02:01 genotype, were prepared through gene synthesis (Bioneer, Korea).

The L2 clone (WO2015/199618, Epstein-Barr virus LMP2 specific antibody and uses thereof), which is a monoclonal antibody that specifically recognizes the complex of the EBV LMP2 protein-derived peptide 426-434 (CLGGLLTMV) (SEQ ID NO: 52) or the SLGGLLTMV (SEQ ID NO: 54) peptide and the HLA-A*02:01 genotype, is a mouse monoclonal antibody obtained by producing a hybridoma after immunizing a mouse with an antigen. The sequences of the human heavy-chain variable region (VH) and the human light-chain variable region (VL) of the L2 antibody were prepared through gene synthesis (Bioneer, Korea).

The VH gene was introduced to the heavy chain in which the heavy-chain constant region is mouse immunoglobulin G 2a to produce a DNA fragment through a PCR technique, which was then cloned into an animal cell expression vector pcDNA3.4 using NotI and HindIII restriction enzymes. The VL gene was cloned into the light chain in which the light-chain constant region is a mouse kappa constant region in the same manner as above, thereby constructing a chimeric antibody. This serves to prevent binding of the inCT99 antibody to the human Fc region and to analyze only the binding of the T-cell receptor-like antibody using a fluorescence-conjugated secondary antibody that recognizes the mouse Fc region when analyzing the peptide-MHC-I complex through flow cytometry after treatment with the inCT99 and the inCT99 fusion antibody.

All of the T-cell receptor (TCR)-like antibodies were expressed and purified in animal cells (HEK293F).

Specifically, HEK293F cells suspended in a serum-free FREESTYLE™ 293 expression medium in a shake flask were transfected with a mixture of plasmid and polyethyleneimine (PEI). Upon transfection of 100 ml thereof into a shake flask, HEK293F cells were seeded at a density of $2.0 \times 10^6$ cells/ml in 50 ml of a medium, followed by culture at 120 rpm, 8% $CO_2$, and 37° C. The heavy-chain and light-chain plasmids suitable for antibody production were diluted to a total of 125 μg (2.5 μg/ml) including 62.5 μg of a heavy chain and 62.5 μg of a light chain in 10 ml of a FREESTYLE™ 293 expression medium, filtered, and mixed with 10 ml of a medium diluted with 375 μg (7.5 μg/ml) of PEI, followed by reaction at room temperature for 10 minutes. Thereafter, the reacted mixed medium was added to the cells seeded in 50 ml and cultured at 120 rpm and 8% $CO_2$ for 4 hours, after which the remaining 50 ml of the FREESTYLE™ 293 expression medium was added thereto, followed by culture for 6 days. Protein was purified from the collected cell culture supernatant with reference to the standard protocol. The antibody was applied to a Protein A Sepharose column and washed with PBS (pH 7.4). After the antibody was eluted at a pH of 3.0 using 0.1 M glycine and a 0.5 M NaCl buffer, the sample was immediately neutralized using a 1 M Tris (pH 9.0) buffer. The eluted antibody fraction was exchanged with 25 mM histidine and a 125 mM NaCl (pH 6.5) buffer through a PD-10 desalting column (GE Healthcare) and concentrated using a 30K centrifugal filter tube (Corning). The purified protein was measured for absorbance at a wavelength of 562 nm using the solution in a BCA protein assay kit (Thermo) and then quantified with reference to a standard curve.

3 μg of the purified T-cell receptor (TCR)-like antibodies were separated through SDS-PAGE under 12% non-reducing conditions, and the size and combination form thereof were analyzed through COOMASSIE® Blue staining.

Consequently, it was confirmed that all of the H9, H9#1, H9#38, C1-17, 7-1, and L2 antibodies formed a small amount of oligomer under non-reducing conditions, but mostly existed as singletons.

FIG. 8 shows the results of flow cytometry analysis to determine the ability of T-cell receptor (TCR)-like antibodies to bind to the peptide/HLA-A*02:01 complex using cancer cell lines having different expression levels of HLA-A*02:01.

FIG. 8a shows the results of measurement of the ability of the H9, H9#1 and H9#38 antibodies to bind to the $CMV_p495$-503/HLA-A*02:01 complex in cancer cells pulsed with $CMV_p495$-503 peptide.

Specifically, Malme-3M (HLA-A*02:01++), MDA-MB-231 (HLA-A+02:01++), HCT116 (HLA-A*02:01+), and Lovo (HLA-A*02:01−) cells, having different expression levels of HLA-A*02:01, were prepared at a density of $3.0 \times 10^5$ cells/ml in an RPMI medium containing 10% FBS and 1% ABAM antibiotic, added with 50 μM of various synthetic peptides (Anygen, Korea) capable of forming a complex with HLA-A*02:01, including $CMV_p495$-503 peptide and $HPV_E11$-19 peptide, and allowed to react at 5% $CO_2$ and 37° C. for 3 hours. A negative control group not treated with peptide was added with DMSO. After 3 hours, centrifugation was performed at 1300 rpm for 3 minutes to remove the supernatant containing the peptide not bound to the cells, and the cells were washed with a FACS buffer and centrifuged at 1300 rpm for 3 minutes to remove the supernatant. For each sample, $1.5 \times 10^5$ cells were prepared, and each of the monoclonal antibodies H9, H9#1 and H9#38 that specifically recognize the CMV$_P$495-503/HLA-A*02:01 complex obtained through expression and purification was diluted to a concentration of 10 nM in 100 μl of a FACS buffer and then added thereto, followed by reaction at 4° C. for 1 hour. After each sample was washed with 1 ml of a FACS buffer, a F(ab')$_2$ antibody that specifically recognizes Alexa 647 (red fluorescence)-conjugated mouse Fc was diluted 1:1200 in 100 μl of a FACS buffer, followed by reaction at 4° C. for 30 minutes. The cells were washed with 1 ml of a FACS buffer and then analyzed through flow cytometry.

Consequently, the H9#1 antibody obtained through primary affinity improvement of H9 recognized the CMV$_P$495-503/HLA-A*02:01 complex better than 500 nM of the H9 antibody, even when used at a concentration of 5 nM. Therefore, whether the H9#1 and H9#38 antibodies are able to more efficiently recognize the CMV$_P$495-503/HLA-A*02:01 complex in cancer cells treated with the inCT99†CMV fusion antibody than the H9 antibody was evaluated.

FIG. 8b shows the results of analysis of the ability of the inCT99†CMV fusion antibody to present the T-cell antigen epitope to HLA-A*02:01 through intracellular antigen processing, performed using H9#1 and H9#38 antibodies.

Specifically, in a 24-well plate, an MDA-MB-231 cell line was diluted at a density of $2.0 \times 10^5$ cells/ml per well in an RPMI medium containing 10% FBS and 1% ABAM antibiotic, followed by culture at 37° C. and 5% $CO_2$ for 12 hours, after which the medium was removed and the inCT99, inCT99†CMV$_P$480-503, and inCT99†HPV$_E$1-19 fusion antibodies were diluted to a concentration of 4 μM in 500 μl of a medium, followed by culture at 37° C. and 5% $CO_2$ for 18 hours. Thereafter, the medium was removed, and the cells were washed with DPBS and treated with 100 μl of a trypsin-EDTA solution per well at 37° C. for 3 minutes to thus separate the cells from the plate. 1 ml of an RPMI medium containing 10% FBS was added to each well to neutralize trypsin-EDTA, and the cells were recovered and centrifuged at 1300 rpm for 3 minutes to remove the supernatant. The cells were washed with 1 ml of a FACS buffer and centrifuged to remove the supernatant. The cell pellets in each well were lysed with 300 μl of a FACS buffer and divided into six samples, one sample of which was used as a control containing only a secondary antibody. Each sample was added with H9#1 and H9#38 at 50 nM in 100 μl of a FACS buffer, followed by reaction at 4° C. for 1 hour. After each sample was washed with 1 ml of a FACS buffer, a F(ab')$_2$ antibody that specifically recognizes Alexa647 (red fluorescence)-conjugated mouse Fc was diluted 1:600 in 100 μl of a FACS buffer, followed by reaction at 4° C. for 30 minutes. The cells were washed with 1 ml of a FACS buffer and then analyzed through flow cytometry.

The H9 antibody did not detect the CMV$_P$495-503/HLA-A*02:01 complex presented by the inCT99†CMV fusion antibody through intracellular antigen processing, but the H9#1 and H9#38 clones having improved affinity detected the CMV$_P$495-503/HLA-A*02:01 complex. However, the ability of the H9#1 antibody to detect the CMV$_P$495-503/HLA-A*02:01 complex was determined to be low when comparing and measuring the ability of various types of inCT99†CMV fusion antibodies to present the CMV$_P$495-503/HLA-A*02:01 complex, and thus a secondary affinity improvement experiment was performed, whereby a C1-17 antibody was obtained.

FIG. 8c shows the results of measurement of the ability of the C1-17 antibody to bind to the CMV$_P$495-503/HLA-A*02:01 complex in cancer cells pulsed with CMV$_P$495-503 peptide.

Details with regard to the method of measurement thereof are as described in FIG. 8a, but in order to measure the ability of the inCT99†CMV fusion antibody to present the CMV$_P$495-503/HLA-A*02:01 complex, since a small amount of CMV$_P$495-503 peptide should be detectable even when pulsed on the surface of cancer cells, the concentration of CMV$_P$495-503 used for pulsing was lowered from 50 mM to 4 mM.

Thereby, the C1-17 antibody detected the CMV$_P$495-503/HLA-A*02:01 complex more efficiently than the H9 antibody or the H9#1 antibody even when cancer cells were pulsed with the CMV$_P$495-503 peptide at a concentration of 4 mM, indicating that this detection capability was specific to HLA-A2:01 expressed on the surface of cancer cells, and thus there was no detection capability in Lovo cells in which HLA-A2:01 was not expressed.

FIG. 8d shows the results of measurement of the ability of the 7-1 antibody to bind to the HPV$_E$11-19/HLA-A*02:01 complex in cancer cells pulsed with HPV$_E$11-19 peptide.

FIG. 8e shows the results of measurement of the ability of the L2 antibody to bind to the EBV$_{L2}$426-434 (C426S)/HLA-A*02:01 complex in cancer cells pulsed with EBV$_{L2}$426-434 (C426S) peptide.

Details with regard to the method of measurement thereof are as described in FIG. 8a, but the specificity of the 7-1 and L2 antibodies to the peptide/HLA-A*02:01 has already been reported in the literature, and thus only MDA-MB-231 cells in which the expression of HLA-A*02:01 is relatively high were used, and pulsing with HPV$_E$11-19 peptide was performed in order to evaluate the detection capability of the 7-1 antibody, and the EBV$_{L2}$426-434 (C426S) peptide was used in order to evaluate the detection capability of the L2 antibody.

Thereby, it was confirmed that the 7-1 antibody and the L2 antibody specifically detected the HPV$_P$11-19/HLA-A*02:01 complex and the EBV$_{L2}$426-434 (C426S)/HLA-A*02:01 complex, respectively.

Example 5. Evaluation of Ability of inCT99†CMV Fusion Antibody and Control Antibodies to Present CMV$_P$495-503 Epitope in Cancer Cell Line Having HLA-A*02:01 Genotype In order to evaluate whether the constructed inCT99†CMV fusion antibodies directly bind to HLA-A*02:01 expressed on the surface of cancer cells or present the CMV$_P$495-503/HLA-A*02:01 complex on the surface of cancer cells through intracellular antigen processing, cancer cells were added with the constructed antibodies and then allowed to react at 4° C. and 37° C., after which the CMV$_P$495-503/HLA-A*02:01 complex was detected using the C1-17 antibody.

FIG. 9 shows the results of flow cytometry analysis to determine the ability of various inCT99†CMV fusion antibodies to bind to cell-surface HLA-A*02:01 and to present the T-cell antigen epitope to HLA-A*02:01 through intracellular antigen processing.

FIG. 9a shows a scheme for analyzing the ability of the inCT99†CMV fusion antibody to bind to cell-surface HLA-A*02:01 at 4° C.

FIG. 9b shows a scheme for analyzing the ability of the inCT99†CMV fusion antibody to present the T-cell antigen epitope to HLA-A*02:01 through intracellular antigen processing at 37° C.

FIG. 9c shows the results of flow cytometry analysis after treatment with various inCT99†CMV fusion antibodies in the same manner as in FIGS. 7a and 7b.

Specifically, as shown in FIG. 9a for evaluating whether the inCT99†CMV fusion antibodies directly bind to HLA-A*02:01 expressed on the surface of cancer cells, MDA-MB-231 cells were prepared at a density of $3.0 \times 10^5$ cells/ml in an RPMI medium containing 10% FBS and 1% ABAM antibiotic, added with inCT99†CMV fusion antibodies at a concentration of 4 µM, and allowed to react at 5% $CO_2$ and 37° C. for 3 hours. Here, a positive control group was treated with 4 µM $CMV_p495$-503 peptide, and a negative control group was added with a histidine buffer in which the antibody was dissolved. After 3 hours, centrifugation was performed at 1300 rpm for 3 minutes to remove the supernatant containing the antibody and peptide not bound to the cells, and the cells were washed with a FACS buffer and then centrifuged at 1300 rpm for 3 minutes to remove the supernatant. For each sample, $1.5 \times 10^5$ cells were prepared, and the C1-17 clone, which is a monoclonal antibody that specifically recognizes the $CMV_p495$-503/HLA-A*02:01 complex obtained through expression and purification, was diluted to a concentration of 4 nM in 100 µl of a FACS buffer and added thereto, followed by reaction at 4° C. for 1 hour. After each sample was washed with 1 ml of a FACS S buffer, a $F(ab')_2$ antibody that specifically recognizes ALEXA647™ (red fluorescence)-conjugated mouse Fc was diluted 1:1200 in 100 µl of a FACS buffer, followed by reaction at 4° C. for 30 minutes. After washing with 1 ml of a FACS buffer, analysis was performed through flow cytometry and FLOWJO™.

Based on the results of experimentation shown in FIG. 9a, the inCT99†$CMV_p480$-503 antibody, which is a fusion antibody resulting from extending only the N-terminus of the $CMV_p495$-503 T-cell epitope peptide, was confirmed to directly bind to cell-surface HLA-A*02:01, like the positive control group treated with the $CMV_p495$-503 peptide. However, for the inCT99†$CMV_p495$-503 antibody fused with the $CMV_p495$-503 T-cell epitope peptide, the inCT99†$CMV_p495$-508 antibody fused with the peptide resulting from extending the C-terminus of the $CMV_p495$-503 T-cell epitope peptide, and the antibodies fused with the peptides resulting from extending both the N-terminus and C-terminus of the peptide (490-508, 480-504, 480-505, 480-506, 480-507, 480-508, 480-509, 480-511, 480-512, 480-513, 480-516, 480-519), it was confirmed that there was no ability to bind to cell-surface HLA-A*02:01.

Specifically, as shown in FIG. 9b for evaluating whether the inCT99†CMV fusion antibodies present the $CMV_p495$-503/HLA-A*02:01 complex on the surface of cancer cells through intracellular antigen processing, MDA-MB-231 cells were prepared at a density of $1.5 \times 10^5$ cells/ml in an RPMI medium containing 10% FBS and 1% ABAM antibiotic, attached to a 24-well plate for 12 hours, added with inCT99†CMV fusion antibodies at a concentration of 4 µM, and allowed to react at 5% $CO_2$ and 37° C. for 18 hours. Here, a positive control group was treated with 4 µM $CMV_p495$-503 peptide, and a negative control group was added with a histidine buffer in which the antibody was dissolved. After 18 hours, the antibody-treated medium was recovered and washed with 1 ml of DPBS, after which MDA-MB-231 cells attached to the bottom were recovered by scraping using a yellow tip, suspended in 1 ml of DPBS, and then centrifuged at 1300 rpm for 3 minutes. The supernatant containing the antibody and peptide not bound to the cells was removed, and the cells were washed with a FACS buffer and then centrifuged at 1300 rpm for 3 minutes to remove the supernatant. For each sample, $1.5 \times 10^5$ cells were prepared, and the C1-17 clone, which is a monoclonal antibody that specifically recognizes the $CMV_p495$-503/ HLA-A*02:01 complex obtained through expression and purification, was diluted to a concentration of 4 nM in 100 µl of a FACS buffer and added thereto, followed by reaction at 4° C. for 1 hour. After each sample was washed with 1 ml of a FACS buffer, a $F(ab')_2$ antibody that specifically recognizes ALEXA647™ (red fluorescence)-conjugated mouse Fc was diluted 1:1200 in 100 µl of a FACS buffer, followed by reaction at 4° C. for 30 minutes. After washing with 1 ml of a FACS buffer, analysis was performed through flow cytometry and FLOWJO™.

Consequently, the inCT99 antibody, which is a negative control antibody, did not present the $CMV_p495$-503/HLA-A*02:01 complex on the surface of MDA-MB-231 cells. However, for the inCT99†$CMV_p480$-503 antibody, which is a fusion antibody resulting from extending only the N-terminus of the $CMV_p495$-503 T-cell epitope peptide, and the inCT99†$CMV_p480$-510, inCT99†$CMV_p480$-511, inCT99†$CMV_p480$-516, and inCT99†$CMV_p480$-519 antibodies, among antibodies fused with the peptide resulting from extending both the N-terminus and the C-terminus of the $CMV_p495$-503 T-cell epitope peptide, it was found that the virus-specific T-cell antigen epitope generated through intracellular antigen processing after penetration of the antibody into the cytosol was presented on the cell surface, whereby the $CMV_p495$-503/HLA-A*02:01 complex was presented on the surface of MDA-MB-231 cells.

The inCT99†$CMV_p480$-503 antibody, which is a fusion antibody resulting from extending only the N-terminus of the $CMV_p495$-503 T-cell epitope peptide, was able to directly bind to HLA-A*02:01 expressed on the surface of cancer cells, and to present, on the cell surface, the virus-specific T-cell antigen epitope generated through intracellular antigen processing after penetration of the antibody into the cytosol. In order to evaluate whether the ability of the inCT99†$CMV_p480$-503 antibody to bind to HLA-A*02:01 expressed on the cancer cell surface is due to the ability of the $CMV_p480$-503 peptide to bind to HLA-A*02:01 on the cancer cell surface, the ability of the control antibodies inCT99(AAA)†$CMV_p480$-503 and Cetuximab†$CMV_p480$-503 to bind to cell-surface HLA-A*02:01 at 4° C. and the ability thereof to present the T-cell antigen epitope to HLA-A*02:01 through intracellular antigen processing at 37° C. were measured.

FIG. 9d shows the results of flow cytometry analysis of the inCT99†$CMV_p480$-503 fusion antibody and the control antibodies inCT99(AAA)†$CMV_p480$-503 and Cetuximab†$CMV_p480$-503 after treatment in the same manner as in FIGS. 9a and 9b.

Based on the results of measurement of the ability of the inCT99†$CMV_p480$-503 fusion antibody, the control antibodies inCT99(AAA)†$CMV_p480$-503 and Cetuximab†$CMV_p480$-503, and the $CMV_p480$-503 peptide to bind to HLA-A*02:01 on the cancer cell surface at 4° C. in the same manner as in FIG. 9a, the $CMV_p480$-503 peptide, resulting from extending only the N-terminus of the $CMV_p495$-503 T-cell epitope peptide, exhibited higher ability to bind to HLA-A*02:01 on the cancer cell surface than the $CMV_p495$-503 peptide, which is a 9mer T-cell epitope peptide. In addition, all of the inCT99†$CMV_p480$-503 fusion antibody fused with the $CMV_p480$-503 peptide and the control antibodies inCT99(AAA)†CMV$_P$480-503 and Cetuximab†CMV$_P$480-503 exhibited ability to bind to HLA-A*02:01 on the cancer cell surface at 4° C. Therefore, the ability of the inCT99†CMV$_P$480-503 antibody to bind to HLA-A*02:01 expressed on the cancer cell surface is deemed to be due to the ability of the CMV$_P$480-503 peptide to bind to HLA-A*02:01 on the cancer cell surface.

Based on the results of evaluation of the ability of the inCT99†CMV$_P$480-503 fusion antibody and the control antibodies inCT99(AAA)†CMV$_P$480-503 and Cetuximab†CMV$_P$480-503 to present the T-cell antigen epitope to HLA-A*02:01 through intracellular antigen processing at 37° C. in the same manner as FIG. in 9b, the control antibodies inCT99(AAA)†CMV$_P$480-503 and Cetuximab†CMV$_P$480-503 were degraded after endocytosis during treatment in MDA-MB-231 cancer cells at 37° C. for 18 hours, so the CMV$_P$495-503/HLA-A*02:01 complex was detected at a low level on the surface of cancer cells compared to reaction at 4° C. However, the inCT99†CMV$_P$480-503 fusion antibody presented the CMV$_P$495-503/HLA-A*02:01 complex on the surface of cancer cells through intracellular antigen processing after endocytosis during treatment in MDA-MB-231 cancer cells at 37° C. for 18 hours, whereby the CMV 495-503/HLA-A*02:01 complex could be detected at a level similar to the group treated with the inCT99†CMV$_P$480-503 fusion antibody at 4° C. or the positive control group treated with the CMV$_P$495-503 peptide at 37° C. Therefore, it was confirmed that the inCT99†CMV$_P$480-503 fusion antibody was able to directly bind to HLA-A*02:01 expressed on the surface of cancer cells but mostly presented, on the cell surface, the virus-specific T-cell antigen epitope generated through intracellular antigen processing after penetration of the fusion antibody into the cytosol.

In order to demonstrate that the inCT99†CMV fusion antibody did not directly bind to HLA-A*02:01 on the cancer cell surface but presented the CMV$_P$495-503/HLA-A*02:01 complex on the cancer cell surface through intracellular antigen processing after endocytosis, the ability to present the T-cell antigen epitope to HLA-A*02:01 through intracellular antigen processing at 37° C. was evaluated using the inCT99(AAA)†CMV$_P$480-510, Cetuximab†CMV$_P$480-510, inCT99(AAA)†CMV$_P$480-516, and Necitumumab†CMV$_P$480-516 antibodies, which are negative control antibodies for the inCT99†CMV$_P$480-510 and inCT99†CMV$_P$480-516 fusion antibodies, not having ability to bind to HLA-A*02:01 on the cancer cell surface at 4° C.

FIG. 9e shows the results of evaluation of the ability of the inCT99†CMV$_P$480-510 fusion antibody and the control antibodies inCT99(AAA)†CMV$_P$480-510 and Cetuximab†CMV$_P$480-510 to present the T-cell antigen epitope to HLA-A*02:01 through intracellular antigen processing at 37° C. in the same manner as in FIG. 9b.

FIG. 9f shows the results of evaluation of the ability of the inCT99†CMV$_P$480-516 fusion antibody and the control antibodies inCT99(AAA)†CMV$_P$480-516 and Necitumumab†CMV$_P$480-516 to present the T-cell antigen epitope to HLA-A*02:01 through intracellular antigen processing at 37° C. in the same manner as in FIG. 9b.

Consequently, none of the control antibodies inCT99 (AAA)†CMV$_P$480-510, Cetuximab†CMV$_P$480-510, inCT99(AAA)†CMV$_P$480-516, and Cetuximab†CMV$_P$480-516, which were degraded after endocytosis during treatment in MDA-MB-231 cancer cells at 37° C. for 18 hours, had ability to present the T-cell antigen epitope to HLA-A*02:01. In contrast, both the inCT99†CMV$_P$480-510 and inCT99†CMV$_P$480-516 fusion antibodies presented the CMV$_P$495-503/HLA-A*02:01 complex on the surface of cancer cells through intracellular antigen processing after endocytosis during treatment in MDA-MB-231 cancer cells at 37° C. for 18 hours.

Therefore, it was confirmed that the inCT99†CMV fusion antibody was able to directly bind to HLA-A*02:01 on the cancer cell surface depending on the type of T-cell antigen epitope peptide to be fused, but that the inCT99†CMV fusion antibody fused with the T-cell antigen epitope peptide not having ability to directly bind to HLA-A*02:01 on the cancer cell surface presented the CMV$_P$495-503/HLA-A*02:01 complex on the cancer cell surface through intracellular antigen processing after endocytosis.

Example 6. Analysis of Proportion and Phenotype of CMV Pp65-Specific Cytotoxic T Cells in PBMCs of Blood Donors Having HLA-A*02 Genotype In the present invention, "CMV pp65-specific cytotoxic T cells" are cytotoxic T cells expressing a T-cell receptor that specifically recognizes the CMVp protein-derived peptide 495-503-HLA-A*02:01 complex. It is known that CMV pp65-specific cytotoxic T cells exist in the form of memory T cells at different proportions among peripheral blood mononuclear cells of persons who have been infected with HLA-A*02:01 genotype CMV. Memory T cells express the phenotypic marker CD45RO, and may be classified into, depending on the expression of CD62 ligand, central memory T cells (CD45RO$^+$CD62L$^+$CD8$^+$) and effector memory T cells (CD45RO$^+$CD62L$^-$CD8$^+$). Most CMV pp65-specific cytotoxic T cells are differentiated into effector memory T cells and terminally differentiated effector memory T cells (TEMRA), and thus, upon secondary antigen exposure, effector molecules such as granzyme B, interferon-gamma (IFN-γ), and the like may be rapidly produced. In addition, CD27 and CD28, which are co-stimulatory molecules, begin to differentiate (activate) while sequentially losing the expression of CD28 and CD27 through antigen stimulation in the "early" phenotype of CD27+CD28+, and progress to intermediate and late stages. In addition, these have effector phenotypes in which the expression of lytic cytokines (perforin, granzyme B) is increased at the same time as the loss of CD28 and CD27 expression. In addition, the expression of PD-1 among exhaustion markers may be induced due to continuous antigen stimulation, which inhibits antigen-specific cell activation through binding to a PD-L1 molecule expressed on the surface of virus-infected cells and cancer cells. In addition, whether the expression of CD127, which is a homeostatic proliferation marker, enables self-renewal even without antigen stimulation can be evaluated. Therefore, the present invention was intended to actually confirm the proportion and phenotype of CMV pp65-specific cytotoxic T cells contained in PBMCs obtained from healthy blood donors.

FIG. 10 shows the results of expression of HLA-A2, which is the HLA-A subgenotype, and the proportion and phenotype of CMV pp65-specific cytotoxic T cells before or after stimulation with CMV$_P$495-503 peptide by subjecting peripheral blood mononuclear cells (PBMCs) isolated from the blood collected from healthy blood donors to staining using an anti-HLA-A2 antibody.

FIG. 10a shows the results of flow cytometry analysis of expression of HLA-A2, which is the HLA-A subgenotype, of peripheral blood mononuclear cells (PBMC).

Specifically, 30 ml of blood was collected from each healthy blood donor who signed a consent form for human research, and centrifuged at 1500 rpm for 5 minutes to isolate serum therefrom. Serum in the supernatant was separately stored at −20° C. so that blood cells did not mix. In order to isolate PBMCs, 15 ml of FICOLL® (GE Healthcare) was placed in a 50 ml test tube. Serum-free blood was mixed with PBS (pH 7.4) at 1:1 and shaken, and 30 ml thereof was carefully placed in a test tube containing FICOLL® so as to prevent mixing with FICOLL®, and centrifuged at room temperature at 750×g with no break for 20 minutes. Thereafter, the buffy coat (leukocyte layer) formed on FICOLL® was recovered and washed twice with PBS (pH 7.4), so PBMCs containing T cells, B cells, NK cells, and monocytes were obtained. Using a freezing solution containing 90% FBS and 10% DMSO, $5.0×10^6$ to $1.0×10^7$ PBMCs per vial were placed in a freezing container, frozen, and then stored through cryogenic freezing (in liquid nitrogen at −196° C.). For each sample, $2.0×10^5$ PBMCs were prepared, and a PE-conjugated anti-HLA-A2 antibody or PE-conjugated anti-mouse IgG2b was diluted 1:100 in 100 μl of a FACS buffer, followed by reaction at 4° C. for 30 minutes. Based on the results of flow cytometry analysis after washing with 1 ml of a FACS buffer, it was confirmed that 55% (33 persons) of 60 volunteers exhibited staining of the anti-HLA-A2 antibody and thus had the HLA-A*02 genotype.

FIG. 10b shows the results of flow cytometry analysis to determine the proportion of CMV pp65-specific cytotoxic T cells among lymphocytes or CD8+ T cells after PBMCs from healthy blood donors having the HLA-A2 genotype were stimulated with CMV$_P$495-503 peptide, which is a T-cell antigen epitope, and then amplified for 10-14 days.

FIG. 10c shows results of flow cytometry analysis of antigen phenotype and T-cell differentiation of the amplified CMV pp65-specific cytotoxic T cells in FIG. 10b.

Specifically, in order to stimulate PBMCs with CMV$_P$495-503 peptide, which is a T-cell antigen epitope, cryopreserved donor PBMCs were rapidly thawed in a water bath at 37° C., placed in an RPMI medium containing 10% FBS and 1% ABAM antibiotic, and centrifuged at 1500 rpm for 3 minutes to remove the supernatant, and PBMCs were washed with an X-VIVO™ 15 medium (Lonza, Switzerland) containing 2% human AB serum (Sigma, USA) and then centrifuged to remove the supernatant. PBMCs were pulsed at a CMV$_P$495-503 peptide concentration (5 μg/ml) in an X-vivo medium supplemented with 2% human serum so as to become $2×10^6$ cells/ml, followed by culture at 5% $CO_2$ and 37° C. in a 14 ml U-bottom tube (SPL). After 3 days, the U-bottom tube was centrifuged at 1500 rpm for 3 minutes to remove the supernatant, and the cells were suspended in an X-vivo medium supplemented with recombinant human interleukin-2 (200 IU/ml, Peprotech, USA) and % human serum and then seeded at a density of $2×10^6$ cells/2 ml/well in a 24-well plate. From the $6^{th}$ day of culture, the medium was replaced once every 2 days with an X-vivo medium supplemented with IL15/IL15Rα (0.5 nM), IL-2 (200 IU/ml), and 2% human serum. Here, the cells were maintained at a density of $2.0×10^6$ cells/well, resuspended, amplified, and distributed to a greater number of wells. On the $10^{th}$ to $14^{th}$ days, in order to confirm the proportion and phenotype of CMV pp65-specific cytotoxic T cells in the amplified cells, FACS staining was performed through the following method.

For each sample, the cells were prepared at $5.0-7.0×10^5$ cells/50 μl, added with 5 μl of a PE-conjugated CMV/HLA-A*02:01 pentamer (Proimmune, UK), and allowed to react at room temperature for 20 minutes. After washing with 1 ml of a FACS buffer, centrifugation was performed at 1500 rpm for 3 minutes to remove the supernatant. Each sample was added with 100 μl of a FACS buffer and the co-stimulatory molecule was stained using a FITC-conjugated antibody recognizing human CD28 (e-Bioscience), an APC-conjugated antibody recognizing human CD27 (e-Bioscience), and a PerCP-eFluor710-conjugated antibody recognizing human CD8 (e-Bioscience). Each antibody was added in an amount of 5 μl, and reaction was carried out at 4° C. for 30 minutes. After washing with 1 ml of a FACS buffer, centrifugation was performed at 1500 rpm for 3 minutes to remove the supernatant. The cells were added with 200 μl of a fixing solution (4% paraformaldehyde, PBS buffer), mixed well, and fixed at 4° C. for 30 minutes. After washing with 2 ml of a FACS buffer, centrifugation was performed at 1500 rpm for 3 minutes to remove the supernatant.

Based on the results of flow cytometry analysis, the proportion of CMV pp65-specific cytotoxic T cells (CD8†CMV/HLA-A*02:01 pentamer+) in PBMCs not stimulated with CMV$_P$495-503 peptide as a T-cell antigen epitope was 0.04-1.01%, and the proportion of CMV pp65-specific cytotoxic T cells in cytotoxic T cells was 0.14-5.34%. After stimulation of PBMCs with CMV$_P$495-503 peptide, which is a T-cell antigen epitope, the proportion of CMV pp65-specific cytotoxic T cells (CD8†CMV/HLA-A*02:01 pentamer+) in PBMCs was increased to 1.0-25.6%, and the proportion of CMV pp65-specific cytotoxic T cells in cytotoxic T cells was increased to 3.48-90.8%.

Based on the results of analysis of cell phenotype of CMV pp65-specific cytotoxic T cells, the memory cell phenotype of CMV pp65-specific cytotoxic T cells not stimulated with the CMV$_P$495-503 peptide, which is the T-cell antigen epitope, was determined to be effector memory T cells (TEM) or terminally differentiated effector memory T cells (TEMRA), but after stimulation with CMV$_P$495-503 peptide for 10-14 days, these cells were confirmed to be immediately activated and differentiated into TEMRA showing a cytotoxic effect. The expression of CCR7, which induces homing to lymph nodes, was low, and the expression of CXCR3, which induces homing to tumors or inflamed tissues, was high. In particular, it was confirmed that the expression of PD-1, which is an "exhausted" phenotype marker, was reduced after stimulation of CMV pp65-specific cytotoxic T cells with CMV$_P$495-503 peptide for 10-14 days. Therefore, CMV pp65-specific cytotoxic T cells were immediately activated when stimulated with CMV$_P$495-503 peptide, which is the T-cell antigen epitope, and then differentiated into TEMRA showing a cytotoxic effect, resulting in homing to the tumor tissue. When the CMV T-cell antigen epitope is presented using the inCT99†CMV antibody in tumor cells, it can be found that CMV pp65-specific cytotoxic T cells are capable of immediate tumor cell death through homing to tumors.

Example 7. Evaluation of Ability of inCT99†CMV Fusion Antibody to Induce Cell Death of Cancer Cell Line Using CMV Pp65-Specific Cytotoxic T Cells after Treatment Therewith In order to evaluate whether tumor cell death is caused by the amplified CMV pp65-specific cytotoxic T cells in FIG. 10 when the CMV T-cell antigen epitope is presented on tumor cells using the inCT99†CMV antibody, the effect of various inCT99†CMV fusion antibodies on the death of MDA-MB231 breast cancer cells by CMV pp65-specific cytotoxic T cells after treatment therewith was analyzed through LDH (lactate dehydrogenase) assay. LDH is an enzyme that exists in cells and is released into the cell culture medium after cell death.

FIG. 11 shows the results of an LDH (lactate dehydrogenase) assay to determine the effect of various inCT99†CMV fusion antibodies on the death of cancer cells by CMV pp65-specific cytotoxic T cells after treatment therewith.

FIG. 11a shows a scheme for the mode of administration of the antibody and the CMV pp65-specific cytotoxic T cells for LDH assay.

FIG. 11b is a graph analyzing the results of the LDH assay.

Specifically, MDA-MB-231 cells ($0.5 \times 10^4$ cells/100 1) were suspended in an RPMI medium containing 10% FBS and 1% ABAM antibiotic, attached to a 96-well plate for 12 hours, and added with fusion inCT99†CMV antibodies at a concentration of 0.2 to 1 μM, followed by culture at 37° C. in 5% $CO_2$. After 12 hours, the culture supernatant was removed, and PBMCs ($2.5 \times 10^4$ cells/200 ml) in which CMV pp65-specific cytotoxic T cells were amplified with $CMV_P495$-503 peptide in Example 6 were suspended in an RPMI medium containing 2% FBS and 1% ABAM antibiotic at an effector-cell-to-target-cell ratio of 5:1 and added to the cells. After 17 hours, in order to set the maximum LDH release control of the cells as the 100% lysis reference value, 0.1% Triton X-100 was added to wells containing only the target cells. 18 hours after addition of CMV pp65-specific cytotoxic T cells, 50 μl of the cell culture medium was transferred into a 96-well flat-bottom plate in order to quantify the extent of cell death based on the amount of lactate dehydrogenase (LDH) present in the cell culture medium of each well, and 50 of an iodonitrotetrazolium violet substrate was added to each well, followed by reaction at 37° C. for 30 minutes. When color development was sufficiently achieved, 50 μl of a stop solution was added to each well to stop the reaction, and absorbance was measured at 490 nm using a microplate reader. The maximum LDH release control is graphed as a value calculated based on 100% cell lysis.

Consequently, the inCT99†$CMV_P480$-503, inCT99†$CMV_P480$-510, inCT99†$CMV_P480$-511, inCT99†$CMV_P480$-516, and inCT99†$CMV_P480$-519 antibodies, having high ability to present the $CMV_P495$-503/HLA-A*02:01 complex on the surface of MDA-MB-231 cells, had a strong effect of inducing the death of MDA-MB-231 cancer cells by CMV pp65-specific cytotoxic T cells. Among these, the inCT99†$CMV_P480$-503 and inCT99†$CMV_P480$-516 antibodies induced a strong effect of MDA-MB-231 cancer cell death.

Example 8. Study on Mechanism of Action of inCT99†CMV Antibody Using inCT99(AAA)†CMV, Cetuximab†CMV, and Necitumumab†CMV Antibodies not Having Cytosol-Penetrating Ability In order to demonstrate that the inCT99†CMV antibody induces the death of cancer cells by CMV pp65-specific cytotoxic T cells by presenting, on the surface of cancer cells, a virus-specific T-cell antigen epitope generated through intracellular antigen processing after penetration of the antibody into the cytosol, LDH assay was performed on the above antibody and inCT99(AAA)†CMV and Cetuximab†CMV or Necitumumab†CMV antibodies, which are control antibodies that are degraded after endocytosis.

FIG. 12 shows the results of LDH (lactate dehydrogenase) assay to determine the effect of the inCT99†CMV antibody and the control antibodies inCT99(AAA)†CMV, Cetuximab†CMV, and Necitumumab†CMV on the death of cancer cells by CMV pp65-specific cytotoxic T cells after treatment therewith.

FIG. 12a shows the results of LDH assay to determine the effect of the inCT99†$CMV_P480$-503 antibody and the control antibodies inCT99(AAA)†$CMV_P480$-503 and Cetuximab†$CMV_P480$-503 on the death of cancer cells by CMV pp65-specific cytotoxic T cells after treatment in the same manner as in FIG. 11a.

Specifically, the effect of inCT99†$CMV_P480$-503, which is a fusion antibody resulting from extending only the N-terminus of the $CMV_P495$-503 T-cell epitope peptide, and the inCT99(AAA)†$CMV_P480$-503 and Cetuximab†$CMV_P480$-503 antibodies, which are the control antibodies that are degraded after endocytosis, on the death of cancer cells by CMV pp65-specific cytotoxic T cells after treatment in the same manner as in FIG. 11a of Example 7 was analyzed through LDH assay.

Consequently, not only inCT99†$CMV_P480$-503, but also inCT99(AAA)†$CMV_P480$-503 and Cetuximab†$CMV_P480$-503 antibodies, which are the control antibodies that are degraded after endocytosis, induced the effect of cancer cell death by CMV pp65-specific cytotoxic T cells. In this experiment, the $CMV_P480$-503 peptide also induced the effect of cancer cell death by CMV pp65-specific cytotoxic T cells, indicating that the $CMV_P480$-503 peptide, as well as the $CMV_P495$-503 peptide, directly bound to HLA-A*02:01 on the cancer cell surface and thus induced the effect of cancer cell death by CMV pp65-specific cytotoxic T cells. Therefore, the effect of the inCT99(AAA)†$CMV_P480$-503 and Cetuximab†$CMV_P480$-503 antibodies on inducing cancer cell death by CMV pp65-specific cytotoxic T cells is deemed to be because the $CMV_P480$-503 peptide fused to the heavy-chain terminus of inCT99(AAA) and Cetuximab induced the effect of cancer cell death by CMV pp65-specific cytotoxic T cells by directly binding to HLA-A*02:01 on the cancer cell surface.

The control antibodies inCT99(AAA)†$CMV_P480$-503 and Cetuximab†$CMV_P480$-503 increase degradation due to endocytosis with an increase in the time spent treating cancer cells, and due to the decrease in the amount of the antibody present in the cell culture medium, the amount of the antibody directly bound to HLA-A*02:01 on the cancer cell surface may be decreased, thereby lowering the effect of cancer cell death by CMV pp65-specific cytotoxic T cells. In order to prove this hypothesis, the ability of the above antibodies to induce cancer cell death by CMV pp65-specific cytotoxic T cells after 24 hours of treatment therewith was analyzed through LDH assay.

FIG. 12b shows a scheme for LDH assay to determine the ability of the above antibodies to induce cancer cell death by CMV pp65-specific cytotoxic T cells after 24 hours of treatment therewith.

FIG. 12c shows a graph analyzing the results after LDH assay in the same manner as in FIG. 12b.

Consequently, the inCT99†$CMV_P480$-503 antibody induced cancer cell death by CMV pp65-specific cytotoxic T cells at a rate of about 40% even at a low concentration of 100 nM, but the inCT99(AAA)†$CMV_P480$-503 and Cetuximab†$CMV_P480$-503 antibodies induced cancer cell death by CMV pp65-specific cytotoxic T cells at a rate of only about 20% even at a high concentration of 1 mM. Therefore, it was confirmed that the inCT99†$CMV_P480$-503 fusion antibody was able to directly bind to HLA-A*02:01 expressed on the surface of cancer cells but mostly induced cancer cell death by CTLs by presenting, on the cell surface, the virus-specific T-cell antigen epitope generated after penetration of the fusion antibody into the cytosol.

In order to demonstrate that the inCT99†CMV$_P$480-510 and inCT99†CMV$_P$480-516 antibodies, having a strong effect of inducing the death of MDA-MB-231 cancer cells by CMV pp65-specific cytotoxic T cells among the inCT99†CMV antibodies fused with N-terminally and C-terminally extended peptides, induced the death of MDA-MB-231 cancer cells by CMV pp65-specific cytotoxic T cells by presenting the CMV$_P$495-503/HLA-A*02:01 complex on the surface of cancer cells through intracellular antigen processing after endocytosis, LDH assay was performed on the above antibodies and the control antibodies that are degraded after endocytosis.

FIG. 12$d$ shows the results of LDH assay to determine the effect of the inCT99†CMV$_P$480-510 and the control antibodies inCT99(AAA)†CMV$_P$480-510 and Cetuximab†CMV$_P$480-510 on the death of cancer cells by CMV pp65-specific cytotoxic T cells after treatment in the same manner as in FIG. 11$a$.

Consequently, the inCT99†CMV$_P$480-510 antibody induced cancer cell death by CMV pp65-specific cytotoxic T cells in a concentration-dependent manner, whereas the inCT99(AAA)†CMV$_P$480-510 and Cetuximab†CMV$_P$480-510 antibodies induced cancer cell death by CMV pp65-specific cytotoxic T cells at a rate of less than 5%. This effect of the control antibodies is deemed to be because the antibody is not localized in the cytosol after endocytosis but is degraded by lysosomes. Moreover, it was confirmed that the inCT99†CMV$_P$480-510 fusion antibody, which does not directly bind to HLA-A*02:01 expressed on the surface of cancer cells due to the extension of the N-terminus and C-terminus of the CMV$_P$495-503 T-cell epitope peptide, induced cancer cell death by CTLs by presenting the virus-specific T-cell antigen epitope generated after penetration into the cytosol on the cell surface.

FIG. 12$e$ shows the results of LDH assay to determine the effect of the inCT99†CMV$_P$480-516 antibody, the control antibodies inCT99(AAA)†CMV$_P$480-516 and Necitumumab†CMV$_P$480-516, and the Cetuximab†MMP14-CMV$_P$495-503 antibody on the death of cancer cells by CMV pp65-specific cytotoxic T cells after treatment in the same manner as in FIG. 11$a$.

Consequently, the inCT99†CMV$_P$480-516 antibody was found to induce cancer cell death by CMV pp65-specific cytotoxic T cells in a concentration-dependent manner, like but the inCT99(AAA)†CMV$_P$480-510 antibody, the control antibodies inCT99(AAA)†CMV$_P$480-516 and necitumumab†CMV$_P$480-516 were found to induce cancer cell death by CMV pp65-specific cytotoxic T cells at a rate of less than 5%, even at a concentration of 100 nM. In contrast, the Cetuximab†MMP14-CMV$_P$495-503 antibody used in conventional APEC technology induced more cancer cell death by CMV pp65-specific cytotoxic T cells than the inCT99†CMV$_P$480-516 antibody. This effect is deemed to be because the MMP14 enzyme secreted by MDA-MB-231 cancer cells in vitro cleaved the front portion of the CMV P495-503 peptide of the Cetuximab†MMP14-CMV$_P$495-503 antibody to thus liberate the CMV$_P$495-503 peptide and the T-cell epitope peptide directly bound to HLA-A*02:01 expressed on the surface of MDA-MB-231 cancer cells.

Based on the above results, it was confirmed that the inCT99†CMV fusion antibody induced cancer cell death by CD8$^+$ cytotoxic T cells by presenting the virus-specific T-cell antigen epitope generated after penetration into the cytosol on the surface of cancer cells.

Example 9. Validation of Mechanism of Action of Leading inCT99†CMV Fusion Antibody at Cellular Level The expected mechanism of action of the inCT99†CMV fusion antibody on antigen presentation is that it binds to integrin expressed on the surface of cancer cells, is endocytosed, and is then localized in the cytosol through endosomal escape, and a CMVp epitope generated by a proteolytic system in the cytosol enters the endoplasmic reticulum to form a complex with HLA-A*02, which is then secreted through the Golgi apparatus to present the CMV P495-503 peptide, which is a T-cell antigen epitope, on the surface of cancer cells.

In order to determine that the mechanism of action of the inCT99†CMV fusion antibody is due to the expected mechanism described above, the cells were treated with MG132 as a proteasome inhibitor and nocodazole as a Golgi inhibitor and then treated with the inCT99†CMV fusion antibody, so the extent of activation of CMV pp65-specific CTLs was quantified by measuring the amount of IFN-g that was secreted through ELISA (enzyme-linked immunosorbent assay). In this experiment, treatment with MG132 and nocodazole resulted in cancer cell death at a rate of about 20%, so the ability to induce cancer cell death was not measured.

FIG. 13 shows the results of ELISA (enzyme-linked immunosorbent assay) to quantify IFN-g secretion of CMV pp65-specific cytotoxic T cells by treating cancer cells with a proteasome inhibitor and a Golgi inhibitor and then with the inCT99†CMV fusion antibody.

FIG. 13$a$ shows a scheme for the above assay.

FIG. 13$b$ shows the results of flow cytometry analysis to determine the purity of CMV pp65-specific cytotoxic T cells used in the assay.

FIG. 13$c$ shows the results of ELISA quantification to determine the effect of proteasome and Golgi inhibitors on IFN-g secretion of CMV pp65-specific cytotoxic T cells by inCT99†CMV$_P$480-503 and the control antibodies inCT99(AAA)†CMV$_P$480-503 and Cetuximab†CMV$_P$480-503.

Specifically, MDA-MB-231 cells ($0.5\times10^4$ cells/100 ml) were suspended in an RPMI medium containing 10% FBS and 1% ABAM antibiotic, attached to a 96-well plate for 11 hours, and added with a proteasome inhibitor MG132 (20 mM) and nocodazole (6.6 mM) as a Golgi inhibitor, followed by culture in an incubator containing 5% $CO_2$ at 37° C. for 1 hour. After 1 hour, the medium containing the inhibitors was replaced with fresh medium, and the cells were washed and then added with inCT99†CMV fusion antibodies at a concentration of 1 μM, followed by culture at 5% $CO_2$ and 37° C. After 12 hours, the culture supernatant was removed, and PBMCs ($2.5\times10^4$ cells/200 ml) in which CMV pp65-specific cytotoxic T cells were amplified with the CMV$_P$495-503 peptide in Example 6 were suspended in an RPMI medium containing 2% FBS and 1% ABAM antibiotic at an effector-cell-to-target-cell ratio of 5:1 and then added to the cells. After 24 hours, 100 μl of the cell culture medium was recovered to measure the concentration of IFN-γ in the cell culture medium.

In order to measure the concentration of IFN-γ in the cell culture medium, a 96-well plate for ELISA (Thermo Fisher Scientific) was coated with a human IFN-γ capture antibody for 12 hours, washed with PBST (PBS with 0.1% Tween-20), added with 1% BSA (PBS with 1% bovine serum albumin), and blocked at room temperature for 1 hour. After washing with PBST (PBS with 0.1% Tween-20), the serum was diluted 10-fold with 1% BSA, followed by reaction at room temperature for 2 hours. After washing with PBST (PBS with 0.1% Tween-20), a biotin-conjugated human IFN-γ detection antibody (Thermo Fisher Scientific) was allowed to bind thereto at room temperature for 1 hour. After washing with PBST (PBS with 0.1% Tween-20), avidin-conjugated HRP (Thermo Fisher Scientific) was allowed to bind thereto at room temperature for 30 minutes, and the cells were then washed with PBST (PBS with 0.1% Tween-20) and added with a TMB (Sigma-Aldrich Korea) substrate, after which absorbance at 450 nm was measured using a microplate reader.

Consequently, when MG132- or nocodazole-treated MDA-MB231 cells were treated with the negative control antibodies inCT(AAA)†CMV$_P$480-503 and Cetuximab†CMV$_P$480-503, there was no change in IFN-γ secretion of CMV pp65-specific cytotoxic T cells. The ability to induce IFN-γ secretion of CMV pp65-specific CTLs in the cells treated with the inCT99†CMV$_P$480-503 fusion antibody was greatly reduced by nocodazole rather than MG132. This proves that the CMV$_P$495-503/HLA-A*02:01 complex formed in the cells is secreted through the Golgi apparatus and the CMV$_P$495-503 antigen is presented on the surface of cancer cells. Since the N-terminally extended CMV$_P$495-503 T-cell epitope peptide is capable of being processed in the endoplasmic reticulum even when not degraded in the proteasome, it appears that the inCT99†CMV$_P$480-503 fusion antibody fused with the N-terminally extended CMVp T-cell epitope peptide is processed in the endoplasmic reticulum, rather than the proteasome, after which the CMV$_P$495-503/HLA-A*02:01 complex is secreted through the Golgi apparatus to thus present the CMV-specific antigen on the surface of cancer cells.

FIG. 13d shows the results of ELISA quantification to determine the effect of the inhibitors on IFN-g secretion of CMV pp65-specific cytotoxic T cells by the inCT99†CMV$_P$480-516, inCT99(AAA)†CMV$_P$480-516, and Necitumumab†CMV$_P$480-516 antibodies.

Specifically, the method for treatment with the inhibitor and the antibody is as described in FIG. 13a.

Consequently, the negative control antibodies inCT99 (AAA)†CMV$_P$480-516 and Necitumumab†CMV$_P$480-516 were found not to have the ability to induce IFN-g secretion of CMV pp65-specific cytotoxic T cells, and showed the same trend even when treated with MG132 or nocodazole. Therefore, it was confirmed that these control antibodies did not have a function of generating a virus-specific T-cell antigen through intracellular processing after penetration into the cytosol.

In contrast, the ability of the inCT99†CMV$_P$480-516 fusion antibody to induce IFN-g secretion of CMV pp65-specific cytotoxic T cells was greatly reduced through treatment with MG132 and nocodazole. This showed that the inCT99†CMV$_P$480-516 fusion antibody localized in the cytosol was degraded by the proteasome and the CMV$_P$495-503/HLA-A*02:01 complex was secreted through the Golgi apparatus to thus present the CMV$_P$495-503 antigen.

Example 10. Evaluation of Ability of inCT99†CMV$_P$480-503 Fusion Antibody to Inhibit Growth of MDA-MB-231 Tumors In Vivo In Example 8, it was demonstrated that the CMV$_P$480-503 peptide resulting from extending the N-terminus of the CMV$_P$495-503 peptide, which is a CMV T-cell epitope, also induced the effect of cancer cell death by CMV pp65-specific cytotoxic T cells by directly binding to HLA-A*02:01 on the cancer cell surface. Accordingly, in addition to the inCT99†CMV$_P$480-503 antibody, the inCT99(AAA) †CMV$_P$480-503 and Cetuximab†CMV$_P$480-503 antibodies, which are control antibodies that are degraded after endocytosis, also induced the effect of cancer cell death by CMV pp65-specific cytotoxic T cells. In order to evaluate whether these control antibodies are able to induce inhibition of tumor formation by CMV pp65-specific cytotoxic T cells by directly binding to HLA-A*02:01 on the cancer cell surface even in in-vivo tumors, or whether the effect of inhibiting tumor formation by CMV pp65-specific cytotoxic T cells is exhibited only when a virus-specific T-cell antigen epitope generated after penetration of the antibody into the cytosol is presented on the cell surface, like the inCT99†CMV$_P$480-503 antibody, the tumor-formation inhibitory effect of the antibodies was measured by constructing a model in which the MDA-MB231 human breast cancer cell line expressing HLA-A*02:01 was orthotopically transplanted into the mammary fat pads of mice.

Figure 14A:
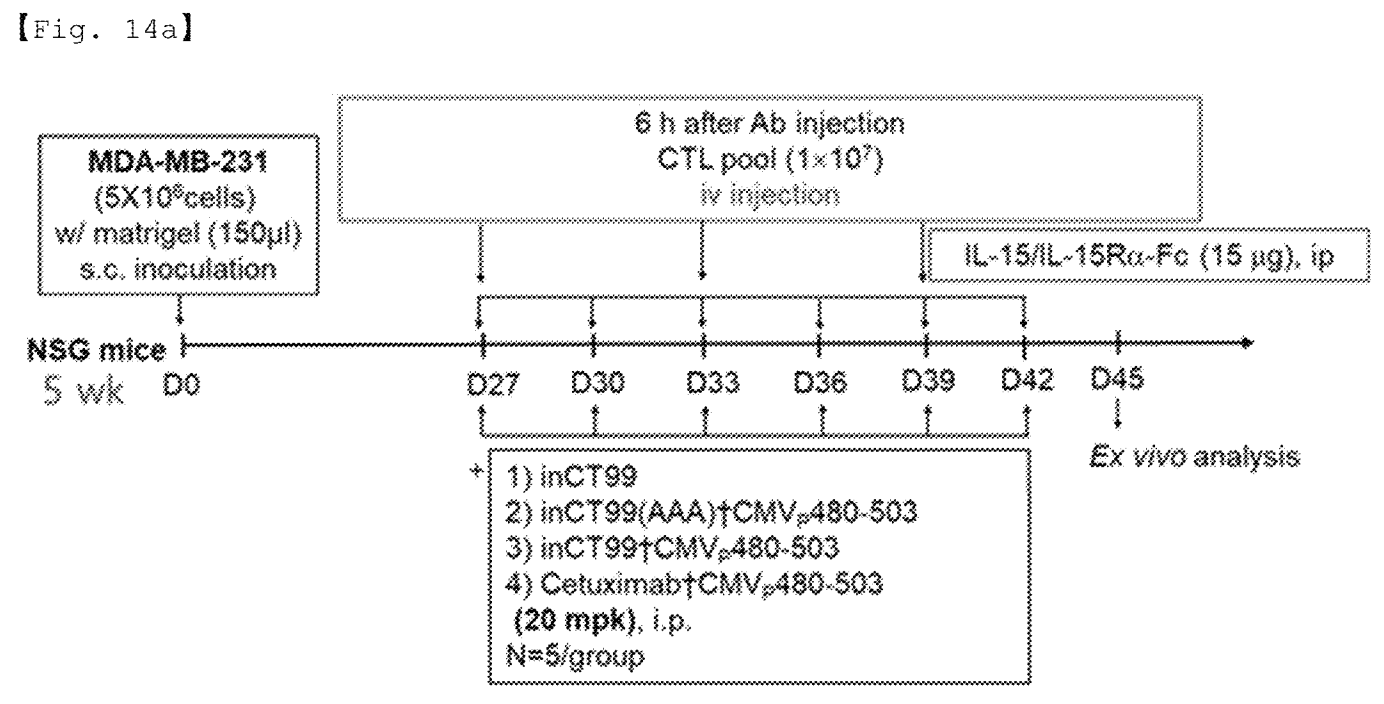

FIG. 14 shows the results of measurement of the effect of the inCT99†CMV$_P$480-503 fusion antibody on inducing the inhibition of cancer cell growth by CMV pp65-specific cytotoxic T cells in NSG mice in which MDA-MB231 cells as a human breast cancer line cell were orthotopically xenografted into mammary fat pads.

FIG. 14a shows a scheme for the interval, dose, and mode of administration of antibody/IL-15/receptor complex molecules and the interval and mode of administration of CMV pp65-specific cytotoxic T cells after tumor transplantation in the above experiment.

FIG. 14b is a graph showing a change in the tumor volume in each antibody-administered group depending on the date in the experiment of FIG. 14a.

FIG. 14c is a graph showing weights of tumors extracted from killed mice 48 hours after the last administration of the antibody in the experiment of FIG. 14a.

FIG. 14d is a photograph showing tumors extracted from killed mice 48 hours after the last administration of the antibody in the experiment of FIG. 14a.

FIG. 14e is graphs showing changes in the tumor volume in each antibody-administered group depending on the date for each mouse in the experimental result of FIG. 14a.

Specifically, an MDA-MB231 human breast cancer cell line ($5 \times 10^6$ cells) was suspended in 75 ml of DPBS, mixed with 75 ml of MATRIGEL™ (Sigma-Aldrich), and orthotopically transplanted into the mammary fat pads of NSG mice, after which mice were randomized when the tumor volume reached 100-120 mm 3 (after about 27 days), and then intraperitoneally injected with the above-described antibodies at a dose of 20 mg/kg once every 3 days. On the $27^{th}$, $33^{rd}$, and $39^{th}$ days after tumor-cell transplantation, 6 hours after administration of the fusion antibody, human-derived CMV pp65-specific CD8$^+$ cytotoxic T cells (CTLs, $1 \times 10^7$/200 ml/mouse) were intravenously injected thereto. For amplification of CMV cytotoxic T cells in NSG mice, an interleukin-15 (IL-15) and IL-15 receptor complex (15 mg/200 ml) was intraperitoneally injected thereto once every 3 days from the day of tumor administration.

In order to measure the tumor-formation inhibitory effect of the inCT99†CMV$_P$480-503 antibody in vivo, it was compared with inCT99, inCT(AAA)†CMV$_P$480-503, and Cetuximab†CMV$_P$480-503, which are the negative control antibodies in the above experiment. Consequently, the negative control antibodies inCT(AAA)†CMV$_P$480-503 and Cetuximab†CMV$_P$480-503, in which CMV$_P$480-503 peptide was loaded on HLA-A*02:01 expressed on the surface of cancer cells and thus MDA-MB231 cancer cell death was induced by CMV pp65-specific cytotoxic T cells, did not have the effect of inhibiting MDA-MB231 tumor growth in vivo in NSG mice. This result is inferred to be because it is difficult to load the CMV$_P$480-503 peptide on HLA-A*02:01 expressed on the surface of cancer cells due to the amount of the antibody present in the tumor.

In contrast, the inCT99†CMV$_P$480-503 antibody, which was able to bind directly to HLA-A*02:01 expressed on the surface of cancer cells but mostly induced cancer cell death by CMV pp65-specific cytotoxic T cells by presenting, on the surface of cancer cells, the virus-specific T-cell antigen generated after penetration of the fusion antibody into the cytosol, inhibited MDA-MB231 tumor growth by about 50% compared to the control antibodies.

Therefore, in order to present the virus-specific T-cell antigen on the surface of cancer cells within the tumor, presentation of the virus-specific antigen on the surface of cancer cells through intracellular antigen processing after penetration of the T-cell antigen-fused antibody into the cytosol is regarded as important.

Example 11. Evaluation of In-Vivo MDA-MB-231 Tumor Growth Inhibitory Activity of inCT99†CMV$_P$480-516 Fusion Antibody In Example 8, the inCT99†CMV$_P$480-516 antibody fused with the CMV$_P$480-516 peptide resulting from extending both the N-terminus and the C-terminus of the CMV$_P$495-503 peptide, which is the CMV T-cell epitope, induced cancer cell death by CMV pp65-specific cytotoxic T cells to a level lower than the Cetuximab†MMP14-CMV$_P$495-503 antibody used in conventional APEC technology. However, the control antibodies inCT99(AAA)†CMV$_P$480-503 and Cetuximab†CMV$_P$480-503, which induced the effect of cancer cell death by CMV pp65-specific cytotoxic T cells due to direct loading on HLA-A*02:01 on the cancer cell surface, did not have the effect of inhibiting tumor formation in vivo in Example 10.

Therefore, in order to evaluate the extent to which the inCT99†CMV$_P$480-516 antibody exhibits the tumor-formation inhibitory effect in vivo compared to the Cetuximab†MMP14-CMV$_P$495-503 antibody, the tumor-formation inhibitory effect of the antibodies was measured by constructing a model in which the MDA-MB231 human breast cancer cell line expressing HLA-A*02:01 was orthotopically transplanted into the mammary fat pads of mice.

FIG. 15 shows the results of measurement of the effect of the inCT99†CMV$_P$480-516 fusion antibody on inducing the inhibition of cancer cell growth by CMV pp65-specific cytotoxic T cells in NSG mice in which MDA-MB231 cells, which are a human breast cancer cell line, were orthotopically xenografted into mammary fat pads, compared to the Cetuximab†MMP14-CMV$_P$495-503 antibody used in conventional APEC technology.

FIG. 15a is a scheme showing the interval, dose, and mode of administration of antibody/IL-15/receptor complex molecules and the interval and mode of administration of CMV pp65-specific cytotoxic T cells after tumor transplantation in the above experiment.

FIG. 15b is a graph showing a change in the tumor volume in each antibody-administered group depending on the date in the experiment of FIG. 15a.

FIG. 15c is a graph showing weights of tumors extracted from killed mice 48 hours after the last administration of the antibody in the experiment of FIG. 15a.

FIG. 15d is a photograph showing tumors extracted from killed mice 48 hours after the last administration of the antibody in the experiment of FIG. 15a.

FIG. 15e is graphs showing changes in the tumor volume in each antibody-administered group depending on the date for each mouse in the experimental result of FIG. 15a.

Specifically, an MDA-MB231 human breast cancer cell line (5×10$^6$ cells) was suspended in 75 ml of DPBS, mixed with 75 ml of MATRIGEL™ (Sigma-Aldrich), and orthotopically transplanted into the mammary fat pads of NSG mice, after which the mice were randomized when the tumor volume reached 100-120 mm 3 (after about 27 days), and then intraperitoneally injected with the above-described antibodies at a dose of 20 mg/kg once every 3 days. On the 27$^{th}$, 33$^{rd}$, and 39$^{th}$ days after tumor-cell transplantation, 6 hours after administration of the fusion antibody, human-derived CMV pp65-specific cytotoxic CD8$^+$ T lymphocytes (CTLs, 1×10$^7$/200 ml/mouse) were intravenously injected thereto. For amplification of CMV pp65-specific CTLs in NSG mice, an interleukin-15 (IL-15) and IL-15 receptor complex (15 g/200 1) was intraperitoneally injected thereto once every 3 days from the day of tumor administration.

In order to measure the tumor-formation inhibitory effect of the inCT99†CMV$_P$480-516 antibody in vivo, the negative control antibodies inCT(AAA)†CMV$_P$480-516, Necitumumab†CMV$_P$480-516, inCT99, and Cetuximab†MMP14-CMV$_P$495-503 were compared therewith.

Consequently, the inCT(AAA)†CMV$_P$480-516 and Necitumumab†CMV$_P$480-516 antibodies, not having the effect of inducing MDA-MB231 cancer cell death by CMV pp65-specific cytotoxic T cells in the in-vitro experiment, were also found not to have the MDA-MB-231 tumor-formation inhibitory effect in NSG mice. However, the inCT99†CMV$_P$480-516 antibody exhibited the MDA-MB-231 tumor-formation inhibitory effect at a rate of about 60%. In particular, the Cetuximab†MMP14-CMV$_P$495-503 antibody, which was found to have a stronger effect of inducing cancer cell death by CMV pp65-specific cytotoxic T cells than the inCT99†CMV$_P$480-516 antibody in the in-vitro experiment, exhibited a lower tumor-formation inhibitory effect than the inCT99†CMV$_P$480-516 antibody in vivo, and furthermore, the tumor weight thereof was similar to that of the group treated with the inCT99 control antibody in three mice.

This result is inferred to be because it is difficult to load the CMV$_P$480-503 peptide on HLA-A*02:01 expressed on the surface of cancer cells due to the amount of the antibody present within the tumor, as in Example 10.

Therefore, in order to present the virus-specific T-cell antigen on the surface of cancer cells within the tumor, presentation of the virus-specific antigen on the surface of cancer cells through intracellular antigen processing after penetration of the T-cell antigen-fused antibody into the cytosol was confirmed to be important.

Example 12. Verification of CMV Pp65-Specific Cytotoxic T-Cell Activation Effect of inCT99†CMV$_P$480-503 Fusion Antibody In Vivo Whether the MDA-MB231 tumor growth inhibitory effect of the inCT99†CMV$_P$480-503 antibody verified in Example 10 is due to the activation of CMV pp65-specific cytotoxic T cells in tumors in practice was evaluated. To this end, the inCT99†CMV$_P$480-503 antibody and the CMV pp65-specific cytotoxic T cells were administered once to tumor-transplanted mice, after which the expression levels of a degranulation marker CD107, a cytokine IFN-g, and CD69 as an activated cytotoxic T-cell marker, generated due to the death of cancer cells by the activated cytotoxic T cells, were measured.

FIG. 16 shows the results of measurement of the effect of the inCT99†CMV$_P$480-503 fusion antibody on activation of CMV pp65-specific cytotoxic T cells in NSG mice in which MDA-MB231 cells, which are a human breast cancer cell line, were orthotopically xenografted into mammary fat pads, compared to the control antibodies inCT99(AAA) †CMV$_P$480-503 and Cetuximab†CMV$_P$480-503.

FIG. 16*a* is a scheme showing the dose and mode of administration of the antibody and the mode of administration of CMV pp65-specific cytotoxic T cells after tumor transplantation in the above experiment.

FIG. 16*b* shows the experimental results of flow cytometry analysis to determine the proportion of amplified CMV pp65-specific cytotoxic T cells for injection into NSG mice.

FIG. 16*c* shows the results of analysis of the expression level of CD107 among CMV pp65-specific cytotoxic T cells and the proportion of CMV pp65-specific cytotoxic T cells expressing CD69 and IFN-g, after the mice in each administration group were killed and tumor-infiltrating lymphocytes were isolated.

Specifically, an MDA-MB231 human breast cancer cell line ($5×10^6$ cells) was suspended in 75 ml of DPBS, mixed with 75 ml of MATRIGEL™ (Sigma-Aldrich), and orthotopically transplanted into the mammary fat pads of NSG mice, after which the mice were randomized when the tumor volume reached 100-120 $mm^3$ (after about 27 days), and then administered with the above-described antibodies at a dose of 20 mg/kg. 6 hours after administration of the fusion antibody, human-derived CMV pp65-specific cytotoxic $CD8^+$ T lymphocytes (CTLs, $1×10^7$/200 ml/mouse) were intravenously injected thereto. After 24 hours, the tumors were extracted from the mice, crushed using a wire mesh and collagenase (100 μg/ml) in a Petri dish, added with 10 ml of a medium containing 2% FBS, and centrifuged at 50 g for 5 minutes to remove parenchymal tissue. Thereafter, 1 ml of a red blood cell lysis buffer was added thereto to hemolyze red blood cells, and then the cells were washed with PBS to obtain a cell suspension. The cells isolated from the tumors were added with a PE-conjugated CMV$_P$495-503/HLA-A*02:01 pentamer, stained at room temperature for 15 minutes, washed with cold PBS (pH 7.4), added with an APC-conjugated CD8-recognizing antibody, stained at 4° C. for 30 minutes, and then washed with cold PBS (pH 7.4).

In order to measure the expression levels of CD69 and CD107, the cells were added with FITC-conjugated CD69 and CD107 antibodies and an antibody recognizing APC-conjugated CD8, stained, washed with cold PBS (pH 7.4), and analyzed through flow cytometry using a FACSCALI-BUR™ (BD Bioscience) and FLOWJO™ (Thermo Fisher Scientific). In order to measure the expression of IFN-g of CMV pp65-specific cytotoxic T cells, $10^6$ cells isolated from the tumor were suspended in 1 ml of a medium, and the medium was treated with 1× Brefeldin A (Thermo, USA), followed by culture at 5% $CO_2$ and 37° C. for 5 hours and then intracellular staining. In order to measure the expression of IFN-g present in the cells, the cells were fixed and permeabilized using a Foxp3/Transcription Factor Staining Buffer Set (Thermo Fisher Scientific), added with an antibody recognizing FITC-conjugated IFN-g, stained at 4° C. for 30 minutes, added with a permeabilization buffer, and then analyzed through flow cytometry using a FACSCALI-BUR™ (BD Bioscience) and FLOWJO™ (Thermo Fisher Scientific).

Based on the results of measurement of the expression levels of the degranulation marker CD107, the cytokine IFN-g, and the activated cytotoxic T-cell marker CD69, the negative control antibodies inCT(AAA)†CMV$_P$480-503 and Cetuximab†CMV$_P$480-503, which induced MDA-MB231 cancer cell death by CMV pp65-specific cytotoxic T cells by loading the CMV$_P$495-503 peptide on HLA-A*02: 01 expressed on the surface of cancer cells in vitro, did not have the effect of increasing the CD107, IFN-g, or CD69 expression of the CMV pp65-specific cytotoxic T cells in vivo in NSG mice. However, after administration of the inCT99†CMV$_P$480-503 antibody having the MDA-MB231 tumor growth inhibitory effect in NSG mice, the CD107 expression level of CMV pp65-specific cytotoxic T cells was increased, and the proportions of IFN-g$^+$ CMV pp65-specific cytotoxic T cells and CD69$^+$ CMV pp65-specific cytotoxic T cells were significantly increased.

Therefore, it could be confirmed that the effect of the inCT99†CMV$_P$480-503 antibody on inhibiting MDA-MB231 tumor growth in NSG mice was due to MDA-MB231 cell death by activation of CMV pp65-specific cytotoxic T cells.

The results of the above examples and the mechanism of action of the inCT99†CMV antibody compared to the control antibodies are summarized in the following table.

| T cell epitope (Virus-derived peptides) | Position number | Name of T cell epitope-fused cytotransmab | MHC-1 display at 4 C. | MHC-1 display at 37 C. | Cell lysis by CTL In vitro | Tumor growth inhibition | MOA |
|---|---|---|---|---|---|---|---|
| 9mer apitope | NLVPMVATV (SEQ ID NO: 13) | inCT99†CMV$_P$495-503 | – | – | – | nd | – |
| | | Cetuximab†MMP14CMV$_P$495-503 | ++++ | ++++ | ++++ | + | Cell surface loading |
| N-terminally extended peptide | AVFTWPPWQ AGILARNLVP MVATV (SEQ ID NO: 55) | inCT99†CMV$_P$480-503 | ++++ | +++ | ++++ | +++ | Cytosol proteasome processing + cell surface loading |
| | | inCT99(AAA)†CMV$_P$480-503 | ++++ | – | – | – | Cell surface loading |
| | | Cetuximab†CMV$_P$480-503 | ++++ | + | ++ | – | Cell surface loading |
| N- and C-terminally extended peptide | AVFTWPPWQ AGILARNLVP MVATVQGQN LKY (SEQ ID NO: 56) | inCT99†CMV$_P$480-510 | – | ++ | ++ | nd | Cytosol proteasome processing |
| | | inCT99(AAA)†CMV$_P$480-510 | – | – | – | nd | – |
| | | Cetuximab†CMV$_P$480-510 | – | – | – | nd | – |

-continued

| T cell epitope (Virus-derived peptides) | Position number | Name of T cell epitope-fused cytotransmab | MHC-1 display at 4 C. | MHC-1 display at 37 C. | Cell lysis by CTL In vitro | Tumor growth inhibition | MOA |
|---|---|---|---|---|---|---|---|
| AVFTWPPWQ AGILARNLVP MVATVQGQN LKYQEFFWD (SEQ ID NO: 57) | 480-516 | inCT99†CMV$_P$480-516 | - | +++ | +++ | +++ | Cytosol proteasome processing |
| | | inCT99(AAA)†CMV$_P$480-516 | - | - | - | - | - |
| | | Necitumumab†CMV$_P$480-516 | - | - | - | - | - |

†: G$_4$s linker (non-cleavable linker)
nd: not done

In the present invention, the inCT99†CMV$_P$480-503 antibody fused with the CMV$_P$480-503 peptide resulting from extending only the N-terminus of the CMV$_P$495-503 T-cell epitope was able to directly load the T-cell epitope on HLA-A*02:01 on the cancer cell surface in vitro but induced cancer cell death by CMV-specific cytotoxic T cells by presenting the CMV$_P$495-503 T-cell epitope generated by the proteolytic system in the cytosol to HLA-A*02:01 on the cancer cell surface, and exhibited the effect of inhibiting MDA-MB231 tumor growth in vivo in NSG mice. The direct loading of the T-cell epitope on HLA-A*02:01 on the cancer cell surface by the inCT99†CMV$_P$480-503 antibody is due to loading of the CMV$_P$480-503 peptide on HLA-A*02:01 expressed on the cancer cell surface, and thus, the negative control antibodies inCT(AAA)†CMV$_P$480-503 and Cetuximab†CMV$_P$480-503 also directly loaded the T-cell epitope on HLA-A*02:01 on the cancer cell surface in vitro. However, these control antibodies did not have the effect of inhibiting MDA-MB231 tumor growth in vivo in NSG mice. This result is inferred to be because it is difficult to load the CMV$_P$480-503 peptide on HLA-A*02:01 expressed on the surface of cancer cells due to the amount of the antibody present within the tumor.

The inCT99†CMV$_P$480-510 and inCT99†CMV$_P$480-516 antibodies fused with the CMV$_P$480-510 or CMV$_P$480-516 peptide resulting from extending both the N-terminus and the C-terminus of the CMV$_P$495-503 T-cell epitope induced cancer cell death by CMV-specific cytotoxic T cells by presenting the CMV$_P$495-503 T-cell epitope generated by the proteolytic system in the cytosol to HLA-A*02:01 on the cancer cell surface, rather than directly loading the T-cell epitope on HLA-A*02:01 on the cancer cell surface in vitro. In particular, the inCT99†CMV$_P$480-516 antibody showed an effect of inhibiting MDA-MB231 tumor growth by CMV-specific cytotoxic T cells even in vivo in NSG mice. In contrast, the negative control antibodies inCT(AAA) †CMV$_P$480-510, Cetuximab†CMV$_P$480-510, inCT(AAA) †CMV$_P$480-516, and Necitumumab†CMV$_P$480-516 did not have the ability to directly load the T-cell epitope on HLA-A*02:01 on the cancer cell surface in vitro, ultimately making it impossible to induce cancer cell death by CMV-specific cytotoxic T cells. In particular, the Cetuximab†MMP14-CMV$_P$495-503 antibody, which was found to have a stronger effect of inducing cancer cell death by CMV pp65-specific cytotoxic T cells than the inCT99†CMV$_P$480-516 antibody in the in-vitro experiment, showed a lower tumor-formation inhibitory effect than the inCT99†CMV$_P$480-516 antibody in vivo. This result is inferred to be because it is difficult to load the CMV$_P$495-

503 peptide on HLA-A*02:01 expressed on the surface of cancer cells due to the amount of the antibody present within the tumor, as in Example 10.

Therefore, in order to present the virus-specific T-cell antigen on the surface of cancer cells within the tumor, presentation of the virus-specific antigen on the surface of cancer cells through intracellular antigen processing after penetration of the T-cell antigen-fused antibody into the cytosol was confirmed to be important.

Example 13. Verification of Ability of inCT99†HPV Fusion Antibody to Present HPV$_E$11-19/HLA-A*02:01 Complex in Cancer Cell Line Having HLA-A*02:01 Genotype In Examples 1-12, it was confirmed that the inCT99†CMV fusion antibody in which a peptide corresponding to the CMV T-cell antigen epitope and a protein fragment including the same are fused to inCT99, which is a cytosol-penetrating antibody, presented a CMV pp65-derived T-cell epitope to cancer cells to thus activate CMV-specific cytotoxic T cells and inhibit tumor growth.

In order to verify whether the effect of the inCT99†viral epitope antibody is also observed in the inCT99†HPV antibody fused with the HPV16-derived antigen E7 epitope or a peptide region containing the same, the inCT99†HPV$_E$11-19 and inCT99†HPV$_E$1-19 fusion antibodies were constructed as in Example 1 and purified in the same manner as in Example 3. Since cytotoxic T cells specific to the HPV16-derived antigen E7 epitope are absent in PBMCs of normal donors, whether the above antibodies present the HPV$_E$11-19 antigen on the cancer cell surface within tumor cells was verified using 7-1, which is a T-cell receptor (TCR)-like antibody that recognizes the HPV$_E$11-19/HLA-A*02:01 complex.

FIG. 17 shows the results of flow cytometry analysis to determine the ability of inCT99†HPV$_E$11-19 and inCT99†HPV$_E$1-19 fusion antibodies to present the T-cell antigen epitope to HLA-A*02:01 through intracellular antigen processing.

FIG. 17a shows a scheme for analyzing the ability of the antibodies to present the T-cell antigen epitope to HLA-A*02:01 through intracellular antigen processing at 37° C.

FIG. 17b shows the results of flow cytometry analysis after treatment with the antibodies at various concentrations in the same manner as in FIG. 17a.

FIG. 17c shows the results of flow cytometry analysis to determine the ability of the antibodies to present the T-cell antigen epitope to HLA-A*02:01 after treatment over time in the same manner as in FIG. 17a.

Specifically, in a 12-well plate, an MDA-MB-231 cell line was diluted at a density of $1.8 \times 10^5$ cells/ml per well in an RPMI medium containing 10% FBS and 1% ABAM antibiotic and then cultured at 37° C. and 5% $CO_2$ for 12 hours, after which the medium was removed and the inCT99, inCT99-HPV$_E$†1-19, and inCT99-HPV$_E$†11-19 fusion antibodies were diluted to concentrations of 4 μM, 2 μM, 1 μM, 0.5 μM, and 0.1 μM in 400 μl of a medium, followed by culture at 37° C. and 5% $CO_2$ for 12 hours. Thereafter, the medium was removed and the cells were washed with DPBS and treated with 100 μl of a trypsin-EDTA solution per well at 37° C. for 3 minutes to thus separate the cells from the plate. 1 ml of an RPMI medium containing 10% FBS was added to each well to neutralize trypsin-EDTA, and the cells were recovered and centrifuged at 1300 rpm for 3 minutes to remove the supernatant. The cells were washed with 1 ml of a FACS buffer and centrifuged to remove the supernatant. The cell pellets in each well were lysed with 200 μl of a FACS buffer and divided into two samples, one sample of which was used as a control containing only a secondary antibody. A T-cell receptor-like antibody 7-1 clone that specifically recognizes the HPV$_E$11-19/HLA-A*02:01 complex was diluted to a concentration of 2 nM in 100 μl of a FACS buffer and added to each sample, followed by reaction at 4° C. for 1 hour. After each sample was washed with 1 ml of a FACS buffer, a F(ab')$_2$ antibody that specifically recognizes ALEXA647™ (red fluorescence)-conjugated mouse Fc was diluted 1:1200 in 100 μl of a FACS buffer, followed by reaction at 4° C. for 30 minutes. After washing with 1 ml of a FACS buffer, analysis was performed through flow cytometry.

Consequently, formation of the HPV$_E$11-19/HLA-A*02:01 complex on the surface of MDA-MB-231 cancer cells depending on the concentration of the inCT99†HPV$_E$11-19 and inCT99†HPV$_E$1-19 fusion antibodies was confirmed based on the extent of binding of the TCR-like antibody.

In order to observe the extent of formation of the peptide-HLA-A*02:01 complex depending on the treatment time of the inCT99†HPV fusion antibody, with reference to the results of FIG. 17b, in which the efficiency of formation of the HPV$_E$11-19/HLA-A*02:01 complex was proportional to the concentration of the fusion antibody, the MDA-MB-231 cancer cells were treated with the inCT99-HPV$_E$†1-19 fusion antibody at a concentration of 2 μM, and after 0.5 to 48 hours, the HPV$_E$11-19/HLA-A*02:01 complex presented on the surface of the cancer cells was detected using the 7-1 antibody.

Consequently, when the antibody treatment time was increased from 1 hour to 18 hours, the HPV$_E$11-19/HLA-A*02:01 complex presented on the cancer cell surface was increased, and after 18 hours, it was observed that the antigen-presenting ability was decreased.

Based on the above results, it was demonstrated that, even when different type of virus-derived T-cell antigen such as HPV, as well as the peptide comprising the CMV T-cell antigen, is fused to inCT99, which is the cytosol-penetrating antibody, the inCT99†viral epitope antibody is endocytosed by binding to the integrin expressed on the surface of cancer cells and is then localized in the cytosol through endosomal escape, and the virus-derived epitope generated by the proteolytic system in the cytosol enters the endoplasmic reticulum to form a complex with HLA-A*02, which is then secreted through the Golgi apparatus, thereby presenting the T-cell antigen epitope on the surface of cancer cells.

Example 14. Verification of Tumor-Formation Inhibitory Effect of inCT99†OVA250-264 Fusion Antibody Whether the tumor growth inhibitory effect is capable of being induced in practice in immunocompetent mice having immune cells based on the tumor growth inhibitory effect of the inCT99†CMV antibody and the CMV pp65-specific cytotoxic T-cell activation effect thereof observed in Examples 10-12 was evaluated. To this end, an inCT99†OVA250-264 antibody, in which peptide 250-264 resulting from extending the N-terminus of peptide 257-264 of ovalbumin (OVA) having ability to bind to a mouse cancer-cell MHC-I antigen H-2K$^b$ is fused to a cytosol-penetrating antibody inCT99, was constructed to verify the effect of cancer cell death by CD8OVA1.3 cells, which are OVA-specific cytotoxic T cells that recognize the OVA257-264/H-2K$^b$ complex, and the tumor growth inhibitory effect in immunocompetent mice.

In the present invention, the negative control antibodies that were used were an inCT(AAA)†OVA250-264 antibody not having cytosol-penetrating ability and an inCT99†OVA323-339 fusion antibody fused with OVA peptide 323-339 not having ability to bind to the MHC-I antigen H-2K$^b$.

In the inCT(AAA)†OVA250-264 antibody, $^{92}$WYW$^{94}$, which is an endosomal escape motif present in VL-CDR3 of the inCT99 antibody, is mutated to $^{92}$AAA$^{94}$, and $^{95}$WYW$^{98}$, which is an endosomal escape motif present in VH-CDR3 thereof, is mutated to $^{95}$AAA$^{98}$. Therefore, the inCT(AAA)†OVA250-264 antibody, which is endocytosed by binding to integrin αvβ3 and αvβ5 receptors, does not penetrate the cytosol because it cannot escape from the endosome, making it impossible to present the virus-specific T-cell antigen epitope on the cell surface.

The inCT99†OVA323-339 fusion antibody does not have the ability to bind to the MHC-I antigen H-2K$^b$, and thus, even when it is endocytosed by binding to integrin αvβ3 and αvβ5 receptors and penetrates the cytosol through endosomal escape, it cannot bind to H-2K$^b$ present in the endoplasmic reticulum, making it impossible to present the OVA257-264/H-2K$^b$ complex on the surface of cancer cells.

The antibodies described above were constructed and purified in the same manner as in Examples 1-3, and then used in the experiment.

Before animal testing, whether the inCT99†OVA250-264 fusion antibody is capable of activating virus-specific cytotoxic T cells by presenting a virus-derived T-cell epitope to cancer cells was confirmed.

| Name of T cell epitope-fused cytotransmab | Position number | Ovalbumin fragment sequence | | MHC restriction | Endosome escape restriction |
|---|---|---|---|---|---|
| inCT99†OVA250-264 | 250-264 | SGLEQLESIINFEKL | N-term extended | H-2K$^b$ | YES |
| inCT99(AAA)†OVA250-264 | 250-264 | SGLEQLESIINEEKL | N-term extended | H-2K$^b$ | No |
| inCT99†OVA323-339 | 323-339 | ISQAVHAAHAEINEAGR | | I-A$^a$ | YES |

FIG. 18 shows the results of flow cytometry analysis to determine the ability of various inCT99†OVA250-264 fusion antibodies to bind to cell-surface H-2K$^b$ and to present the T-cell antigen epitope to H-2K$^b$ through intracellular antigen processing and the results of LDH assay to determine the effect of cancer cell death by OVA-specific cytotoxic T cells.

FIG. 18a shows the results of flow cytometry analysis to determine the ability of the inCT99†OVA250-264 fusion antibody to bind to cell-surface H-2K$^b$ at 4° C. after treatment with the antibody in the same manner as in FIGS. 9a and 9b and the ability of the inCT99†OVA250-264 fusion antibody to present the T-cell antigen epitope to H-2K$^b$ through intracellular antigen processing at 37° C.

In a detailed method for analyzing the ability of the inCT99†OVA250-264 fusion antibody to bind to cell-surface H-2K$^b$ at 4° C., in order to measure whether the inCT99†OVA250-264 fusion antibody directly binds to HLA-A*02:01 expressed on the surface of cancer cells, MC38 cells expressing integrin αvβ3 and αvβ5 receptors and expressing H-2K$^b$ were prepared at a density of $3.0\times10^5$ cells/ml in an RPMI medium containing 10% FBS and 1% ABAM antibiotic, added with the inCT99†OVA250-264 fusion antibody and the negative control antibodies such as inCT(AAA)†OVA250-264 antibody and inCT99†OVA323-339 fusion antibody at a concentration of 4 μM, and allowed to react at 5% CO$_2$ and 37° C. for 3 hours. Here, a positive control group was treated with OVA257-264 peptide at 4 μM, and a negative control group was added with a histidine buffer in which the antibody was dissolved. After 3 hours, centrifugation was performed at 1300 rpm for 3 minutes to remove the supernatant containing the antibody and peptide not bound to the cells, and the cells were washed with a FACS buffer and then centrifuged at 1300 rpm for 3 minutes to remove the supernatant. For each sample, $1.5\times10^5$ cells were prepared, and a 25-D1.16 antibody (BioLegend), which is a monoclonal antibody that specifically recognizes the OVA257-264/H-2K$^b$ complex, was diluted to a concentration of 4 nM in 100 μl of a FACS buffer and added thereto, followed by reaction at 4° C. for 1 hour. After each sample was washed with 1 ml of a FACS buffer, a F(ab')$_2$ antibody that specifically recognizes PE fluorescence-conjugated mouse Fc was diluted 1:1200 in 100 μl of a FACS buffer, followed by reaction at 4° C. for 30 minutes. After washing with 1 ml of a FACS buffer, analysis was performed through flow cytometry and FLOWJO™.

Consequently, it was confirmed that both the inCT99†OVA250-264 antibody, which is an antibody fused with a peptide resulting from extending only the N-terminus of the OVA257-264 T-cell epitope peptide, and the inCT99 (AAA)†OVA250-264 antibody, which is the negative control antibody, directly bound to H-2K$^b$ on the surface of cancer cells. These results appear that, due to the ability of the CMV$_P$480-503 peptide to bind to HLA-A*02:01 on the cancer cell surface, the inCT99†CMV$_P$480-503 antibody fused with the peptide resulting from extending the N-terminus of the CMV$_P$495-503 and peptide the control antibodies inCT99(AAA)†CMV$_P$480-503 and Cetuximab†CMV$_P$480-503 manifest the same trend as the result of direct binding to HLA-A*02:01 on the cancer cell surface. Therefore, the ability of the inCT99†OVA250-264 antibody and the negative control antibody inCT99(AAA) †OVA250-264 to directly bind to H-2K$^b$ on the surface of cancer cells is deemed to be due to the ability of the OVA250-264 peptide to bind to H-2K$^b$.

In order to evaluate whether the inCT99†OVA250-264 fusion antibody presents the OVA257-264/H-2K$^b$ complex on the surface of cancer cells through intracellular antigen processing at 37° C., MC38 cells expressing integrin αvβ3 and αvβ5 receptors and expressing H-2K$^b$ were prepared at a density of $1.5\times10^5$ cells/ml in an RPMI medium containing 10% FBS and 1% ABAM antibiotic, attached to a 24-well plate for 12 hours, added with the inCT99†OVA250-264 fusion antibody and the control antibodies inCT99(AAA) †OVA250-264 and inCT99†OVA323-339 at a concentration of 4 μM, and allowed to react at 37° C. and 5% CO$_2$ for 18 hours. Here, a positive control group was treated with OVA257-264 peptide at 4 μM, and a negative control group was added with a histidine buffer in which the antibody was dissolved. After 18 hours, the antibody-treated medium was recovered and washed with 1 ml of DPBS, and MC38 cells attached to the bottom were recovered by scraping using a yellow tip, suspended in 1 ml of DPBS, and then centrifuged at 1300 rpm for 3 minutes. The supernatant containing the antibody and peptide not bound to the cells was removed, and the cells were washed with a FACS buffer and then centrifuged at 1300 rpm for 3 minutes to remove the supernatant. For each sample, $1.5\times10^5$ cells were prepared, and a 25-D1.16 antibody (BioLegend), which is a monoclonal antibody that specifically recognizes the OVA257-264/H-2K$^b$ complex, was diluted to a concentration of 4 nM in 100 μl of a FACS buffer and added thereto, followed by reaction at 4° C. for 1 hour. After each sample was washed with 1 ml of a FACS buffer, a F(ab')$_2$ antibody that specifically recognizes PE fluorescence-conjugated mouse Fc was diluted 1:1200 in 100 μl of a FACS buffer, followed by reaction at 4° C. for 30 minutes. After washing with 1 ml of a FACS buffer, analysis was performed through flow cytometry and FLOWJO™.

Consequently, the inCT99 antibody, inCT99(AAA) †OVA250-264, and inCT99†OVA323-339, which are the negative control antibodies, did not present the OVA257-264/H-2K$^b$ complex on the surface of MC38 cells. However, the inCT99†OVA250-264 antibody, which is an antibody fused with a peptide resulting from extending only the N-terminus of the OVA257-264 T-cell epitope peptide, was confirmed to present the OVA257-264/H-2K$^b$ complex on the surface of MC38 cells by presenting, on the cell surface, the virus-specific T-cell antigen epitope generated through intracellular antigen processing after penetration of the antibody into the cytosol.

Therefore, in order to present the virus-specific T-cell antigen on the cancer cell surface in tumor cells, presentation of the virus-specific antigen on the surface of cancer cells through intracellular antigen processing after penetration of the T-cell antigen-fused antibody into the cytosol was confirmed to be important.

When cancer cells were treated with the inCT99†OVA250-264 antibody, whether the effect of cancer cell death was induced by OVA-specific cytotoxic T cells was measured.

FIG. 18b shows the results of LDH assay to determine the effect of cancer cell death after H-2K$^b$-expressing MC38 cells were treated with the inCT99†OVA250-264 antibody and then with OVA-specific cytotoxic T cells in different amounts.

Specifically, MC38 cells (0.3×10$^4$ cells/100 ml) were suspended in an RPMI medium containing 10% FBS and 1% ABAM antibiotic, attached to a 96-well plate for 12 hours, and added with the inCT99†OVA250-264 fusion antibody and the control antibodies inCT99(AAA)†OVA250-264 and inCT99†OVA323-339 at a concentration of 1 μM, followed by culture at 5% CO$_2$ and 37° C. After 12 hours, the culture supernatant was removed, and CD8OVA1.3 cells, which are OVA-specific cytotoxic T cells that recognize the OVA257-264/H-2K$^b$ complex, were suspended in an RPMI medium containing 2% FBS and 1% ABAM antibiotic at effector-cell-to-target-cell ratios of 0.2: 1, 1:1, and 5:1 and then added to the cells. After 17 hours, in order to set the maximum LDH release control of the cells as the 100% lysis reference value, 0.1% Triton X-100 was placed in the wells containing only the target cells. 18 hours after addition of CD8OVA1.3 cells, 50 μl of the cell culture medium was transferred to a 96-well flat-bottom plate in order to quantify the extent of cell death based on the amount of lactate dehydrogenase (LDH) present in the cell culture medium of each well, and 50 μl of an iodonitrotetrazolium violet substrate was added to each well, followed by reaction at 37° C. for 30 minutes. When color development was sufficiently achieved, 50 μl of a stop solution was added to each well to stop the reaction, and absorbance at 490 nm was measured using a microplate reader. The maximum LDH release control is graphed as a value calculated based on 100% cell lysis.

Consequently, the control antibodies inCT99(AAA)†OVA250-264 and inCT99†OVA323-339 that failed to present the OVA257-264/H-2K$^b$ complex on the surface of MC38 cells at 37° C. did not have the effect of inducing the death of MC38 cancer cells by CD8OVA1.3 cells, which are OVA257-264-specific cytotoxic T cells that recognize the OVA257-264/H-2K$^b$ complex. However, the inCT99†OVA250-264 fusion antibody, which presented the OVA257-264/H-2K$^b$ complex on the surface of MC38 cells, had a stronger effect of inducing the death of MC38 cancer cells with an increase in the number of CMV pp65-specific cytotoxic T cells.

Therefore, in order to realize cancer cell death by antigen-specific cytotoxic T cells by presenting the virus-specific T-cell antigen on the cancer cell surface in tumor cells, presentation of the virus-specific antigen on the surface of cancer cells through intracellular antigen processing after penetration of the T-cell antigen-fused antibody into the cytosol was confirmed to be important.

Whether the inCT99†OVA250-264 fusion antibody, which induces cancer cell death by OVA-specific cytotoxic T cells by presenting the OVA257-264/H-2K$^b$ complex on the surface of MC38 cells, has a tumor-formation inhibitory effect in immunocompetent mice was verified.

FIG. 19 shows the results of measurement of the effect of the inCT99†OVA250-264 fusion antibody on inducing the inhibition of cancer cell growth by OVA257-264-specific cytotoxic T cells after MC38 cells, which are a mouse colorectal cancer cell line, were allografted to the back of C57BL/6 immunocompetent mice.

FIG. 19a shows a scheme for the interval, dose, and mode of administration of the antibody and the interval and mode of administration of OVA257-264-specific cytotoxic T cells after tumor transplantation in the above experiment.

FIG. 19b is a graph showing a change in the tumor volume in each antibody-administered group depending on the date in the experiment of FIG. 19a.

FIG. 19c is graphs showing changes in the tumor volume in each antibody-administered group for each mouse in the experiment of FIG. 19b.

Specifically, an MC38 mouse colorectal cancer cell line (2×10$^5$ cells) was suspended in 100 ml of DPBS and allografted to the back of C57BL/6 immunocompetent mice, and the mice were randomized when the tumor volume reached 100-120 mm$^3$ (after about 10 days) and then injected intraperitoneally with the inCT99†OVA250-264 antibody and the negative control antibodies inCT99(AAA)†OVA250-264 and inCT99†OVA323-339 at a dose of 20 mg/kg once every 3 days. On the 10$^{th}$ and 16$^{th}$ days after tumor-cell transplantation, 6 hours after administration of the fusion antibody, CD8OVA1.3 cells (1×10$^7$/200 ml/mouse), which are OVA257-264-specific cytotoxic T cells, were intravenously injected thereto.

In order to measure the tumor-formation inhibitory effect of the inCT99†OVA250-264 antibody in vivo, it was compared with the negative control antibodies inCT99(AAA)†OVA250-264, inCT99†OVA323-339, and inCT99 in the above experiment. Consequently, the inCT99(AAA)†OVA250-264 antibody, which is the negative control antibody in which the OVA257-264 peptide was loaded on H-2K$^b$ expressed on the surface of cancer cells, did not have the effect of inhibiting MC38 tumor growth in C57BL/6 immunocompetent mice.

In contrast, the inCT99†OVA250-264 antibody, which was able to directly bind to H-2K$^b$ expressed on the surface of cancer cells but mostly induced cancer cell death by OVA257-264-specific cytotoxic T cells by presenting, on the surface of cancer cells, the virus-specific T-cell antigen generated after penetration of the fusion antibody into the cytosol, inhibited MC38 tumor growth by about 50% compared to the control antibodies.

Therefore, in order to present the virus-specific T-cell antigen on the cancer cell surface within the tumor, presentation of the virus-specific antigen on the surface of cancer cells through intracellular antigen processing after penetration of the T-cell antigen-fused antibody into the cytosol is regarded as important.

FIG. 20 schematically shows the mechanism of action of a general-purpose therapeutic cancer vaccine by which a virus-specific epitope is expressed on the surface of cancer cells using a fusion antibody in which an antigen of virus-derived epitope peptide is fused to a cytosol-penetrating antibody and cancer cells are eliminated using virus-specific cytotoxic T cells already present in the tumor patient's body.

As shown in FIG. 20, a fusion antibody (viral epitope-fused cytotransmab) in which an antigen of virus-derived epitope peptide fused with a virus-specific T-cell antigen epitope or a peptide comprising the same is fused to a cytosol-penetrating antibody is endocytosed by binding to the membrane protein receptor on the surface of cells overexpressed in tumor tissue and is then localized in the cytosol through endosomal escape, and a virus-specific epitope generated by the proteolytic system in the cytosol enters the endoplasmic reticulum, binds to MHC-I, and is secreted through the Golgi apparatus to thus express the virus-specific epitope on the surface of cancer cells. Virus-specific cytotoxic T cells already present in the tumor patient's body eliminate cancer cells expressing the virus-specific epitope, so the fusion antibody (viral epitope-fused cytotransmab) in which the antigen of virus-derived epitope peptide is fused to the cytosol-penetrating antibody can act as a general-purpose therapeutic cancer vaccine.

INDUSTRIAL APPLICABILITY

According to the present invention, a fusion antibody is capable of penetrating a cytosol in a cell- or tissue-specific manner, and thus a virus-specific T-cell antigen epitope generated by a proteolytic system in the cytosol after penetration of the fusion antibody into the cytosol enters the endoplasmic reticulum and binds to MHC-I to form a viral peptide/HLA-A*02:01 complex (pMHC), and this pMHC can be secreted through the Golgi apparatus, thereby presenting the virus-specific T-cell antigen epitope on the cell surface.

Therefore, the fusion antibody according to the present invention or a composition including same expresses a virus-specific epitope on the surface of target cells to thus eliminate target cells, for example cancer cells presenting the virus-specific epitope, using virus-specific cytotoxic CD8⁺ T cells already present in the patient's body, so it can be used for general-purpose treatment for various types of cancer.

Specifically, when the antigen of virus-derived CD8⁺ T-cell antigen epitope is delivered to the cytosol of cancer cells through the fusion antibody according to the present invention and the viral peptide-MHC-I complex (pMHC) is expressed on the surface of cancer cells and thus the cancer cells are recognized as virus-infected cells, antiviral cytotoxic T cells circulating in the cancer patient's body recognize the cancer cells as virus-infected cells to thus kill the cancer cells, so the fusion antibody can be used for treatment to eliminate cancer.

In addition, the fusion antibody according to the present invention delivers an antigen to the cytosol of tumor cells, and the peptide delivered to the cytosol is cleaved through intracellular antigen processing to generate a peptide that binds to MHC-I and display the same on MHC-I.

Therefore, by delivering the CD8⁺ T-cell antigen epitope (8-11 amino acid residues) and the peptide comprising the same (peptide including 12 or more amino acid residues) to the cytosol, the T-cell antigen epitope can be ultimately displayed to the antigen-presenting molecule MHC-I on the surface of target cells, so antigen peptides having various lengths can be used for cancer vaccines and the like.

The fusion antibody according to the present invention is capable of presenting, to the antigen-presenting molecule MHC-I on the surface of target cells, the CD8⁺ T-cell antigen epitope derived from antigens such as various viruses, cytomegalovirus (CMV), human papilloma virus 16 (HPV16), Epstein-Barr virus (EBV), influenza virus, Covid 19 (severe acute respiratory syndrome-coronavirus-2, SARS-COV-2) virus, and the like. Therefore, when the fusion antibody containing the antigen of virus is administered to a cancer patient who is infected with a virus and has immunity thereto, cancer cells can be recognized as virus-infected cells and thus eliminated using repurposed virus-specific cytotoxic CD8⁺ T cells already present in the cancer patient's body, so the fusion antibody of the present invention can be used for general-purpose treatment for various types of cancer.

In addition, the fusion antibody according to the present invention in which a viral antigen-derived T-cell antigen epitope peptide or a peptide comprising the same is fused to a cytosol-penetrating antibody is capable of maximizing the ability to inhibit tumor growth because various viral epitopes can be fused thereto, so virus-specific cytotoxic CD8⁺ T cells that are mainly present in cancer patients can be used for the CD8⁺ T-cell epitope included therein or the peptide comprising the same.

In addition, the fusion antibody according to the present invention, in which the CD8⁺ T-cell antigen epitope or the peptide comprising the same is fused to a cell- or tissue-specific cytosol-penetrating antibody, is developed to target all cells having nuclei expressing MHC-I, in addition to target cells such as cancer cells, and can thus present the CD8⁺ T-cell antigen epitope to MHC-I on the surface of the target cells.

The fusion antibody according to the present invention in which the antigen of virus-derived peptide and the cytosol-penetrating antibody are fused to each other facilitates the development of a therapeutic drug at high production yield, and thus can be expected to exhibit effective anticancer activity through administration alone or in combination with an existing therapeutic agent.

[Sequence List Free Text]

An electronic file is attached.

---

The invention claimed is:

1. A fusion antibody in which a peptide comprising a CD8$^+$ T-cell antigen epitope comprising a sequence selected from the group consisting of SEQ ID NOs: 13 to 16, 18, 19, 21 to 24, 26 to 33, 35 and 36 is fused to a cell- or tissue-specific cytosol-penetrating antibody, wherein the cytosol-penetrating antibody comprises a heavy chain comprising the sequence of SEQ ID NO: 1 and a light chain comprising the sequence of SEQ ID NO: 2, wherein the fusion antibody is endocytosed into a cell by the cytosol-penetrating antibody and is then localized in a cytosol through endosomal escape.

2. The fusion antibody according to claim 1, wherein the cell is a cancer cell, virus- or pathogenic microorganism-infected cell, mast cell, eosinophil, basophil, neutrophil, helper T cell (CD4$^+$ T cell), cytotoxic T cell (CD8$^+$ T cell), macrophage, epithelial cell, muscle cell, skin cell, or stem cell.

3. The fusion antibody according to claim 1, wherein the peptide comprising the CD8$^+$ T-cell antigen epitope is originated from an antigen of a virus that causes infection in a human.

4. The fusion antibody according to claim 3, wherein the CD8$^+$ T-cell antigen epitope is a T-cell antigen epitope originated from viral proteins of cytomegalovirus (CMV), human papilloma virus (HPV), Epstein-Barr virus (EBV), influenza A virus (IAV), or Covid-19 (severe acute respiratory syndrome-coronavirus-2, SARS-COV-2).

5. The fusion antibody according to claim 1, wherein one or more peptides comprising the CD8$^+$ T-cell antigen epitope are inserted into an interior of the cytosol-penetrating antibody, or is fused to the N-terminus or the C-terminus of a light chain or a heavy chain of the cytosol-penetrating antibody.

6. The fusion antibody according to claim 5, wherein the one or more peptides comprising the CD8$^+$ T-cell antigen epitope are inserted into a middle portion of a hinge region, heavy-chain variable region, CH1, CH2, or CH3 domain, light-chain variable region, or light-chain constant region domain (CL) of the cytosol-penetrating antibody.

7. The fusion antibody according to claim 5, wherein the one or more peptides comprising the CD8$^+$ T-cell antigen epitope are fused to the C-terminus of a heavy chain and/or the C-terminus of a light chain of the cytosol-penetrating antibody.

8. The fusion antibody according to claim 7, wherein one or two or more peptides each containing one or more of the CD8$^+$ T-cell antigen epitopes are fused to the C-terminus of the heavy chain of the cytosol-penetrating antibody.

9. The fusion antibody according to claim 1, wherein the cytosol-penetrating antibody and the peptide comprising the CD8$^+$ T-cell antigen epitope are fused to each other using a non-cleavable linker or a cleavable linker that is cleaved in an endosome.

10. The fusion antibody according to claim 9, wherein the linker comprises G$_4$S (SEQ ID NO: 4) or G$_4$SGFLG (SEQ ID NO: 5).

11. The fusion antibody according to claim 1, further comprises a material targeting a target-cell-specific antigen.

12. The fusion antibody according to claim 11, wherein the target-cell-specific antigen is selected from the group consisting of EpCAM (epithelial cell adhesion molecule), EGFR (epidermal growth factor receptor, Her1), Her2/Neu, Her3, Her4, EGFRvIII, integrin αvβ3, integrin αvβ5, integrin αvβ6, IGFR (insulin-like growth factor), mesothelin, CEA (carcinoembryonic antigen), MUC1 (mucin 1), CD20 (B-lymphocyte antigen CD20), CD19, CD22, CD25, CD33, CD38, CD123, Lewis Y, PD-1 (programmed cell death protein 1), PD-L1 (programmed death-ligand 1), CTLA4 (cytotoxic T-lymphocyte-associated protein 4), PSMA (prostate-specific membrane antigen), Ang2 (angiopoietin-2), PDGF-R (platelet-derived growth factor receptor), VEGF-R (vascular endothelial growth factor receptor), neuropilin, c-Met, pathogenic virus-specific antigen, pathogenic microorganism-specific antigen, mast-cell-specific antigen, eosinophil-specific antigen, basophil-specific antigen, neutrophil-specific antigen, helper T cell (CD4$^+$ T cell)-specific antigen, cytotoxic T-cell (CD8$^+$ T cell)-specific antigen, macrophage-specific antigen, epithelial-cell-specific antigen, muscle-cell-specific antigen, skin-cell-specific antigen, stem-cell-specific antigen, and a combination thereof.

13. The fusion antibody according to claim 11, wherein the material targeting the target-cell-specific antigen is linked to the fusion antibody through genetic fusion, linker-mediated coupling, or covalent linkage.

14. The fusion antibody according to claim 11, wherein the material targeting the target-cell-specific antigen is a ligand, an oligopeptide, an antibody or a fragment thereof, or an aptamer, which is capable of specifically binding to the target-cell-specific antigen.

15. A composition comprising the fusion antibody according to claim 1.

16. A method comprising administering the fusion antibody according to claim 1 or a composition comprising the fusion antibody, to a subject, wherein the method is:

(i) treating cancers, autoimmune diseases, or infectious diseases, and/or (ii) presenting a T-cell antigen epitope on a surface of a target cell.

17. A polynucleotide encoding the fusion antibody according to claim 1.

18. A recombinant expression vector comprising the polynucleotide according to claim 17.

19. A host cell comprising the recombinant expression vector according to claim 18.

20. A method of producing a fusion antibody comprising culturing the host cell according to claim 19 and recovering a produced fusion antibody.

21. The method according to claim 20, comprising:

(1) preparing a heavy-chain expression vector cloned with nucleic acids encoding a heavy chain comprising an endosomal escape cytosol-penetrating heavy-chain variable region (VH) and a heavy-chain constant region of a human antibody comprising CH1, hinge, CH2 and CH3 and a T-cell antigen epitope or a peptide comprising the epitope fused to the C-terminus of the heavy chain;

(2) preparing an light-chain expression vector cloned with nucleic acids encoding an amino acid of a light chain comprising an endosomal escape cytosol-penetrating light-chain variable region (VL) and a light-chain constant region (CL) of the human antibody;

(3) expressing a fusion antibody in an intact immunoglobulin form in which a peptide comprising a human T cell antigen epitope is fused to a cytosol-penetrating antibody by co-transfecting animal cells for protein expression with the heavy-chain expression vector and the light-chain expression vector; and (4) purifying and recovering the expressed fusion antibody.

22. A method of presenting a CD8$^+$ T-cell antigen epitope on a surface of a target cell, in which a peptide comprising the CD8$^+$ T-cell antigen epitope is delivered into a cytosol in a form of a fusion antibody in which the peptide comprising the CD8⁺ T-cell antigen epitope comprising a sequence selected from the group consisting of SEQ ID Nos. 13 to 16, 18, 19, 21 to 24, 26 to 33, 35 and 36 is fused to a cell- or tissue-specific cytosol-penetrating antibody, wherein the cytosol-penetrating antibody comprises a heavy chain comprising the sequence of SEQ ID No: 1 and a light chain comprising the sequence of SEQ ID No: 2, and wherein the fusion antibody is endocytosed into the cell and then localized in the cytosol through endosomal escape, whereby the CD8 T-cell antigen epitope is processed and then presented on the surface of the target cell.

\* \* \* \* \*

SEQUENCE LISTING

<160> NUMBER OF SEQ ID NOS: 59

<210> SEQ ID NO 1
<211> LENGTH: 446
<212> TYPE: PRT
<213> ORGANISM: Artificial Sequence
<220> FEATURE:
<223> OTHER INFORMATION: inCT99 heavy chain

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30
```

-continued

```
Ser Met Ser Trp Val Arg Gln Ala Pro Gly Lys Gly Leu Glu Trp Val
        35                  40                  45

Ser Tyr Ile Ser Arg Thr Ser His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Trp Tyr Trp Met Asp Leu Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

-continued

```
<210> SEQ ID NO 2
<211> LENGTH: 242
<212> TYPE: PRT
<213> ORGANISM: Artificial Sequence
<220> FEATURE:
<223> OTHER INFORMATION: inCT99 light chain

<400> SEQUENCE: 2

Ser Asp Gly Val Arg Gln Cys Arg Gly Asp Cys Phe Asp Gly Pro Leu
1               5                   10                  15

Met Gly Ser Ser Ser Asn Asp Ile Gln Met Thr Gln Ser Pro Ser Ser
            20                  25                  30

Leu Ser Ala Ser Val Gly Asp Arg Val Thr Ile Thr Cys Lys Ser Ser
        35                  40                  45

Gln Ser Leu Leu Asn Ser Arg Asp Gly Lys Asn Tyr Leu Ala Trp Tyr
    50                  55                  60

Gln Gln Lys Pro Gly Lys Ala Pro Lys Leu Leu Ile Tyr Asp Ala Ser
65                  70                  75                  80

Asn Leu Glu Thr Gly Val Pro Ser Arg Phe Ser Gly Ser Gly Ser Gly
                85                  90                  95

Thr Asp Phe Thr Phe Thr Ile Ser Ser Leu Gln Pro Glu Asp Ile Ala
            100                 105                 110

Thr Tyr Phe Cys Gln Gln Tyr Trp Tyr Trp Met Tyr Thr Phe Gly Gly
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys

<210> SEQ ID NO 3
<211> LENGTH: 15
<212> TYPE: PRT
<213> ORGANISM: Artificial Sequence
<220> FEATURE:
<223> OTHER INFORMATION: cyclic peptide in4

<400> SEQUENCE: 3

Asp Gly Val Arg Gln Cys Arg Gly Asp Cys Phe Asp Gly Pro Leu
1               5                   10                  15

<210> SEQ ID NO 4
<211> LENGTH: 5
<212> TYPE: PRT
<213> ORGANISM: Artificial Sequence
<220> FEATURE:
<223> OTHER INFORMATION: Linker

<400> SEQUENCE: 4
```

-continued

```
Gly Gly Gly Gly Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Linker

<400> SEQUENCE: 5

Gly Gly Gly Gly Ser Gly Phe Leu Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Linker

<400> SEQUENCE: 6

Pro Arg Ser Ala Lys Leu Glu Arg
1               5

<210> SEQ ID NO 7
<211> LENGTH: 119
<212> TYPE: PRT
<213> ORGANISM: Artificial Sequence
<220> FEATURE:
<223> OTHER INFORMATION: VH

<400> SEQUENCE: 7

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 8
<211> LENGTH: 108
<212> TYPE: PRT
<213> ORGANISM: Artificial Sequence
<220> FEATURE:
<223> OTHER INFORMATION: VL

<400> SEQUENCE: 8

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30
```

-continued

Ile His Trp Tyr Gln Gln Arg Thr Asn Gly Ser Pro Arg Leu Leu Ile
        35              40              45

Lys Tyr Ala Ser Glu Ser Ile Ser Gly Ile Pro Ser Arg Phe Ser Gly
    50              55              60

Ser Gly Ser Gly Thr Asp Phe Thr Leu Ser Ile Asn Ser Val Glu Ser
65              70              75              80

Glu Asp Ile Ala Asp Tyr Tyr Cys Gln Gln Asn Asn Asn Trp Pro Thr
                85              90              95

Thr Phe Gly Ala Gly Thr Lys Leu Glu Leu Lys Arg
        100             105

<210> SEQ ID NO 9
<211> LENGTH: 121
<212> TYPE: PRT
<213> ORGANISM: Artificial Sequence
<220> FEATURE:
<223> OTHER INFORMATION: VH

<400> SEQUENCE: 9

Gln Val Gln Leu Gln Glu Ser Gly Pro Gly Leu Val Lys Pro Ser Gln
1               5               10              15

Thr Leu Ser Leu Thr Cys Thr Val Ser Gly Gly Ser Ile Ser Ser Gly
        20              25              30

Asp Tyr Tyr Trp Ser Trp Ile Arg Gln Pro Pro Gly Lys Gly Leu Glu
        35              40              45

Trp Ile Gly Tyr Ile Tyr Tyr Ser Gly Ser Thr Asp Tyr Asn Pro Ser
    50              55              60

Leu Lys Ser Arg Val Thr Met Ser Val Asp Thr Ser Lys Asn Gln Phe
65              70              75              80

Ser Leu Lys Val Asn Ser Val Thr Ala Ala Asp Thr Ala Val Tyr Tyr
                85              90              95

Cys Ala Arg Val Ser Ile Phe Gly Val Gly Thr Phe Asp Tyr Trp Gly
            100             105             110

Gln Gly Thr Leu Val Thr Val Ser Ser
        115             120

<210> SEQ ID NO 10
<211> LENGTH: 108
<212> TYPE: PRT
<213> ORGANISM: Artificial Sequence
<220> FEATURE:
<223> OTHER INFORMATION: VL

<400> SEQUENCE: 10

Glu Ile Val Met Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
        20              25              30

Leu Ala Trp Tyr Gln Gln Lys Pro Gly Gln Ala Pro Arg Leu Leu Ile
        35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys His Gln Tyr Gly Ser Thr Pro Leu
                85              90              95

Thr Phe Gly Gly Gly Thr Lys Ala Glu Ile Lys Arg

-continued

```
              100               105
```

```
<210> SEQ ID NO 11
<211> LENGTH: 330
<212> TYPE: PRT
<213> ORGANISM: Artificial Sequence
<220> FEATURE:
<223> OTHER INFORMATION: Human IgG1 heavy chain constant region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 107
<212> TYPE: PRT
```

<213> ORGANISM: Artificial Sequence
<220> FEATURE:
<223> OTHER INFORMATION: Human IgG1 light chain constant region

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 9
<212> TYPE: PRT
<213> ORGANISM: Artificial Sequence
<220> FEATURE:
<223> OTHER INFORMATION: epitope

<400> SEQUENCE: 13

Asn Leu Val Pro Met Val Ala Thr Val
1               5

<210> SEQ ID NO 14
<211> LENGTH: 16
<212> TYPE: PRT
<213> ORGANISM: Artificial Sequence
<220> FEATURE:
<223> OTHER INFORMATION: epitope

<400> SEQUENCE: 14

Asn Leu Val Pro Met Val Ala Thr Val Gln Gly Gln Asn Leu Lys Tyr
1               5                   10                  15

<210> SEQ ID NO 15
<211> LENGTH: 24
<212> TYPE: PRT
<213> ORGANISM: Artificial Sequence
<220> FEATURE:
<223> OTHER INFORMATION: epitope

<400> SEQUENCE: 15

Ala Val Phe Thr Trp Pro Pro Trp Gln Ala Gly Ile Leu Ala Arg Asn
1               5                   10                  15

Leu Val Pro Met Val Ala Thr Val
            20

<210> SEQ ID NO 16
<211> LENGTH: 25
<212> TYPE: PRT
<213> ORGANISM: Artificial Sequence
<220> FEATURE:
<223> OTHER INFORMATION: epitope

<400> SEQUENCE: 16

```
Ala Val Phe Thr Trp Pro Pro Trp Gln Ala Gly Ile Leu Ala Arg Asn
1               5                   10                  15

Leu Val Pro Met Val Ala Thr Val Gln
            20                  25

<210> SEQ ID NO 17
<211> LENGTH: 26
<212> TYPE: PRT
<213> ORGANISM: Artificial Sequence
<220> FEATURE:
<223> OTHER INFORMATION: epitope

<400> SEQUENCE: 17

Ala Val Phe Thr Trp Pro Pro Trp Gln Ala Gly Ile Leu Ala Arg Asn
1               5                   10                  15

Leu Val Pro Met Val Ala Thr Val Gln Gly
            20                  25

<210> SEQ ID NO 18
<211> LENGTH: 27
<212> TYPE: PRT
<213> ORGANISM: Artificial Sequence
<220> FEATURE:
<223> OTHER INFORMATION: epitope

<400> SEQUENCE: 18

Ala Val Phe Thr Trp Pro Pro Trp Gln Ala Gly Ile Leu Ala Arg Asn
1               5                   10                  15

Leu Val Pro Met Val Ala Thr Val Gln Gly Gln
            20                  25

<210> SEQ ID NO 19
<211> LENGTH: 28
<212> TYPE: PRT
<213> ORGANISM: Artificial Sequence
<220> FEATURE:
<223> OTHER INFORMATION: epitope

<400> SEQUENCE: 19

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn
            20                  25

<210> SEQ ID NO 20
<211> LENGTH: 29
<212> TYPE: PRT
<213> ORGANISM: Artificial Sequence
<220> FEATURE:
<223> OTHER INFORMATION: epitope

<400> SEQUENCE: 20

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu
            20                  25

<210> SEQ ID NO 21
<211> LENGTH: 30
<212> TYPE: PRT
<213> ORGANISM: Artificial Sequence
<220> FEATURE:
<223> OTHER INFORMATION: epitope

<400> SEQUENCE: 21
```

-continued

```
Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu Lys
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: epitope

<400> SEQUENCE: 22

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu Lys Tyr
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: epitope

<400> SEQUENCE: 23

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu Lys Tyr Gln
            20                  25                  30

<210> SEQ ID NO 24
<211> LENGTH: 33
<212> TYPE: PRT
<213> ORGANISM: Artificial Sequence
<220> FEATURE:
<223> OTHER INFORMATION: epitope

<400> SEQUENCE: 24

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu Lys Tyr Gln
            20                  25                  30

Glu

<210> SEQ ID NO 25
<211> LENGTH: 34
<212> TYPE: PRT
<213> ORGANISM: Artificial Sequence
<220> FEATURE:
<223> OTHER INFORMATION: epitope

<400> SEQUENCE: 25

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu Lys Tyr Gln
            20                  25                  30

Glu Phe

<210> SEQ ID NO 26
<211> LENGTH: 37
<212> TYPE: PRT
```

<213> ORGANISM: Artificial Sequence
<220> FEATURE:
<223> OTHER INFORMATION: epitope

<400> SEQUENCE: 26

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu Lys Tyr Gln
            20                  25                  30

Glu Phe Phe Trp Asp
        35

<210> SEQ ID NO 27
<211> LENGTH: 40
<212> TYPE: PRT
<213> ORGANISM: Artificial Sequence
<220> FEATURE:
<223> OTHER INFORMATION: epitope

<400> SEQUENCE: 27

Ala Val Phe Thr Trp Pro Pro Trp Gln Ala Gly Ile Leu Ala Arg Asn
1               5                   10                  15

Leu Val Pro Met Val Ala Thr Val Gln Gly Gln Asn Leu Lys Tyr Gln
            20                  25                  30

Glu Phe Phe Trp Asp Ala Asn Asp
        35                  40

<210> SEQ ID NO 28
<211> LENGTH: 19
<212> TYPE: PRT
<213> ORGANISM: Artificial Sequence
<220> FEATURE:
<223> OTHER INFORMATION: epitope

<400> SEQUENCE: 28

Gly Ile Leu Ala Arg Asn Leu Val Pro Met Val Ala Thr Val Gln Gly
1               5                   10                  15

Gln Asn Leu

<210> SEQ ID NO 29
<211> LENGTH: 9
<212> TYPE: PRT
<213> ORGANISM: Artificial Sequence
<220> FEATURE:
<223> OTHER INFORMATION: epitope

<400> SEQUENCE: 29

Tyr Met Leu Asp Leu Gln Pro Glu Thr
1               5

<210> SEQ ID NO 30
<211> LENGTH: 19
<212> TYPE: PRT
<213> ORGANISM: Artificial Sequence
<220> FEATURE:
<223> OTHER INFORMATION: epitope

<400> SEQUENCE: 30

Met His Gly Asp Thr Pro Thr Leu His Glu Tyr Met Leu Asp Leu Gln
1               5                   10                  15

Pro Glu Thr

<210> SEQ ID NO 31

```
<211> LENGTH: 9
<212> TYPE: PRT
<213> ORGANISM: Artificial Sequence
<220> FEATURE:
<223> OTHER INFORMATION: epitope

<400> SEQUENCE: 31

Phe Leu Tyr Ala Leu Ala Leu Leu Leu
1               5

<210> SEQ ID NO 32
<211> LENGTH: 9
<212> TYPE: PRT
<213> ORGANISM: Artificial Sequence
<220> FEATURE:
<223> OTHER INFORMATION: epitope

<400> SEQUENCE: 32

Ser Leu Gly Gly Leu Leu Thr Met Val
1               5

<210> SEQ ID NO 33
<211> LENGTH: 9
<212> TYPE: PRT
<213> ORGANISM: Artificial Sequence
<220> FEATURE:
<223> OTHER INFORMATION: epitope

<400> SEQUENCE: 33

Ser Leu Gly Gly Leu Leu Thr Met Val
1               5

<210> SEQ ID NO 34
<211> LENGTH: 18
<212> TYPE: PRT
<213> ORGANISM: Artificial Sequence
<220> FEATURE:
<223> OTHER INFORMATION: epitope

<400> SEQUENCE: 34

Asn Arg Thr Tyr Gly Pro Val Phe Met Ser Leu Gly Gly Leu Leu Thr
1               5                   10                  15

Met Val

<210> SEQ ID NO 35
<211> LENGTH: 22
<212> TYPE: PRT
<213> ORGANISM: Artificial Sequence
<220> FEATURE:
<223> OTHER INFORMATION: epitope

<400> SEQUENCE: 35

Trp Gly Ser Gly Asn Arg Thr Tyr Gly Pro Val Phe Met Ser Leu Gly
1               5                   10                  15

Gly Leu Leu Thr Met Val
            20

<210> SEQ ID NO 36
<211> LENGTH: 26
<212> TYPE: PRT
<213> ORGANISM: Artificial Sequence
<220> FEATURE:
<223> OTHER INFORMATION: epitope

<400> SEQUENCE: 36

Ile Leu Thr Glu Trp Gly Ser Gly Asn Arg Thr Tyr Gly Pro Val Phe
```

-continued

```
1               5               10              15

Met Ser Leu Gly Gly Leu Leu Thr Met Val
        20              25
```

<210> SEQ ID NO 37
<211> LENGTH: 127
<212> TYPE: PRT
<213> ORGANISM: Artificial Sequence
<220> FEATURE:
<223> OTHER INFORMATION: VH

<400> SEQUENCE: 37

```
Glu Val Gln Leu Val Gln Ser Gly Ala Glu Val Lys Lys Pro Gly Ser
1               5               10              15

Ser Val Lys Val Ser Cys Lys Ala Ser Gly Gly Thr Phe Ser Ser Tyr
        20              25              30

Ala Ile Ser Trp Val Arg Gln Ala Pro Gly Gln Gly Leu Glu Trp Met
        35              40              45

Gly Gly Ile Ile Pro Ile Phe Gly Thr Ala Asn Tyr Ala Gln Lys Phe
    50              55              60

Gln Gly Arg Val Thr Ile Thr Ala Asp Glu Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Gly Asp Leu Tyr Tyr Tyr Asp Ser Ser Gly Tyr Pro Arg Tyr
        100             105             110

Tyr Phe Asp Tyr Trp Gly Gln Gly Thr Leu Val Thr Val Ser Ser
        115             120             125
```

<210> SEQ ID NO 38
<211> LENGTH: 110
<212> TYPE: PRT
<213> ORGANISM: Artificial Sequence
<220> FEATURE:
<223> OTHER INFORMATION: VL

<400> SEQUENCE: 38

```
Glu Thr Thr Leu Thr Gln Ser Pro Gly Thr Leu Ser Leu Ser Pro Gly
1               5               10              15

Glu Arg Ala Thr Leu Ser Cys Arg Ala Ser Gln Ser Val Ser Ser Ser
        20              25              30

Tyr Leu Ala Trp Tyr Gln Gln Lys Pro Gly Gln Ala Pro Arg Leu Val
        35              40              45

Ile Tyr Gly Ala Ser Ser Arg Ala Thr Gly Ile Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln His Tyr Ser Thr Ser Pro
            85              90              95

Gly Phe Thr Phe Gly Gln Gly Thr Lys Leu Glu Ile Arg Arg
        100             105             110
```

<210> SEQ ID NO 39
<211> LENGTH: 127
<212> TYPE: PRT
<213> ORGANISM: Artificial Sequence
<220> FEATURE:
<223> OTHER INFORMATION: VH

<400> SEQUENCE: 39

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Leu Tyr Tyr Tyr Asp Ser Ser Gly Tyr Pro Leu Trp
            100                 105                 110

Tyr Met Asp Tyr Trp Gly Gln Gly Thr Leu Val Thr Val Ser Ser
        115                 120                 125
```

<210> SEQ ID NO 40
<211> LENGTH: 110
<212> TYPE: PRT
<213> ORGANISM: Artificial Sequence
<220> FEATURE:
<223> OTHER INFORMATION: VL

<400> SEQUENCE: 40

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Val
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Asp Tyr Ser Thr Tyr Pro
                85                  90                  95

Ala Phe Thr Phe Gly Gln Gly Thr Lys Leu Glu Ile Arg Arg
            100                 105                 110
```

<210> SEQ ID NO 41
<211> LENGTH: 127
<212> TYPE: PRT
<213> ORGANISM: Artificial Sequence
<220> FEATURE:
<223> OTHER INFORMATION: VH

<400> SEQUENCE: 41

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
```

```
         65                  70                  75                  80
Met Glu Leu Ser Ser Leu Arg Ser Glu Asp Thr Ala Val Tyr Tyr Cys
                     85                  90                  95

Ala Arg Gly Asp Leu Tyr Tyr Tyr Asp Ser Ser Gly Tyr Pro Trp Tyr
                 100                 105                 110

Tyr Met Asp Tyr Trp Gly Gln Gly Thr Leu Val Thr Val Ser Ser
             115                 120                 125
```

<210> SEQ ID NO 42
<211> LENGTH: 110
<212> TYPE: PRT
<213> ORGANISM: Artificial Sequence
<220> FEATURE:
<223> OTHER INFORMATION: VL

<400> SEQUENCE: 42

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Val
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Ser Tyr Ala Phe Pro
                     85                  90                  95

Gly Phe Thr Phe Gly Gln Gly Thr Lys Leu Glu Ile Arg Arg
                 100                 105                 110
```

<210> SEQ ID NO 43
<211> LENGTH: 127
<212> TYPE: PRT
<213> ORGANISM: Artificial Sequence
<220> FEATURE:
<223> OTHER INFORMATION: VH

<400> SEQUENCE: 43

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Ser Ile Ile Pro Ile Phe Gly Val Ala Glu Tyr Ala His Lys Phe
         50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                     85                  90                  95

Ala Arg Gly Asp Leu Tyr Tyr Tyr Asp Ser Ser Gly Tyr Pro Leu Trp
                 100                 105                 110

Tyr Met Asp Tyr Trp Gly Gln Gly Thr Leu Val Thr Val Ser Ser
             115                 120                 125
```

<210> SEQ ID NO 44
<211> LENGTH: 110

<212> TYPE: PRT
<213> ORGANISM: Artificial Sequence
<220> FEATURE:
<223> OTHER INFORMATION: VL

<400> SEQUENCE: 44

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Val
        35                  40                  45

Ile Tyr Gly Ala Ser Thr Arg Pro Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Asp Tyr Ser Thr Tyr Pro
                85                  90                  95

Ala Phe Thr Phe Gly Gln Gly Thr Lys Leu Glu Ile Arg Arg
            100                 105                 110
```

<210> SEQ ID NO 45
<211> LENGTH: 118
<212> TYPE: PRT
<213> ORGANISM: Artificial Sequence
<220> FEATURE:
<223> OTHER INFORMATION: VH

<400> SEQUENCE: 45

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Pro Gln Ser Trp Tyr Arg Gly Asp Val Trp Gly Gln Gly Thr
            100                 105                 110

Leu Val Thr Val Ser Ser
        115
```

<210> SEQ ID NO 46
<211> LENGTH: 110
<212> TYPE: PRT
<213> ORGANISM: Artificial Sequence
<220> FEATURE:
<223> OTHER INFORMATION: VL

<400> SEQUENCE: 46

```
Ser Tyr Glu Leu Thr Gln Pro Pro Ser Val Ser Gly Thr Pro Gly Gln
1               5                   10                  15

Arg Val Ala Ile Ser Cys Ser Gly Ser Ser Ser Asn Ile Gly Thr Arg
            20                  25                  30

Met Val Thr Trp Tyr Gln His Val Pro Gly Thr Ala Pro Lys Leu Leu
```

```
              35                    40                    45
Ile Phe Asn Asn Asn Gln Arg Pro Ser Gly Val Pro Asp Arg Phe Ser
    50                    55                    60

Ala Ser Lys Ser Gly Thr Ser Ala Ser Leu Ala Ile Ile Gly Leu Gln
65                    70                    75                    80

Ser Asp Asp Glu Ala Asp Tyr Tyr Cys Ala Ala Trp Asp Asp Asn Leu
                85                    90                    95

Lys Ser Tyr Val Phe Gly Thr Gly Thr Lys Val Thr Val Leu
                100                   105                   110
```

<210> SEQ ID NO 47
<211> LENGTH: 117
<212> TYPE: PRT
<213> ORGANISM: Artificial Sequence
<220> FEATURE:
<223> OTHER INFORMATION: VH

<400> SEQUENCE: 47

```
Gln Val Gln Leu Lys Gln Ser Gly Pro Gly Leu Val Gln Pro Ser Gln
1                     5                     10                    15

Ser Leu Ser Ile Thr Cys Thr Val Ser Gly Phe Ser Leu Thr Asn Tyr
                20                    25                    30

Gly Val His Trp Val Arg Gln Ser Pro Gly Lys Gly Leu Glu Trp Leu
          35                    40                    45

Gly Val Ile Trp Ser Gly Gly Ser Thr Asp Tyr Asn Ala Ala Phe Ile
          50                    55                    60

Ser Arg Leu Ser Ile Ser Lys Asp Asn Ser Lys Ser Gln Val Phe Phe
65                    70                    75                    80

Lys Met Asn Ser Leu Gln Ala Asn Asp Thr Ala Ile Tyr Tyr Cys Ala
                85                    90                    95

Arg Asn Trp Val Pro Tyr Tyr Phe Asp Tyr Trp Gly Gln Gly Thr Thr
                100                   105                   110

Leu Thr Val Ser Ser
          115
```

<210> SEQ ID NO 48
<211> LENGTH: 108
<212> TYPE: PRT
<213> ORGANISM: Artificial Sequence
<220> FEATURE:
<223> OTHER INFORMATION: VL

<400> SEQUENCE: 48

```
Asp Ile Val Met Thr Gln Ser Gln Lys Phe Met Ser Thr Ser Val Gly
1                     5                     10                    15

Asp Arg Val Ser Val Thr Cys Arg Ala Ser Gln Asn Val Phe Thr Asn
                20                    25                    30

Val Ala Trp Tyr Gln Gln Lys Pro Gly Gln Ala Pro Lys Ala Leu Ile
          35                    40                    45

Tyr Ser Thr Ser Tyr Arg Tyr Ser Gly Val Pro Asp Arg Phe Thr Gly
          50                    55                    60

Ser Gly Ser Gly Thr Asp Phe Thr Leu Thr Ile Ser Asn Val Gln Ser
65                    70                    75                    80

Glu Asp Leu Ala Glu Tyr Phe Cys Gln Gln Tyr Ile Ser Tyr Pro Leu
                85                    90                    95

Thr Phe Gly Ala Gly Thr Lys Leu Glu Leu Lys Arg
                100                   105
```

<210> SEQ ID NO 49
<211> LENGTH: 330
<212> TYPE: PRT
<213> ORGANISM: Artificial Sequence
<220> FEATURE:
<223> OTHER INFORMATION: Mouse IgG2a heavy chain constant region

<400> SEQUENCE: 49

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 50
<211> LENGTH: 106
<212> TYPE: PRT
<213> ORGANISM: Artificial Sequence
<220> FEATURE:

<223> OTHER INFORMATION: Mouse C kappa light chain constant region

<400> SEQUENCE: 50

```
Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```

```
<210> SEQ ID NO 51
<211> LENGTH: 8
<212> TYPE: PRT
<213> ORGANISM: Artificial Sequence
<220> FEATURE:
<223> OTHER INFORMATION: T-cell antigen epitope sequence of H-2Kb
```

<400> SEQUENCE: 51

```
Ser Ile Ile Asn Phe Glu Lys Leu
1               5
```

```
<210> SEQ ID NO 52
<211> LENGTH: 9
<212> TYPE: PRT
<213> ORGANISM: Artificial Sequence
<220> FEATURE:
<223> OTHER INFORMATION: antibody-EBV LMP2 peptide 426-434
```

<400> SEQUENCE: 52

```
Cys Leu Gly Gly Leu Leu Thr Met Val
1               5
```

```
<210> SEQ ID NO 53
<211> LENGTH: 13
<212> TYPE: PRT
<213> ORGANISM: Artificial Sequence
<220> FEATURE:
<223> OTHER INFORMATION: Linker
```

<400> SEQUENCE: 53

```
Gly Gly Gly Gly Ser Pro Arg Ser Ala Lys Leu Glu Arg
1               5                   10
```

```
<210> SEQ ID NO 54
<211> LENGTH: 9
<212> TYPE: PRT
<213> ORGANISM: Artificial Sequence
<220> FEATURE:
<223> OTHER INFORMATION: synthetic construct
```

<400> SEQUENCE: 54

```
Ser Leu Gly Gly Leu Leu Thr Met Val
1               5
```

```
<210> SEQ ID NO 55
```

```
<211> LENGTH: 25
<212> TYPE: PRT
<213> ORGANISM: Artificial Sequence
<220> FEATURE:
<223> OTHER INFORMATION: epitope (N-terminally extended peptide)

<400> SEQUENCE: 55

Ala Val Phe Thr Trp Pro Pro Trp Gln Ala Gly Ile Leu Ala Arg Asn
1               5                   10                  15

Leu Val Pro Met Val Ala Ala Thr Val
            20                  25

<210> SEQ ID NO 56
<211> LENGTH: 32
<212> TYPE: PRT
<213> ORGANISM: Artificial Sequence
<220> FEATURE:
<223> OTHER INFORMATION: epitope (N- and C-terminally extended peptide)

<400> SEQUENCE: 56

Ala Val Phe Thr Trp Pro Pro Trp Gln Ala Gly Ile Leu Ala Arg Asn
1               5                   10                  15

Leu Val Pro Met Val Ala Ala Thr Val Gln Gly Gln Asn Leu Lys Tyr
            20                  25                  30

<210> SEQ ID NO 57
<211> LENGTH: 38
<212> TYPE: PRT
<213> ORGANISM: Artificial Sequence
<220> FEATURE:
<223> OTHER INFORMATION: epitope (N- and C-terminally extended peptide)

<400> SEQUENCE: 57

Ala Val Phe Thr Trp Pro Pro Trp Gln Ala Gly Ile Leu Ala Arg Asn
1               5                   10                  15

Leu Val Pro Met Val Ala Ala Thr Val Gln Gly Gln Asn Leu Lys Tyr
            20                  25                  30

Gln Glu Phe Phe Trp Asp
        35

<210> SEQ ID NO 58
<211> LENGTH: 6
<212> TYPE: PRT
<213> ORGANISM: Artificial Sequence
<220> FEATURE:
<223> OTHER INFORMATION: Linker

<400> SEQUENCE: 58

Met Gly Ser Ser Ser Asn
1               5

<210> SEQ ID NO 59
<211> LENGTH: 4
<212> TYPE: PRT
<213> ORGANISM: Artificial Sequence
<220> FEATURE:
<223> OTHER INFORMATION: Linker

<400> SEQUENCE: 59

Gly Phe Leu Gly
1
```